(12) United States Patent
Miyashita et al.

(10) Patent No.: US 12,172,941 B2
(45) Date of Patent: Dec. 24, 2024

(54) ORGANIC COMPOUND AND ORGANIC LIGHT-EMITTING DEVICE

(71) Applicant: CANON KABUSHIKI KAISHA, Tokyo (JP)

(72) Inventors: Hirokazu Miyashita, Kanagawa (JP); Naoki Yamada, Tokyo (JP); Hiroki Ohrui, Kanagawa (JP); Yosuke Nishide, Kanagawa (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 638 days.

(21) Appl. No.: 17/471,050

(22) Filed: Sep. 9, 2021

(65) Prior Publication Data

US 2022/0081378 A1 Mar. 17, 2022

(30) Foreign Application Priority Data

Sep. 11, 2020 (JP) .................................. 2020-152683

(51) Int. Cl.
*C07C 13/66* (2006.01)
*C07C 22/08* (2006.01)
(Continued)

(52) U.S. Cl.
CPC .............. *C07C 13/66* (2013.01); *C07C 22/08* (2013.01); *C07C 25/22* (2013.01); *C07C 43/21* (2013.01);
(Continued)

(58) Field of Classification Search
CPC ...................................................... C07C 13/62
See application file for complete search history.

(56) References Cited

U.S. PATENT DOCUMENTS 10,840,470 B2 * 11/2020 Takahashi ............ H10K 50/131

FOREIGN PATENT DOCUMENTS

CN 101752511 A 6/2010
CN 102245546 A 11/2011
(Continued)

*Primary Examiner* — Vu A Nguyen
(74) *Attorney, Agent, or Firm* — Canon U.S.A., Inc. I.P. Division

(57) ABSTRACT

An organic compound represented by the following formula [1] or [2]:

(Continued)

wherein $R_1$ to $R_{22}$ independently denote a substituent selected from a hydrogen atom, a halogen atom, a substituted or unsubstituted alkyl group, a substituted or unsubstituted alkoxy group, a substituted or unsubstituted amino group, a substituted or unsubstituted aryloxy group, a substituted or unsubstituted silyl group, a cyano group, a trifluoromethyl group, a substituted or unsubstituted aromatic hydrocarbon group, and a substituted or unsubstituted heterocyclic group, and $R_5$ and $R_6$, and/or $R_7$ and $R_8$ may be bonded together to form a ring structure.

22 Claims, 8 Drawing Sheets

(51) Int. Cl.
  C07C 25/22       (2006.01)
  C07C 43/21       (2006.01)
  C07C 43/275      (2006.01)
  C07C 211/61      (2006.01)
  C07C 255/52      (2006.01)
  C07D 333/08      (2006.01)
  C07D 401/10      (2006.01)
  C07D 403/10      (2006.01)
  C07D 405/10      (2006.01)
  C07D 409/10      (2006.01)
  C07D 409/14      (2006.01)
  C07D 413/10      (2006.01)
  C07D 417/10      (2006.01)
  C07D 519/00      (2006.01)
  H10K 50/15       (2023.01)
  H10K 85/60       (2023.01)
  H10K 101/30      (2023.01)

(52) U.S. Cl.
  CPC .......... *C07C 43/275* (2013.01); *C07C 211/61* (2013.01); *C07C 255/52* (2013.01); *C07D 333/08* (2013.01); *C07D 401/10* (2013.01); *C07D 403/10* (2013.01); *C07D 405/10* (2013.01); *C07D 409/10* (2013.01); *C07D 409/14* (2013.01); *C07D 413/10* (2013.01); *C07D 417/10* (2013.01); *C07D 519/00* (2013.01); *H10K 50/15* (2023.02); *H10K 85/622* (2023.02); *H10K 85/626* (2023.02); *H10K 85/633* (2023.02); *H10K 85/636* (2023.02); *H10K 85/655* (2023.02); *H10K 85/6572* (2023.02); *H10K 85/6574* (2023.02); *H10K 85/6576* (2023.02); *H10K 2101/30* (2023.02)

(56) References Cited

FOREIGN PATENT DOCUMENTS

| | | | | |
|---|---|---|---|---|
| EP | 2200104 A2 | * | 6/2010 | ............ C07C 13/62 |
| JP | 2010143879 A | | 7/2010 | |
| WO | WO-2010071224 A1 | * | 6/2010 | ............ C07C 13/62 |
| WO | WO-2013042357 A1 | * | 3/2013 | ................ B41J 2/45 |
| WO | WO-2014024687 A1 | * | 2/2014 | ............ C07C 13/62 |

* cited by examiner

ORGANIC COMPOUND AND ORGANIC LIGHT-EMITTING DEVICE

BACKGROUND OF THE INVENTION

Field of the Invention

The present disclosure relates to an organic compound and an organic light-emitting device including the organic compound.

Description of the Related Art

An organic light-emitting device (hereinafter also referred to as an "organic electroluminescent device" or an "organic EL device") is an electronic device that includes a pair of electrodes and an organic compound layer between the electrodes. Electrons and holes are injected from the pair of electrodes to generate an exciton of a light-emitting organic compound in the organic compound layer. When the exciton returns to its ground state, the organic light-emitting device emits light.

With recent significant advances in organic light-emitting devices, it is possible to realize low drive voltage, various emission wavelengths, high-speed responsivity, and thin and light light-emitting devices.

Light-emitting organic compounds have been actively developed. This is because compounds with good emission properties are important for the development of high-performance organic light-emitting devices. Japanese Patent Laid-Open No. 2010-143879 (Patent Literature 1) discloses the following compound 1-A as a compound developed so far.

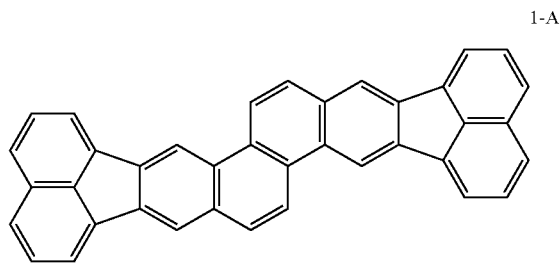 [SMILES: c1cc2c3c(cccc3c1)-c1cc3c(ccc4c5cc6c(cc5ccc34)-c3cccc4cccc-6c34)cc1-2]

1-A

SUMMARY OF THE INVENTION

The present disclosure provides an organic compound represented by the following formula [1] or [2]:

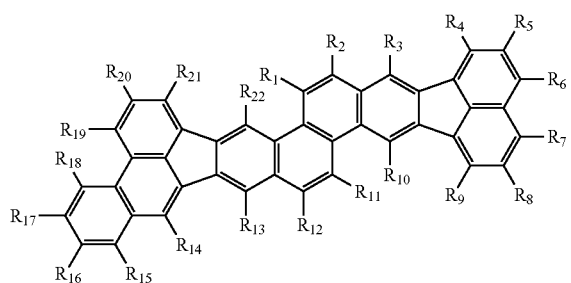

[1]

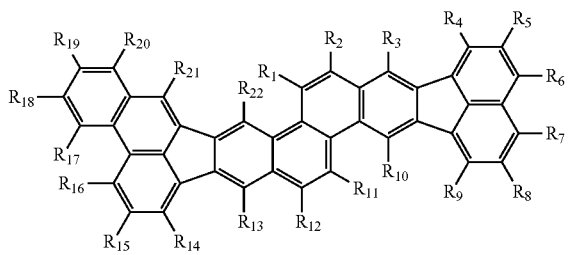

[2]

wherein $R_1$ to $R_{22}$ independently denote a substituent selected from a hydrogen atom, a halogen atom, a substituted or unsubstituted alkyl group, a substituted or unsubstituted alkoxy group, a substituted or unsubstituted amino group, a substituted or unsubstituted aryloxy group, a substituted or unsubstituted silyl group, a cyano group, a trifluoromethyl group, a substituted or unsubstituted aromatic hydrocarbon group, and a substituted or unsubstituted heterocyclic group, and $R_5$ and $R_6$, and/or $R_7$ and $R_8$ may be bonded together to form a ring structure.

Further features of the present disclosure will become apparent from the following description of exemplary embodiments with reference to the attached drawings.

DESCRIPTION OF THE EMBODIMENTS

Figure 1:
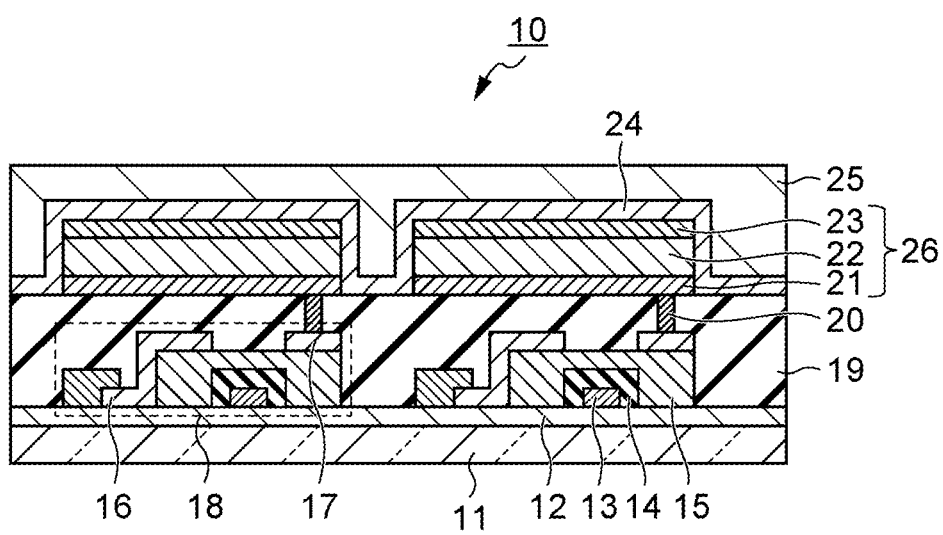
FIG. 1 is a schematic cross-sectional view of an example of a display apparatus including an organic light-emitting device according to an embodiment of the present disclosure.

The compound in Patent Literature 1 has room for further improvement in emission properties. An organic light-emitting device with higher luminescence efficiency can be provided by improving the emission properties of a compound.

Accordingly, the present disclosure provides an organic compound with good emission properties and also provides an organic light-emitting device with good emission properties.

<<Organic Compound>>

First, an organic compound according to the present embodiment is described below. The organic compound according to the present embodiment is represented by the following formula [1] or [2].

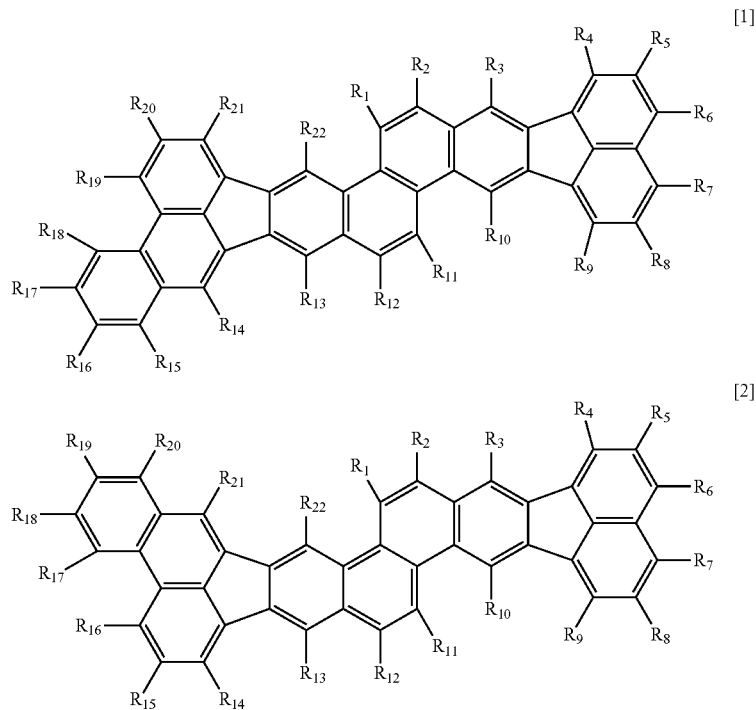

In the formula [1] or [2], $R_1$ to $R_{22}$ independently denote a substituent selected from a hydrogen atom, a halogen atom, a substituted or unsubstituted alkyl group, a substituted or unsubstituted alkoxy group, a substituted or unsubstituted amino group, a substituted or unsubstituted aryloxy group, a substituted or unsubstituted silyl group, a cyano group, a trifluoromethyl group, a substituted or unsubstituted aromatic hydrocarbon group, and a substituted or unsubstituted heterocyclic group.

The halogen atoms represented by $R_1$ to $R_{22}$ may be, but are not limited to, fluorine, chlorine, bromine, and iodine.

Examples of the alkyl group represented by $R_1$ to $R_{22}$ include, but are not limited to, a methyl group, an ethyl group, a n-propyl group, an isopropyl group, a n-butyl group, a tertiary butyl group, a secondary butyl group, an octyl group, a cyclohexyl group, a 1-adamantyl group, and a 2-adamantyl group. Among these, an alkyl group having 1 to 10 carbon atoms can be used.

Examples of the alkoxy group represented by $R_1$ to $R_{22}$ include, but are not limited to, a methoxy group, an ethoxy group, a propoxy group, a 2-ethyl-octyloxy group, and a benzyloxy group. Among these, an alkoxy group having 1 to 10 carbon atoms can be used.

Examples of the amino group represented by $R_1$ to $R_{22}$ include, but are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenyl amino group, an N-phenyl-N-tolylamino group, an N,N-ditolylamino group, an N-methyl-N-phenylamino group, an N,N-dianisolyl amino group, an N-mesityl-N-phenylamino group, an N,N-dimesitylamino group, an N-phenyl-N-(4-tertiary butylphenyl)amino group, an N-phenyl-N-(4-trifluoromethylphenyl)amino group, and an N-piperidyl group. Among these, an amino group having 1 to 6 carbon atoms can be used.

Examples of the aryloxy group represented by $R_1$ to $R_{22}$ include, but are not limited to, a phenoxy group and a thienyloxy group.

Examples of the silyl group represented by $R_1$ to $R_{22}$ include, but are not limited to, a trimethylsilyl group and a triphenylsilyl group.

Examples of the aromatic hydrocarbon group represented by $R_1$ to $R_{22}$ include, but are not limited to, a phenyl group, a naphthyl group, an indenyl group, a biphenyl group, a terphenyl group, a fluorenyl group, a phenanthryl group, a fluoranthenyl group, and a triphenylenyl group. Among these, an aromatic hydrocarbon group having 6 to 30 carbon atoms can be used.

Examples of the heterocyclic group represented by $R_1$ to $R_{22}$ include, but are not limited to, a pyridyl group, an oxazolyl group, an oxadiazolyl group, a thiazolyl group, a thiadiazolyl group, a carbazolyl group, an acridinyl group, a phenanthrolyl group, a dibenzofuranyl group, and a dibenzothiophenyl group. Among these, a heterocyclic group having 3 to 27 carbon atoms can be used.

Examples of substituents that the alkyl group, alkoxy group, amino group, aryloxy group, silyl group, aromatic hydrocarbon group, and heterocyclic group represented by $R_1$ to $R_{22}$ may further have include halogen atoms, such as fluorine, chlorine, bromine, and iodine; alkyl groups, such as a methyl group, an ethyl group, a n-propyl group, isopropyl group, a n-butyl group, a tertiary butyl group; alkoxy groups, such as a methoxy group, an ethoxy group, and a propoxy group; amino groups, such as a dimethylamino group, a diethylamino group, a dibenzylamino group, a diphenylamino group, and a ditolylamino group; aryloxy groups, such as a phenoxy group; aromatic hydrocarbon groups, such as a phenyl group and a biphenyl group; heterocyclic groups, such as a pyridyl group and a pyrrolyl group; and a cyano group.

In the organic compound according to the present embodiment, $R_5$ and $R_6$, and/or $R_7$ and $R_8$ may be bonded together to form a ring structure.

In an organic compound according to a first embodiment, neither $R_5$ and $R_6$ nor $R_7$ and $R_8$ are bonded together to form a ring structure.

An organic compound according to a second embodiment is represented by one of the following formulae [3] to [5].

In the formulae [3] to [5], $R_{23}$ to $R_{26}$ independently denote a substituent selected from a hydrogen atom, a halogen atom, a substituted or unsubstituted alkyl group, a substituted or unsubstituted alkoxy group, a substituted or unsubstituted amino group, a substituted or unsubstituted aryloxy group, a substituted or unsubstituted silyl group, a cyano group, a trifluoromethyl group, a substituted or unsubstituted aromatic hydrocarbon group, and a substituted or unsubstituted heterocyclic group.

The halogen atom, alkyl group, alkoxy group, amino group, aryloxy group, silyl group, cyano group, trifluoromethyl group, aromatic hydrocarbon group, and heterocyclic group represented by $R_{23}$ to $R_{26}$ may be the same as those described for $R_1$ to $R_{22}$. Substituents that the alkyl group, alkoxy group, amino group, aryloxy group, silyl group, aromatic hydrocarbon group, and heterocyclic group represented by $R_{23}$ to $R_{26}$ may further have may be the same as those described for $R_1$ to $R_{22}$.

In the organic compound according to the present embodiment, at least one of $R_1$ to $R_3$, $R_{10}$ to $R_{13}$, and $R_{22}$ may be a substituent selected from a substituted or unsub-

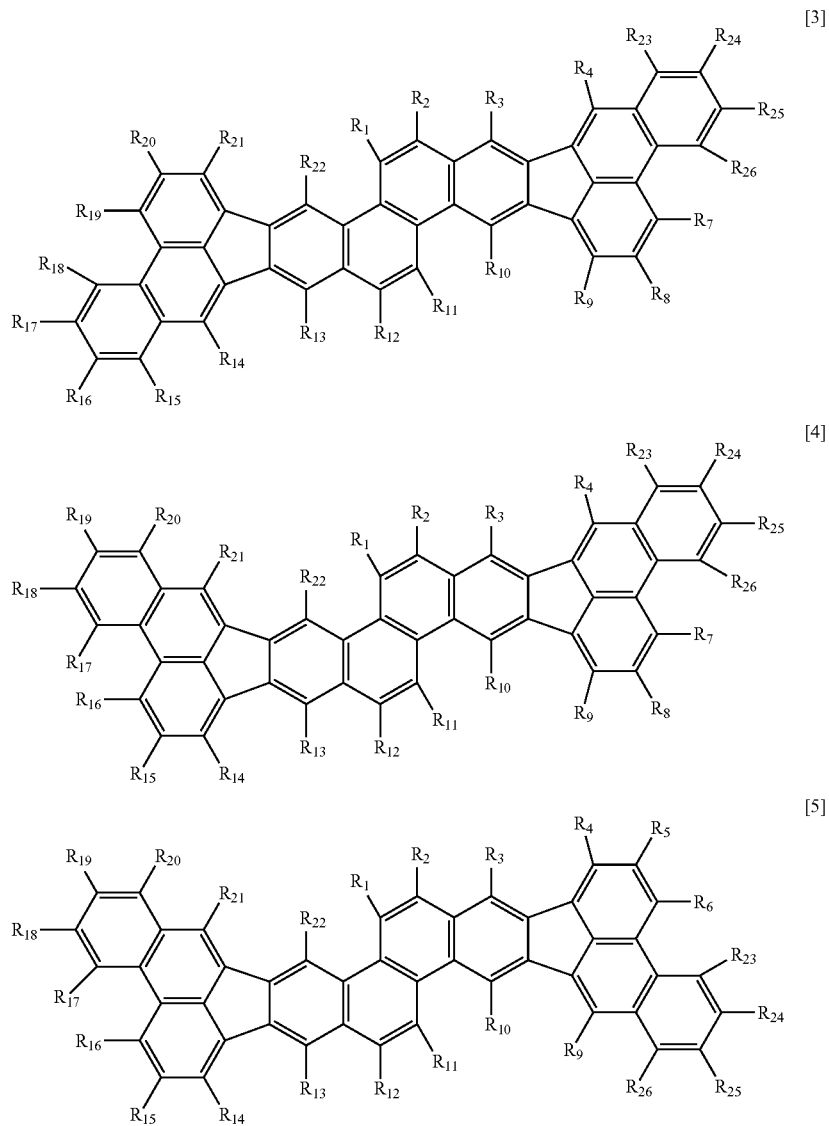

stituted aromatic hydrocarbon group and a substituted or unsubstituted heterocyclic group. At least one of $R_2$ and $R_3$, $R_{10}$, $R_{12}$ and $R_{13}$, and $R_{22}$ may be a substituent selected from a substituted or unsubstituted aromatic hydrocarbon group and a substituted or unsubstituted heterocyclic group. At least one of $R_2$ and $R_3$, $R_{10}$, $R_{12}$ and $R_{13}$, and $R_{22}$ may be a substituted or unsubstituted phenyl group or a substituted or unsubstituted naphthyl group. At least one of $R_2$ and $R_3$, $R_{10}$, $R_{12}$ and $R_{13}$, and $R_{22}$ may be a phenyl group with a cyano group or a naphthyl group with a cyano group.

Next, a method for synthesizing the organic compound according to the present embodiment is described. For example, the organic compound according to the present embodiment is synthesized in accordance with the following reaction scheme.

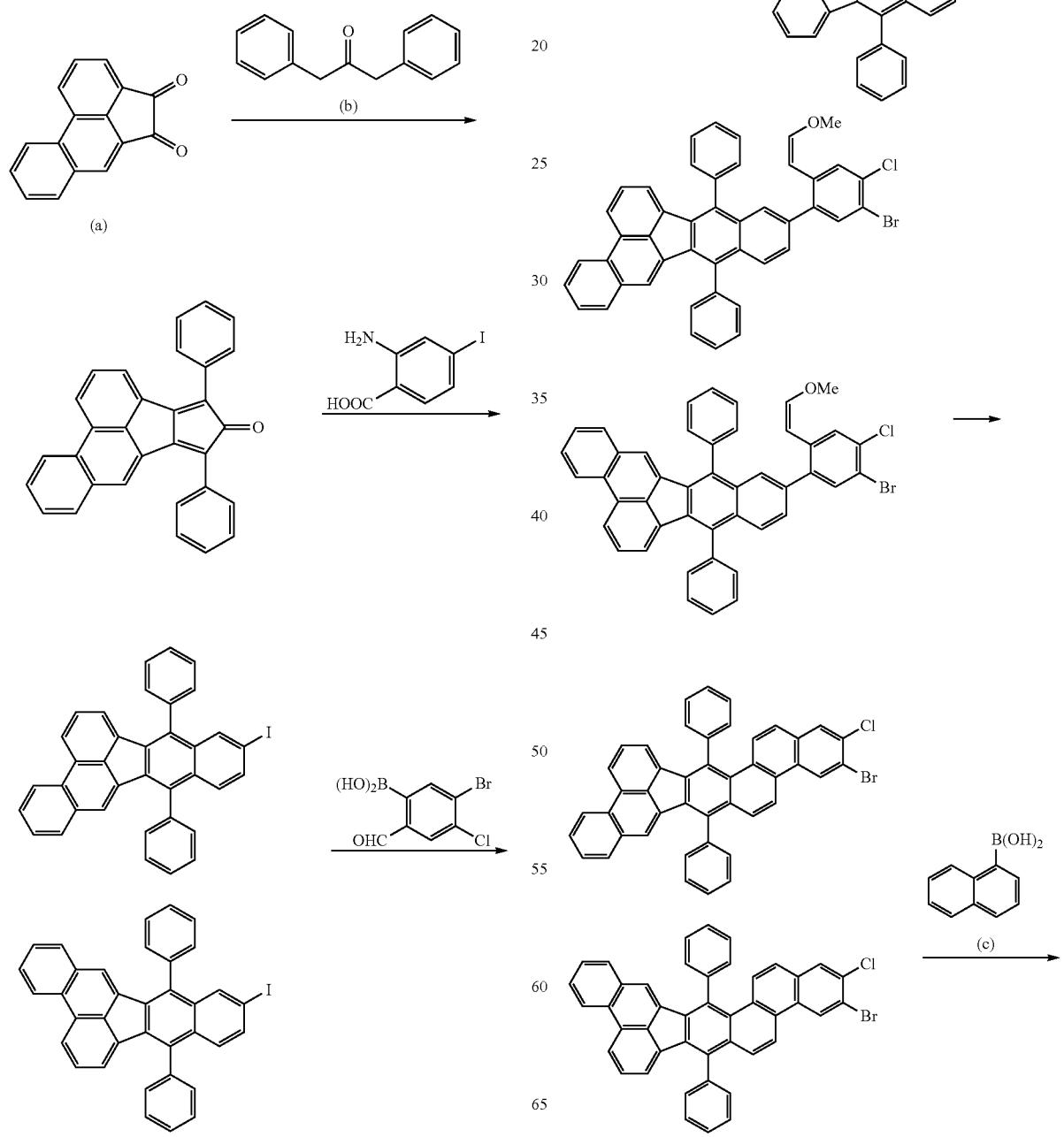

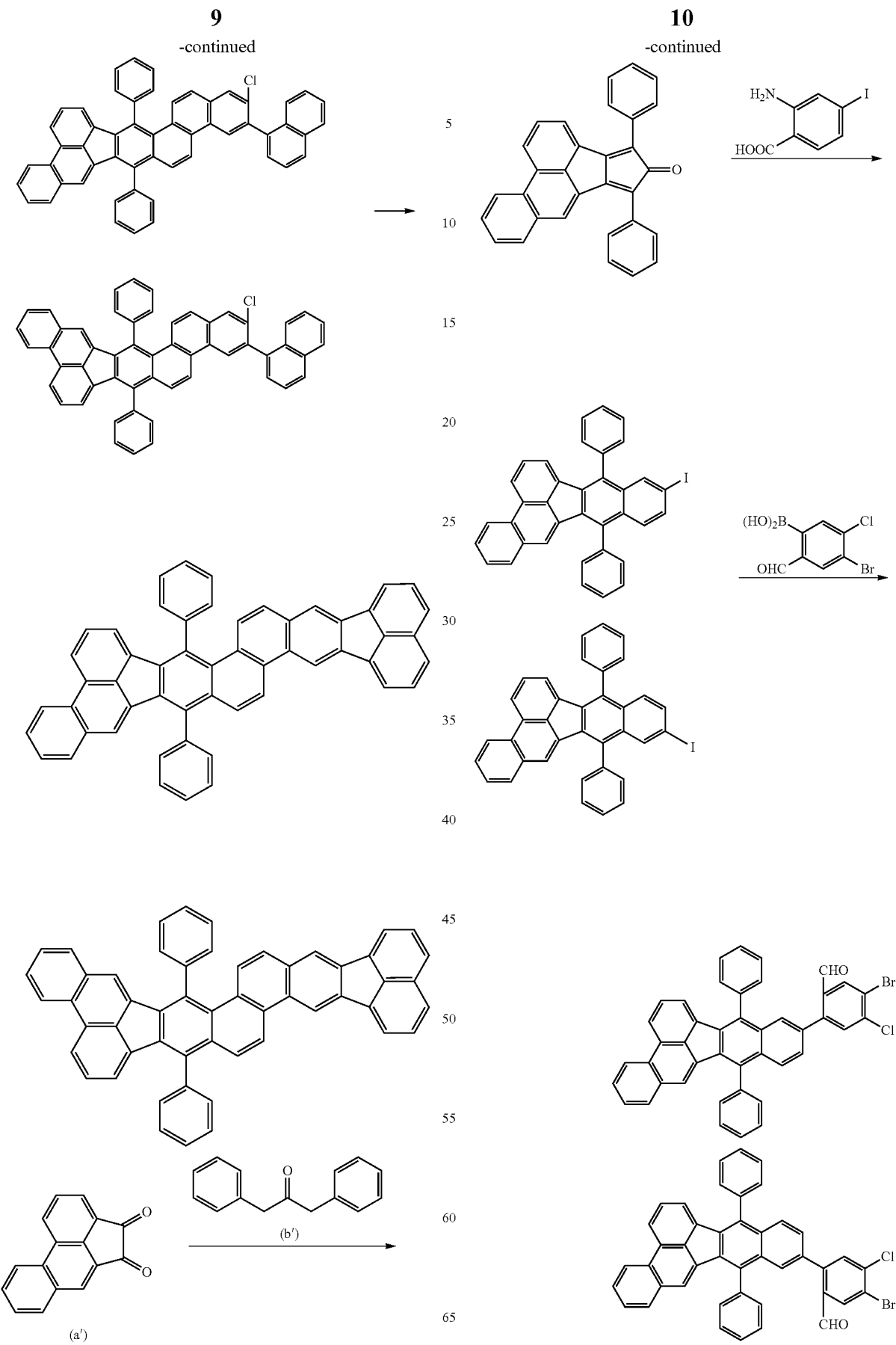

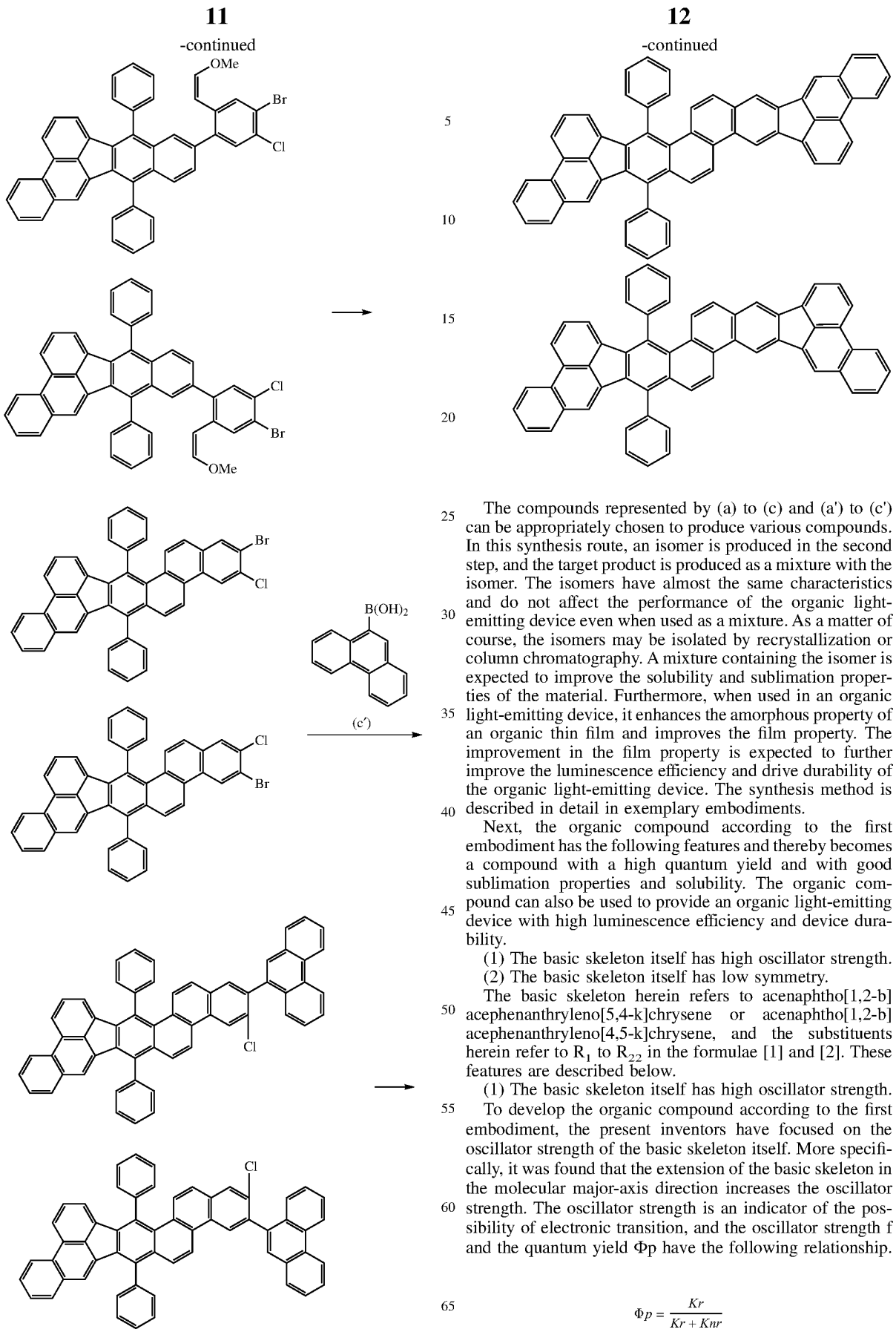

The compounds represented by (a) to (c) and (a') to (c') can be appropriately chosen to produce various compounds. In this synthesis route, an isomer is produced in the second step, and the target product is produced as a mixture with the isomer. The isomers have almost the same characteristics and do not affect the performance of the organic light-emitting device even when used as a mixture. As a matter of course, the isomers may be isolated by recrystallization or column chromatography. A mixture containing the isomer is expected to improve the solubility and sublimation properties of the material. Furthermore, when used in an organic light-emitting device, it enhances the amorphous property of an organic thin film and improves the film property. The improvement in the film property is expected to further improve the luminescence efficiency and drive durability of the organic light-emitting device. The synthesis method is described in detail in exemplary embodiments.

Next, the organic compound according to the first embodiment has the following features and thereby becomes a compound with a high quantum yield and with good sublimation properties and solubility. The organic compound can also be used to provide an organic light-emitting device with high luminescence efficiency and device durability.

(1) The basic skeleton itself has high oscillator strength.
(2) The basic skeleton itself has low symmetry.

The basic skeleton herein refers to acenaphtho[1,2-b]acephenanthryleno[5,4-k]chrysene or acenaphtho[1,2-b]acephenanthryleno[4,5-k]chrysene, and the substituents herein refer to $R_1$ to $R_{22}$ in the formulae [1] and [2]. These features are described below.

(1) The basic skeleton itself has high oscillator strength.

To develop the organic compound according to the first embodiment, the present inventors have focused on the oscillator strength of the basic skeleton itself. More specifically, it was found that the extension of the basic skeleton in the molecular major-axis direction increases the oscillator strength. The oscillator strength is an indicator of the possibility of electronic transition, and the oscillator strength f and the quantum yield Φp have the following relationship.

$$\Phi p = \frac{Kr}{Kr + Knr}$$

-continued $$Kr = \frac{2\pi e^2}{\varepsilon_0^4 c E} f$$

Φp: quantum yield
Kr: rate constant of light emission process
Knr: rate constant of non-emission process
f: oscillator strength
$\varepsilon_0$: permittivity of free space
c: speed of light in vacuum
e: elementary charge Table 1 shows a comparison of the oscillator strength between the basic skeleton of the first embodiment and diacenaphtho[1,2-b:1',2'-k]chrysene, which is a basic skeleton of a compound described in Patent Literature 1.

TABLE 1

| Name | Structure | Oscillator strength |
|---|---|---|
| Acenaphtho[1,2-b]acephenanthryleno[4,5-k]chrysene | 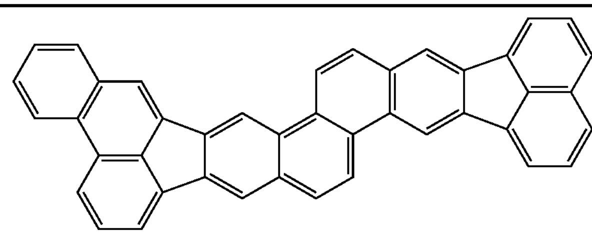 | 0.57 |
| Diacenaphtho[1,2-b:1',2'-k]chrysene | 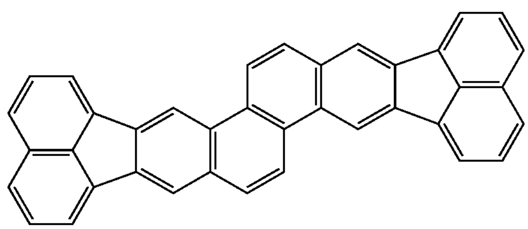 [SMILES: c1cc2c3c(cccc3c1)-c1cc3c(ccc4c5cc6c(cc5ccc34)-c3cccc4cccc-6c34)cc1-2] | 0.51 |

The oscillator strength was calculated using the following molecular orbital calculation. The density functional theory (DFT) was used for the calculation technique of the molecular orbital calculation method. B3LYP was used as the functional, and 6-31G* was used as the basis function. The molecular orbital calculation was performed using widely used Gaussian 09 (Gaussian 09, Revision C. 01, M. J. Frisch, G. W. Trucks, H. B. Schlegel, G. E. Scuseria, M. A. Robb, J. R. Cheeseman, G. Scalmani, V Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford CT, 2010). The molecular orbital calculation in the specification of the present disclosure is performed by this method.

Table 1 shows that the basic skeleton of the first embodiment has a higher oscillator strength than the basic skeleton of the prior literature. The oscillator strength is probably increased due to the same direction of the transition dipole moment as the molecular major-axis direction.

Next, the quantum yield of the organic compound according to the first embodiment is described in comparison with a comparative compound with a structure similar to the structure of the organic compound according to the first embodiment. The comparative compound is a comparative compound (1) in Table 2. The comparative compound (1) is a compound with the same basic skeleton (diacenaphtho[1,2-b:1',2'-k]chrysene skeleton) as the compound 1-A described in Patent Literature 1. One organic compound according to the first embodiment is an exemplary compound A17. The exemplary compound A17 is a compound in which $R_2$ and $R_{12}$ in the formula [2] denote a benzene ring and $R_1$, $R_3$ to Ru, and $R_{13}$ to $R_{22}$ denote a hydrogen atom.

Table 2 shows the measurement results of an emission spectrum of a toluene solution of each compound at $1 \times 10^{-5}$ mol/l. The measurement was performed by measuring photoluminescence with F-4500 manufactured by Hitachi, Ltd. at room temperature and at an excitation wavelength of 350 nm. Table 2 also shows the absolute quantum yield of each compound in solution at room temperature measured with an absolute PL quantum yield measurement system (C9920-02) manufactured by Hamamatsu Photonics K.K. The quantum yield is a relative value with respect to the quantum yield (1.00) of a solution of the exemplary compound A17.

TABLE 2

| Compound | Structure | Emission wavelength max | Quantum yield |
|---|---|---|---|
| Comparative compound (1) | 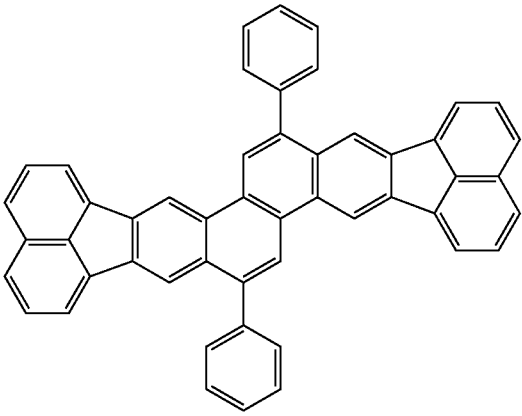 [SMILES: c1ccc(-c2cc3c4cc5c(cc4c(-c4ccccc4)cc3c3cc4c(cc23)-c2cccc3cccc-4c23)-c2cccc3cccc-5c23)cc1] | 449 | 0.95 |
| Exemplary compound A17 | 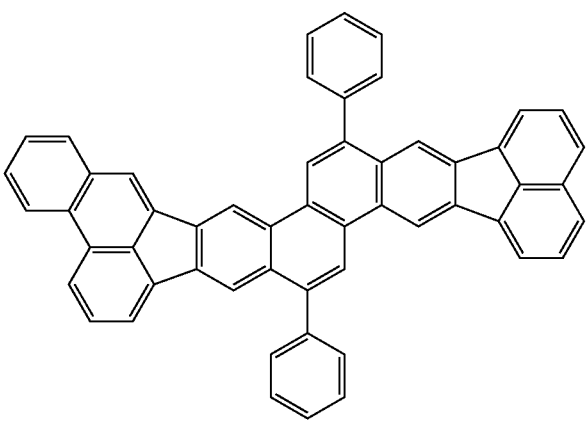 [SMILES: c1ccc(-c2cc3c4cc5c(cc4c(-c4ccccc4)cc3c3cc4c(cc23)-c2cccc3cccc-4c23)-c2cccc3c2c-5cc2ccccc23)cc1] | 449 | 1.00 |

Table 2 shows that the comparative compound (1) has a quantum yield of 0.95, whereas the exemplary compound A17 has a higher quantum yield of 1.00. This is probably because the compound of the first embodiment has a longer molecular structure in the molecular major-axis direction and a higher oscillator strength than the comparative compound (1). That is, the exemplary compound of the first embodiment has better emission properties.

Thus, the compound of the first embodiment has a high quantum yield because the basic skeleton itself has high oscillator strength. An organic light-emitting device including this compound has high luminescence efficiency and good emission properties.

The exemplary compound A17 and the comparative compound (1) have the same maximum emission wavelength (λmax). In polycyclic aromatics, expansion of a condensed portion typically results in a longer emission wavelength. Although the fused-ring structure of the exemplary compound A17 was expanded relative to the comparative compound (1), the emission wavelength was comparable. This result is described later.

(2) The basic skeleton itself has low symmetry.

Polycyclic aromatic hydrocarbons typically have high molecular planarity and enhanced molecular packing. Molecular packing undesirably increases crystallinity, impairs sublimation properties and solubility, and causes concentration quenching. In other words, molecular packing can be suppressed to improve sublimation properties and solubility and suppress concentration quenching. The improvement in sublimation properties enables a material to be purified by sublimation purification and an organic light-emitting device to be produced by vapor deposition. The improvement in solubility also enables a material to be purified by recrystallization or column purification. Thus, the sublimation properties and solubility can be improved to purify a material and to decrease impurities in the organic light-emitting device. This can prevent a decrease in luminescence efficiency or drive durability due to impurities in the organic light-emitting device. The concentration quenching can also be suppressed to improve the luminescence efficiency of the organic light-emitting device.

The present inventors have therefore focused on the molecular structure of the basic skeleton. The symmetry of the basic skeleton itself can be decreased to suppress molecular packing.

Figure 8:
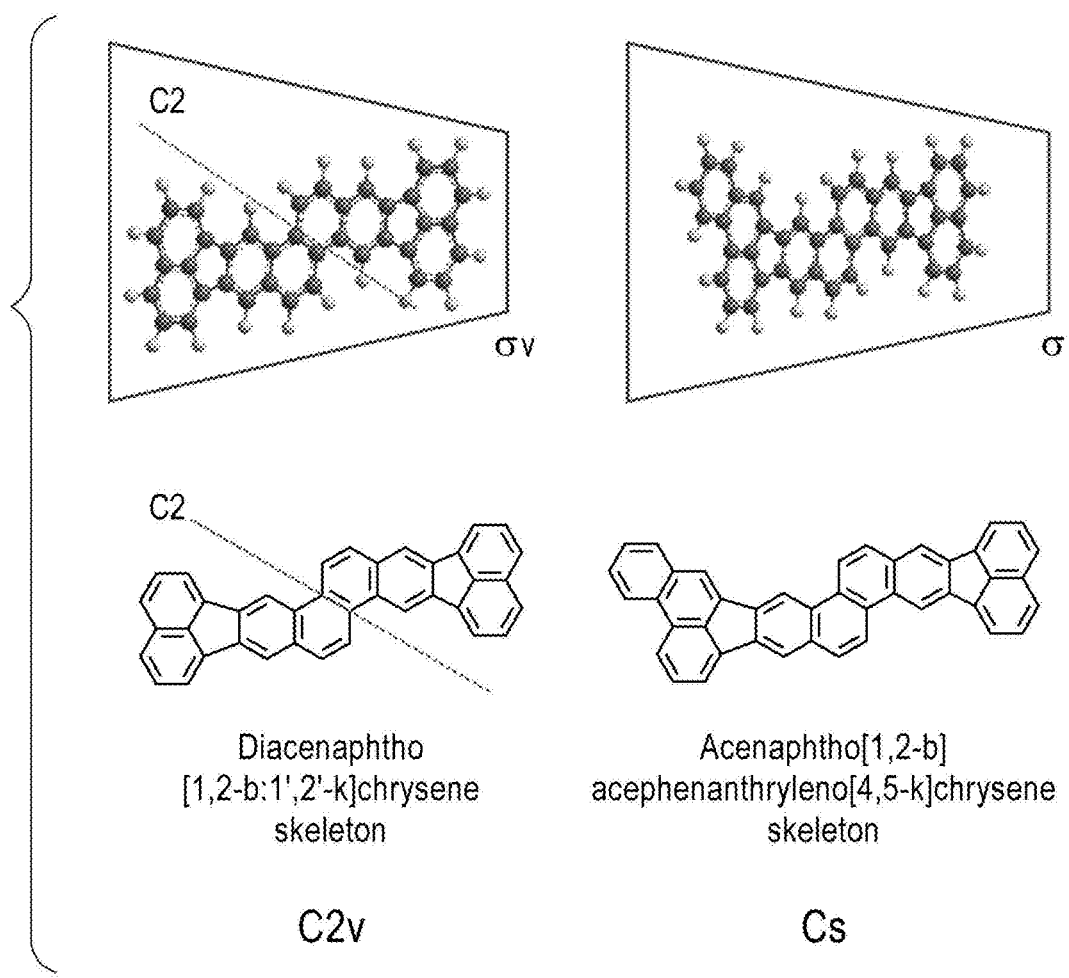
FIG. 8 are schematic views of a diacenaphtho[1,2-b:1',2'-k]chrysene skeleton and an acenaphtho[1,2-b]acephenanthryleno[4,5-k]chrysene skeleton.

The basic skeleton of the compound of the first embodiment is an acenaphtho[1,2-b]acephenanthryleno[5,4-k]chrysene skeleton or an acenaphtho[1,2-b]acephenanthryleno[4,5-k]chrysene skeleton (FIG. 8). These skeletons do not have an axis of rotation, have a symmetry plane (σ) including a molecular plane, and are therefore classified as the point group Cs. On the other hand, the diacenaphtho[1,2-b:1',2'-k]chrysene skeleton in Patent Literature 1 has a two-fold axis (C2) in the oblique direction of the molecular plane, has a symmetry plane (σv) including the two-fold axis, and is therefore classified as the point group C2v.

Thus, the acenaphtho[1,2-b]acephenanthryleno[4,5-k]chrysene skeleton of the first embodiment has lower molecular symmetry than the diacenaphtho[1,2-b:1',2'-k]chrysene skeleton described in Patent Literature 1. Thus, the basic skeleton of the first embodiment itself has low symmetry, and the organic compound according to the first embodiment is a molecule with low symmetry.

weight loss reaches 5% in TG/DTA measurement. Table 3 shows the results of a toluene solubility test in which the amount of toluene required to dissolve 100 mg of each compound is compared. In the toluene solubility test performed in a nitrogen atmosphere under reflux by heating while stirring, dissolution was visually inspected and was expressed as a relative value with respect to the amount of toluene (1.0) used to completely dissolve the exemplary compound A1.

TABLE 3

| Compound | Structure | Molecular weight | Solubility | Decomposition temperature-sublimation temperature (° C.) |
|---|---|---|---|---|
| Comparative compound (2) | *(chemical structure)* | 628.77 | 1.1 | 70 |
| Exemplary compound A1 | *(chemical structure)* | 678.83 | 1.0 | 90 |

In molecules with low symmetry, as compared with molecules with high symmetry, the molecular arrangement in a solid tends to be disordered, and molecular packing in which molecules overlap regularly is suppressed. A compound with suppressed molecular packing has improved sublimation properties and solubility. Furthermore, association between molecules can be prevented to suppress concentration quenching.

The effect of asymmetry of the basic skeleton is compared between a comparative compound (2) and an exemplary compound A1. The comparative compound (2) is a compound with the same basic skeleton (diacenaphtho[1,2-b:1', 2'-k]chrysene skeleton) as the compound 1-A described in Patent Literature 1.

Table 3 shows the temperature difference between the decomposition temperature and the sublimation temperature of each compound. The sublimation temperature is a temperature at which a sufficient sublimation rate is achieved after the temperature is slowly increased in a vacuum of $1 \times 10^{-1}$ Pa in an Ar flow to start sublimation purification. The decomposition temperature is a temperature at which the Table 3 shows that the exemplary compound A1 has a larger temperature difference between the decomposition temperature and the sublimation temperature than the comparative compound (2). A larger temperature difference between the decomposition temperature and the sublimation temperature results in a larger temperature margin in sublimation purification and therefore better sublimation properties. Furthermore, the exemplary compound A1 can be dissolved in a smaller amount of solvent and has higher solubility than the comparative compound (2).

In general, a higher molecular weight results in poorer sublimation properties and lower solubility. In spite of its higher molecular weight, however, the exemplary compound A1 has better sublimation properties and solubility than the comparative compound (2). This is probably because the basic skeleton itself has low symmetry, and molecular packing is suppressed.

Thus, due to the suppressed molecular packing, the compound of the first embodiment has good sublimation properties and can be purified by sublimation without decomposition. Furthermore, a material with higher solubility can be more easily purified by a purification technique in which higher solubility is desired, for example, by column purification. Thus, an organic light-emitting device including such a material has high drive durability.

Thus, the organic compound according to the first embodiment has the features of the conditions (1) and (2) and has a high quantum yield, good sublimation properties, and high solubility.

A structure in which one side of a benzene ring of the diacenaphtho[1,2-b:1',2'-k]chrysene skeleton in Patent Literature 1 is fused to decrease the symmetry other than the acenaphtho[1,2-b]acephenanthryleno[5,4-k]chrysene skeleton and the acenaphtho[1,2-b]acephenanthryleno[4,5-k]chrysene skeleton, which are the basic skeletons of the first embodiment, may be a structural isomer. Thus, molecular orbital calculations of structural isomers were performed. Table 4 shows the results.

The blue-light-emitting material can have darker blue chromaticity, that is, a shorter emission wavelength, to expand the color reproduction range.

On the other hand, the basic skeleton of the compound of the first embodiment has the same S1 as diacenaphtho[1,2-b:1',2'-k]chrysene in spite of the expansion of the fused ring. Furthermore, the basic skeleton itself has an emission wavelength in the blue emission region, and the compound of the first embodiment can be used as a blue-light-emitting material. As a matter of course, the compound of the first embodiment can have an appropriate substituent and can be used as a green- or red-light-emitting material.

Thus, the organic compound according to the first embodiment has a high quantum yield, good sublimation properties, and high solubility. The organic compound according to the first embodiment can be widely used as a light-emitting material from a blue region to a red region. In

TABLE 4

| | Structure | $S_1$ |
|---|---|---|
| Basic skeleton of formula [1] | 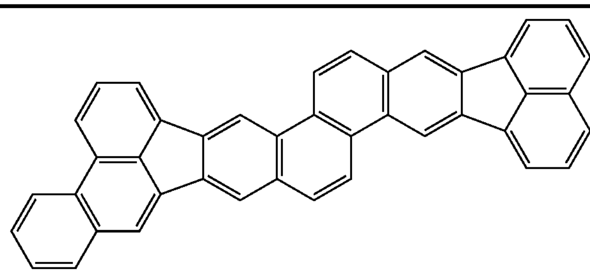 | 428 nm |
| Compound 1-A | 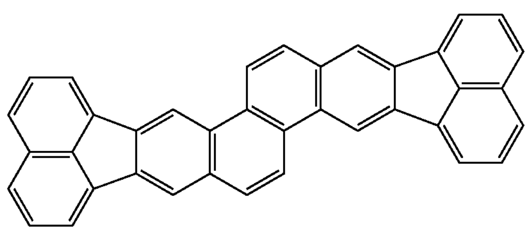 [SMILES: c1cc2c3c(cccc3c1)-c1cc3c(ccc4c5cc6c(cc5ccc34)-c3cccc4cccc-6c34)cc1-2] | 428 nm |
| Comparative compound (3) | 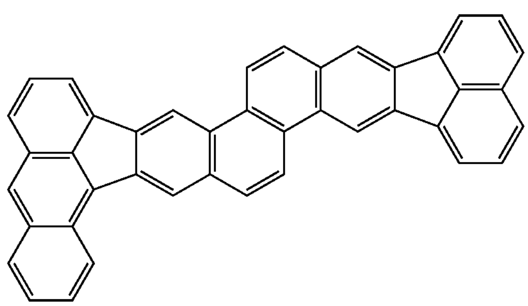 [SMILES: c1ccc2c3c4c(cccc4cc2c1)-c1cc2c(ccc4c5cc6c(cc5ccc24)-c2cccc4cccc-6c24)cc1-3] | 484 nm |

The basic skeleton of the formula [1] has a structure in which a benzene ring is fused at the 2- and 3-positions of diacenaphtho[1,2-b:1',2'-k]chrysene. On the other hand, the comparative compound (3) has a structure in which a benzene ring is fused at the 1- and 2-positions of diacenaphtho[1,2-b:1',2'-k]chrysene.

Table 4 shows that the comparative compound (3) has a higher singlet excited state (S1) than diacenaphtho[1,2-b:1', 2'-k]chrysene. In other words, the emission wavelength becomes longer. Thus, the comparative compound (3) has no emission wavelength in a blue emission region (420 to 480 nm) and cannot be used as a blue-light-emitting material.

particular, the organic compound according to the first embodiment can be used as a light-emitting material in a dark blue region.

Furthermore, the organic compound can satisfy the following condition (3).

(3) Having a bulky substituent at the substitution position where the basic skeleton and the substituent have a large dihedral angle This is because satisfying the condition (3) increases the dihedral angle between the basic skeleton and the substituent and can further suppress molecular packing. Furthermore, when at least one substituent is a group other than a hydrogen atom, such as a bulky group, molecular packing in which basic skeletons overlap is suppressed. For the formula [1], for example, the dihedral angle was estimated using molecular orbital calculation. Table 5 shows the results.
TABLE 5
| | Structure | Dihedral angle |
|---|---|---|
| 1-phenyl | 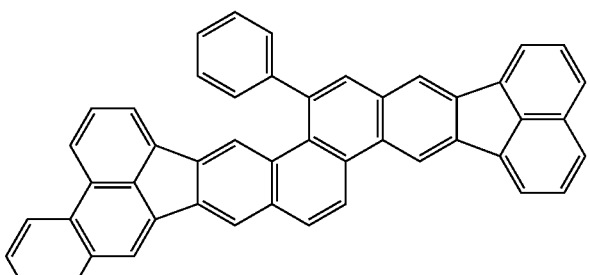 | 58° |
| 2-phenyl | 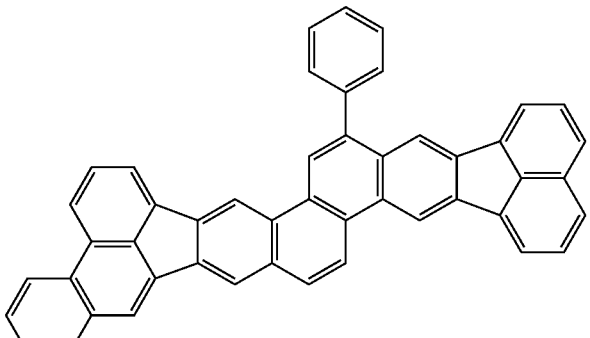 | 59° |
| 3-phenyl | 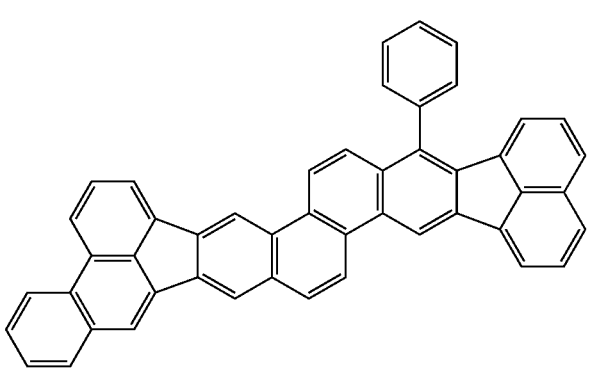 [SMILES: c1ccc(-c2c3c(cc4c2ccc2c5cc6c(cc5ccc42)-c2cc4ccccc4c4cccc-6c24)-c2cccc4cccc-3c24)cc1] | 90° |
| 4-phenyl | 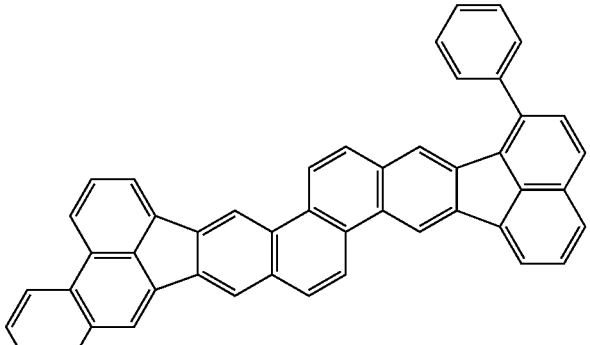 | 53° |

TABLE 5-continued
| Structure | Dihedral angle |
|---|---|
| 5-phenyl 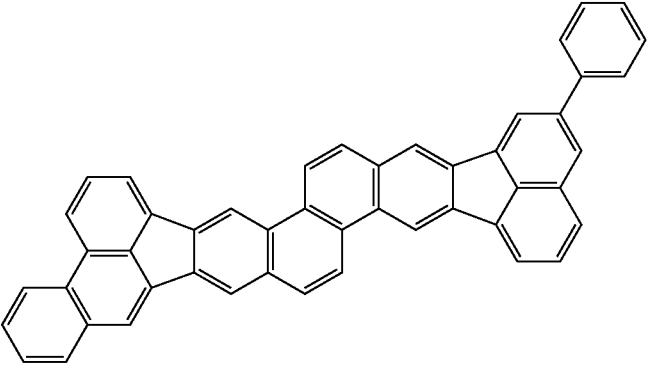 [SMILES: c1ccc(-c2cc3c4c(cccc4c2)-c2cc4c(ccc5c6cc7c(cc6ccc45)-c4cc5ccccc5c5cccc-7c45)cc2-3)cc1] | 39° |
| 6-phenyl 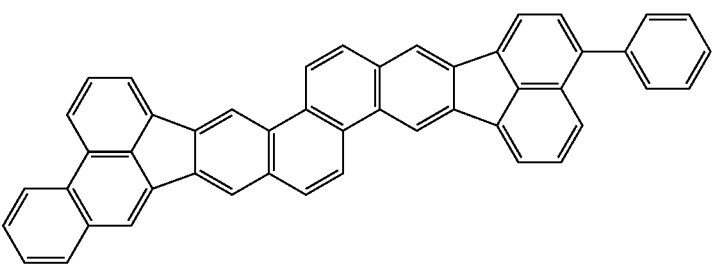 [SMILES: c1ccc(-c2ccc3c4c(cccc24)-c2cc4c(ccc5c6cc7c(cc6ccc45)-c4cc5ccccc5c5cccc-7c45)cc2-3)cc1] | 50° |
| 7-phenyl 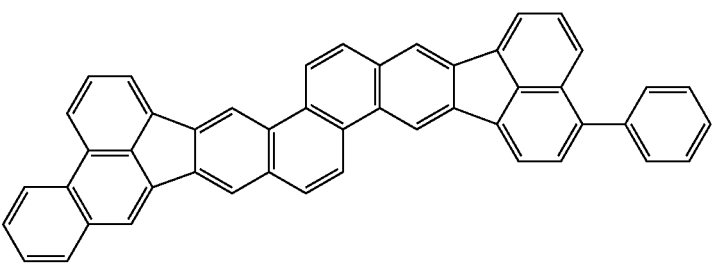 [SMILES: c1ccc(-c2ccc3c4c(cccc24)-c2cc4ccc5c6cc7c(cc6ccc5c4cc2-3)-c2cc3ccccc3c3cccc-7c23)cc1] | 52° |
| 8-phenyl 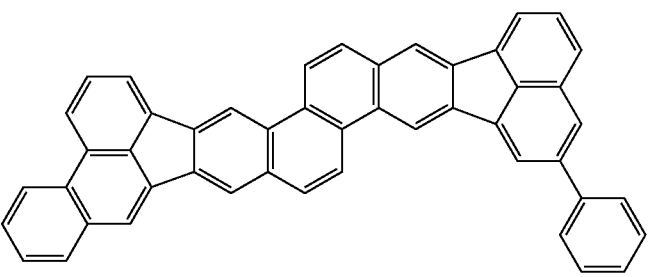 [SMILES: c1ccc(-c2cc3c4c(cccc4c2)-c2cc4ccc5c6cc7c(cc6ccc5c4cc2-3)-c2cc3ccccc3c3cccc-7c23)cc1] | 40° |
| 9-phenyl 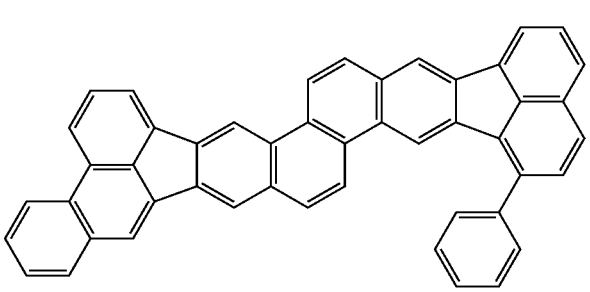 [SMILES: c1ccc(-c2ccc3cccc4c3c2-c2cc3c(ccc5c6cc7c(cc6ccc35)-c3cc5ccccc5c5cccc-7c35)cc2-4)cc1] | 54° |

TABLE 5-continued
| Structure | Dihedral angle |
|---|---|
| 10-phenyl 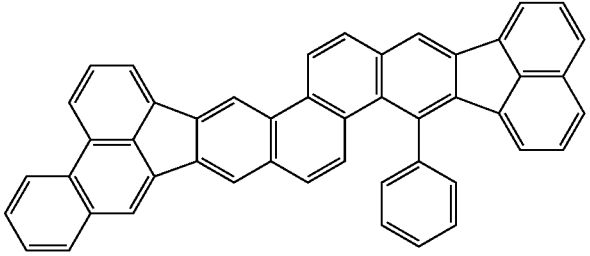 [SMILES: c1ccc(-c2c3c(cc4ccc5c6cc7c(cc6ccc5c24)-c2cc4ccccc4c4cccc-7c24)-c2cccc4cccc-3c24)cc1] | 80° |
| 11-phenyl 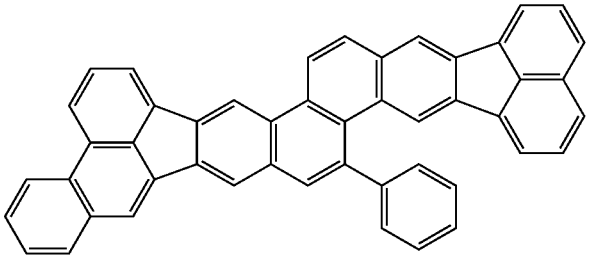 [SMILES: c1ccc(-c2cc3cc4c(cc3c3ccc5cc6c(cc5c23)-c2cccc3cccc-6c23)-c2cccc3c2c-4cc2ccccc23)cc1] | 58° |
| 12-phenyl 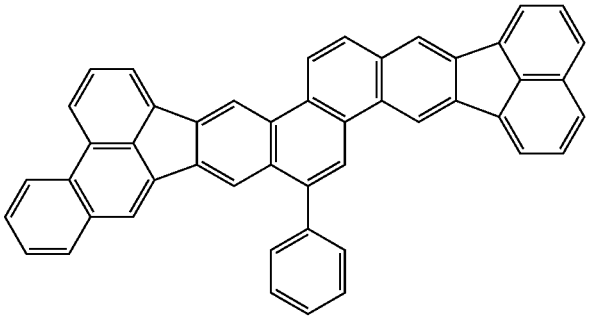 [SMILES: c1ccc(-c2cc3c4cc5c(cc4ccc3c3cc4c(cc23)-c2cc3ccccc3c3cccc-4c23)-c2cccc3cccc-5c23)cc1] | 59° |
| 13-phenyl 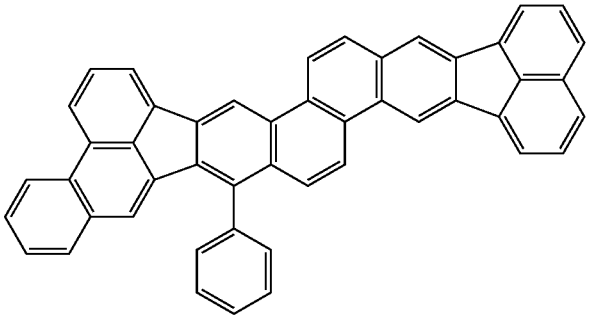 [SMILES: c1ccc(-c2c3c(cc4c2ccc2c5cc6c(cc5ccc42)-c2cccc4cccc-6c24)-c2cccc4c2c-3cc2ccccc24)cc1] | 90° |
| 14-phenyl 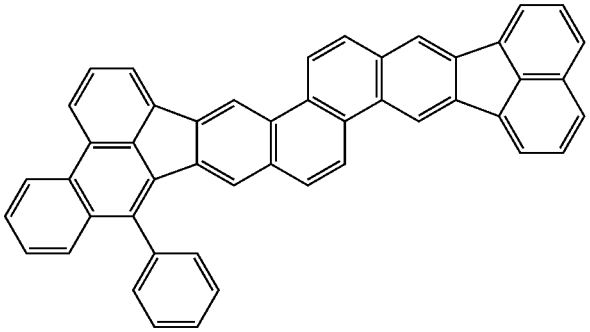 [SMILES: c1ccc(-c2c3c4c(cccc4c4ccccc24)-c2cc4c(ccc5c6cc7c(cc6ccc45)-c4cccc5cccc-7c45)cc2-3)cc1] | 88° |

TABLE 5-continued
| | Structure | Dihedral angle |
|---|---|---|
| 15-phenyl | 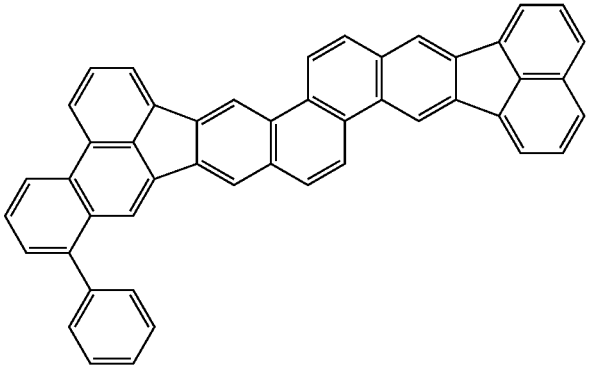 [SMILES: c1ccc(-c2cccc3c2cc2c4c(cccc43)-c3cc4c(ccc5c6cc7c(cc6ccc45)-c4cccc5cccc-7c45)cc3-2)cc1] | 59° |
| 16-phenyl | 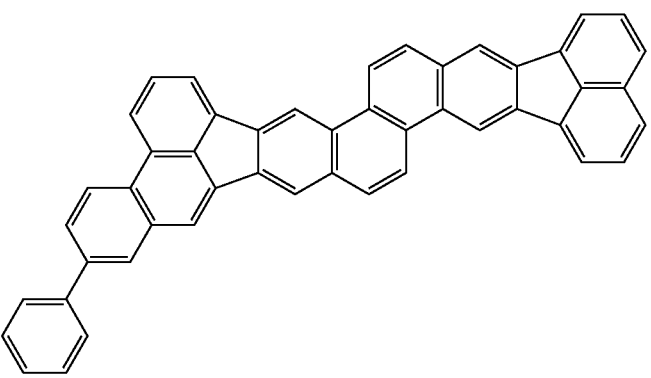 [SMILES: c1ccc(-c2ccc3c(c2)cc2c4c(cccc43)-c3cc4c(ccc5c6cc7c(cc6ccc45)-c4cccc5cccc-7c45)cc3-2)cc1] | 37° |
| 17-phenyl | 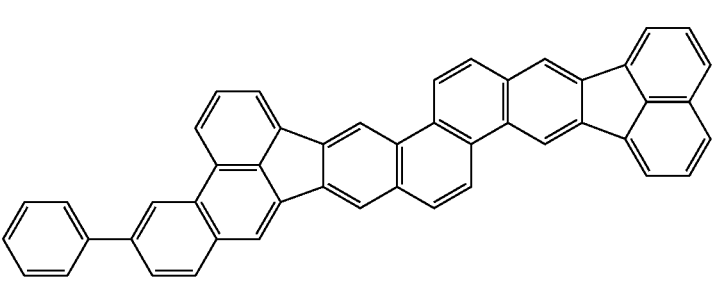 [SMILES: c1ccc(-c2ccc3cc4c5c(cccc5c3c2)-c2cc3c(ccc5c6cc7c(cc6ccc35)-c3cccc5cccc-7c35)cc2-4)cc1] | 37° |
| 18-phenyl | 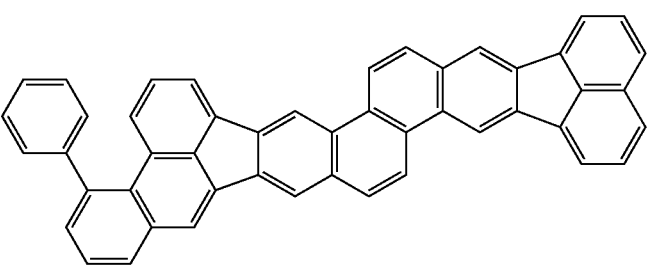 [SMILES: c1ccc(-c2cccc3cc4c5c(cccc5c23)-c2cc3c(ccc5c6cc7c(cc6ccc35)-c3cccc5cccc-7c35)cc2-4)cc1] | 70° |
| 19-phenyl | 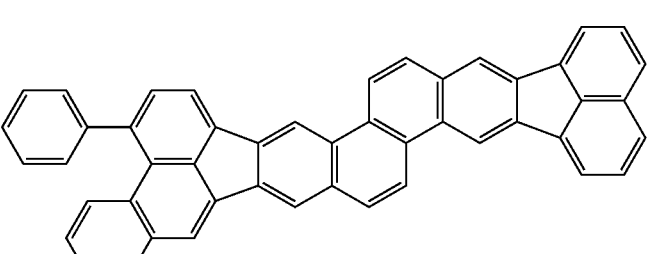 | 69° |

TABLE 5-continued

| | Structure | Dihedral angle |
|---|---|---|
| 20-phenyl | 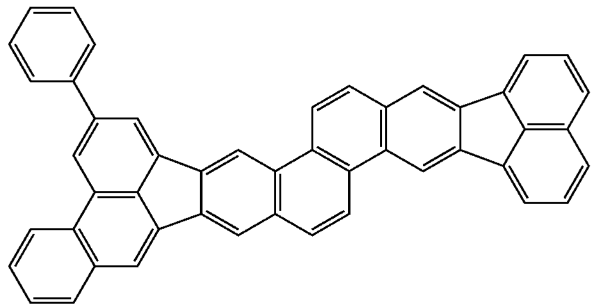 [SMILES: c1ccc(-c2cc3c4c(cc5ccccc5c4c2)-c2cc4ccc5c6cc7c(cc6ccc5c4cc2-3)-c2cccc3cccc-7c23)cc1] | 40° |
| 21-phenyl | 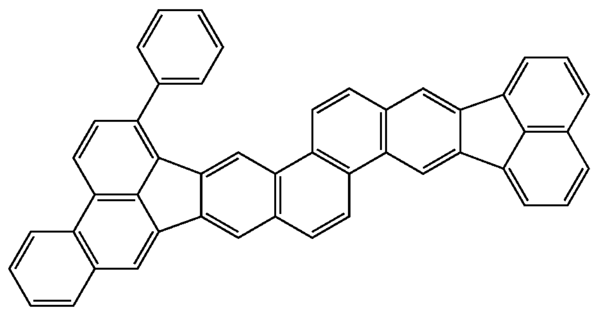 [SMILES: c1ccc(-c2ccc3c4c(cc5ccccc53)-c3cc5ccc6c7cc8c(cc7ccc6c5cc3-c24)-c2cccc3cccc-8c23)cc1] | 55° |
| 22-phenyl | 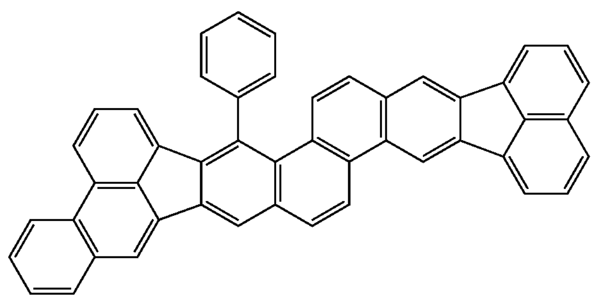 [SMILES: c1ccc(-c2c3c(cc4ccc5c6cc7c(cc6ccc5c24)-c2cccc4cccc-7c24)-c2cc4ccccc4c4cccc-3c24)cc1] | 80° |

Table 5 shows that $R_1$ to $R_3$, $R_{10}$ to $R_{15}$, $R_{18}$ and $R_{19}$, and $R_{22}$ in the formula [1] have a dihedral angle of 58 degrees or more. Due to their sufficiently large dihedral angles, the substituents (phenyl groups) can reduce π-π interaction between the basic skeletons. Thus, the material can have high solubility and good sublimation properties. The use as a light-emitting material of an organic light-emitting device can suppress concentration quenching and an increase in emission wavelength.

The substitution positions can be $R_1$ to $R_3$, $R_{10}$ to $R_{13}$, and $R_{22}$, or $R_2$ and $R_3$, $R_{10}$, $R_{12}$ and $R_{13}$, and $R_{22}$. This is because these substitution positions are the substitution positions of the chrysene moiety at the center of the molecule of the basic skeleton and can more effectively suppress molecular packing.

Next, the organic compound according to the second embodiment has the following features and has a high quantum yield. The organic compound can also be used to provide an organic light-emitting device with high luminescence efficiency.

(4) The basic skeleton itself has high oscillator strength.

The basic skeleton is diacephenanthryleno[5,4-b:5',4'-k]chrysene in the formula [3], diacephenanthryleno[4,5-b:5', 4'-k]chrysene in the formula [4], or diacephenanthryleno[4,5-b:4',5'-k]chrysene in the formula [5], and the substituents are $R_1$ to $R_{26}$ in the formulae [3] to [5]. This feature is described below.

(4) The basic skeleton itself has high oscillator strength.

To develop the organic compound according to the second embodiment, the present inventors have focused on the oscillator strength of the basic skeleton itself. More specifically, it was found that the extension of the basic skeleton in the molecular major-axis direction increases the oscillator strength. The oscillator strength is described in the section "(1) The basic skeleton itself has high oscillator strength".

Table 6 shows a comparison of the oscillator strength between the basic skeleton of the second embodiment and diacenaphtho[1,2-b:1',2'-k]chrysene, which is a basic skeleton of a compound described in Patent Literature 1. The oscillator strength is calculated as described in the section "(1) The basic skeleton itself has high oscillator strength".

TABLE 6

| Name | Structure | Oscillator strength |
| --- | --- | --- |
| Diacephenanthryleno [5,4-b:5',4'-k] chrysene | 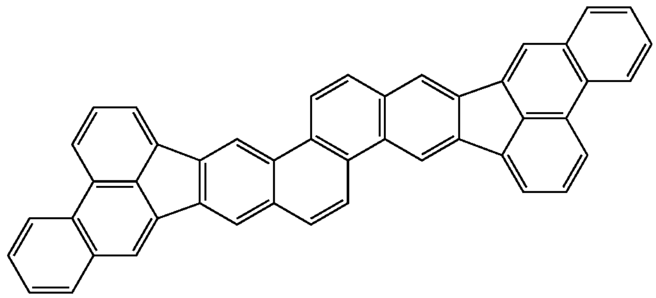 [SMILES: c1ccc2c(c1)cc1c3c(cccc32)-c2cc3c(ccc4c5cc6c(cc5ccc34)-c3cc4ccccc4c4cccc-6c34)cc2-1] | 0.54 |
| Diacephenanthryleno [4,5-b:5',4'-k] chrysene | 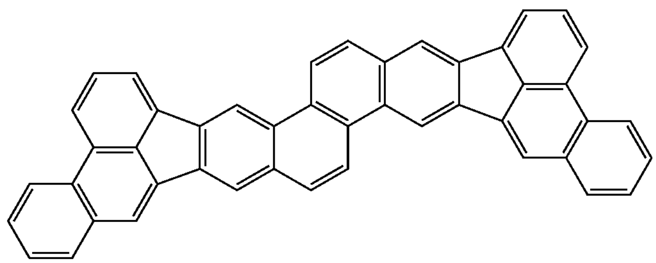 [SMILES: c1ccc2c(c1)cc1c3c(cccc32)-c2cc3c(ccc4c5cc6c(cc5ccc34)-c3cccc4c3c-6cc3ccccc34)cc2-1] | 0.58 |
| Diacephenanthryleno [4,5-b:4',5'-k] chrysene | 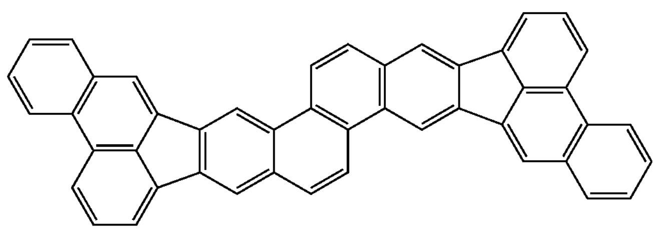 [SMILES: c1ccc2c(c1)cc1c3c(cccc32)-c2cc3ccc4c5cc6c(cc5ccc4c3cc2-1)-c1cccc2c1c-6cc1ccccc12] | 0.63 |
| Diacenaphtho [1,2-b:1',2'-k] chrysene | 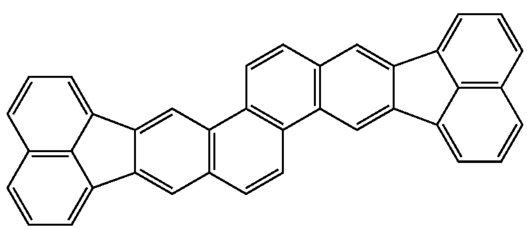 [SMILES: c1cc2c3c(cccc3c1)-c1cc3c(ccc4c5cc6c(cc5ccc34)-c3cccc4cccc-6c34)cc1-2] | 0.51 |

Table 6 shows that the basic skeleton of the second embodiment has a higher oscillator strength than the basic skeleton of the prior literature. The oscillator strength is probably increased due to the same direction of the transition dipole moment as the molecular major-axis direction.

Next, the quantum yield of the organic compound according to the second embodiment is described in comparison with a comparative compound with a structure similar to the structure of the organic compound according to the second embodiment. The comparative compound is a comparative compound (1) in Table 7. The comparative compound (1) is a compound with the same basic skeleton (diacenaphtho[1,2-b:1',2'-k]chrysene skeleton) as the compound 1-A described in Patent Literature 1. One organic compound according to the second embodiment is an exemplary compound D2. The exemplary compound D2 is a compound in which $R_2$ and $R_{12}$ in the formula [3] denote a benzene ring having a methyl group as a substituent and $R_1$, $R_3$ and $R_4$, $R_7$ and Ru, and $R_{13}$ and $R_{26}$ denote a hydrogen atom.

Table 7 shows the results of the photoluminescence measurement of an emission spectrum of a toluene solution of each compound at $1\times10^{-5}$ mol/l at room temperature measured with F-4500 manufactured by Hitachi, Ltd. at an excitation wavelength of 350 nm. Table 7 also shows the absolute quantum yield of each compound in solution at room temperature measured with an absolute PL quantum yield measurement system (C9920-02) manufactured by Hamamatsu Photonics K.K. The quantum yield is a relative value with respect to the quantum yield (1.00) of a solution of the exemplary compound D2.

TABLE 7

| Compound | Structure | λmax | Quantum yield |
|---|---|---|---|
| Comparative compound (1) | 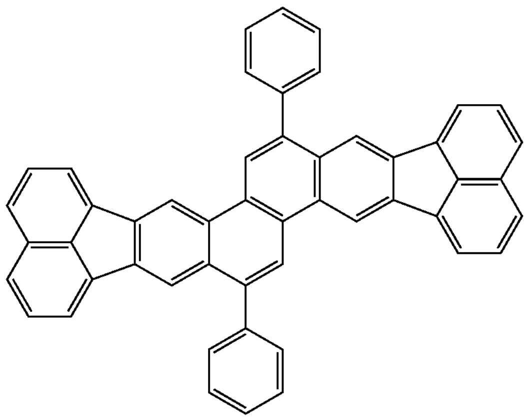 [SMILES: c1ccc(-c2cc3c4cc5c(cc4c(-c4ccccc4)cc3c3cc4c(cc23)-c2cccc3cccc-4c23)-c2cccc3cccc-5c23)cc1] | 449 | 0.95 |
| Exemplary compound D2 | 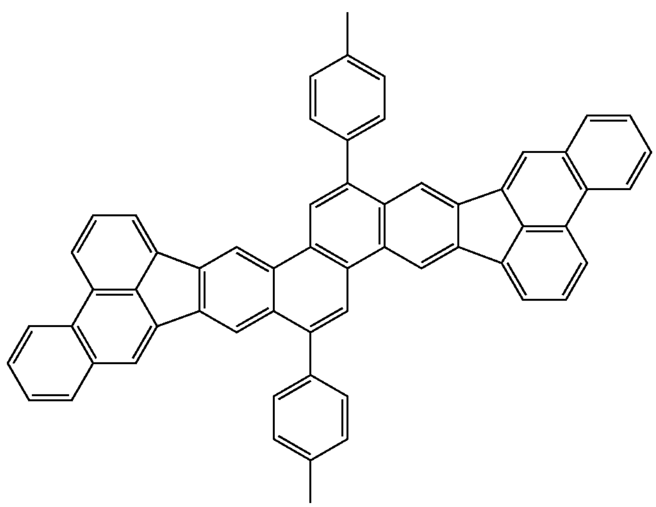 [SMILES: Cc1ccc(-c2cc3c4cc5c(cc4c(-c4ccc(C)cc4)cc3c3cc4c(cc23)-c2cc3ccccc3c3cccc-4c23)-c2cc3ccccc3c3cccc-5c23)cc1] | 453 | 1.00 |

Table 7 shows that the comparative compound (1) has a quantum yield of 0.95, whereas the exemplary compound D2 has a higher quantum yield of 1.00. This is probably because the compound of the second embodiment has a longer molecular structure in the molecular major-axis direction and a higher oscillator strength than the comparative compound (1). That is, the exemplary compound of the second embodiment has better emission properties.

Thus, the compound of the second embodiment has a high quantum yield because the basic skeleton itself has high oscillator strength. An organic light-emitting device including this compound has high luminescence efficiency and good emission properties.

The exemplary compound D2 and the comparative compound (1) have almost the same maximum emission wavelength (λmax). In polycyclic aromatics, expansion of a condensed portion typically results in a longer emission wavelength. Although the fused-ring structure of the exemplary compound D2 was expanded relative to the comparative compound (1), the emission wavelength was comparable. This result is described later.

A structure in which one side of a benzene ring of the diacenaphtho[1,2-b:1',2'-k]chrysene skeleton in Patent Literature 1 is fused other than the diacephenanthryleno[5,4-b:5',4'-k]chrysene skeleton, the diacephenanthryleno[4,5-b:5',4'-k]chrysene skeleton, and the diacephenanthryleno[4,5-b:4',5'-k]chrysene, which are the basic skeletons of the second embodiment, may be a structural isomer. Thus, molecular orbital calculations of structural isomers were performed. Table 8 shows the results.

TABLE 8

| | Structure | $S_1$ |
|---|---|---|
| Basic skeleton of formula [3] | 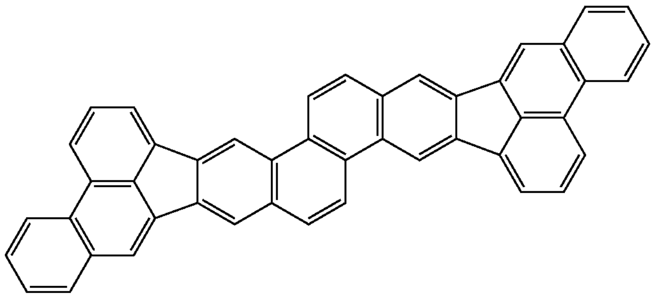 [SMILES: c1ccc2c(c1)cc1c3c(cccc32)-c2cc3c(ccc4c5cc6c(cc5ccc34)-c3cc4ccccc4c4cccc-6c34)cc2-1] | 428 nm |
| Basic skeleton of formula [4] | 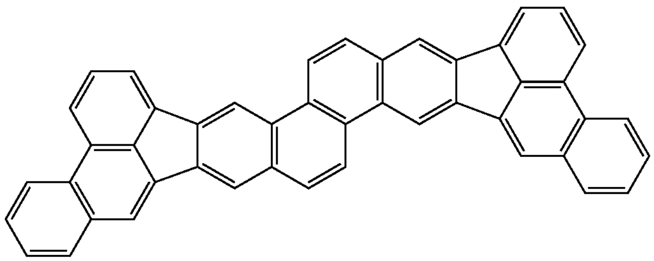 [SMILES: c1ccc2c(c1)cc1c3c(cccc32)-c2cc3c(ccc4c5cc6c(cc5ccc34)-c3cccc4c3c-6cc3ccccc34)cc2-1] | 426 nm |
| Basic skeleton of formula [5] | 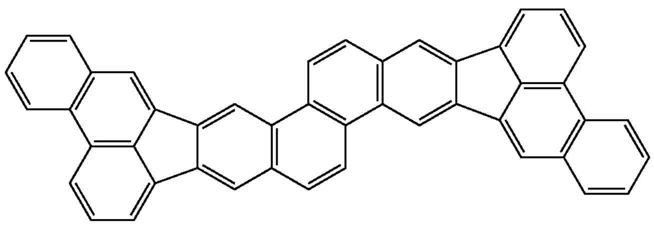 [SMILES: c1ccc2c(c1)cc1c3c(cccc32)-c2cc3ccc4c5cc6c(cc5ccc4c3cc2-1)-c1cccc2c1c-6cc1ccccc12] | 424 nm |
| Compound 1-A | 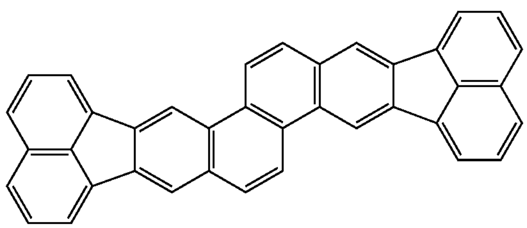 [SMILES: c1cc2c3c(cccc3c1)-c1cc3c(ccc4c5cc6c(cc5ccc34)-c3cccc4cccc-6c34)cc1-2] | 428 nm |
| Comparative compound (4) | 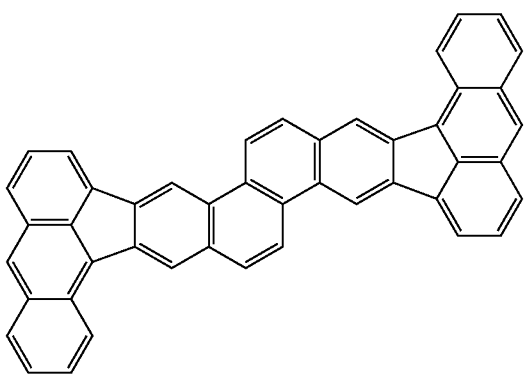 [SMILES: c1ccc2c3c4c(cccc4cc2c1)-c1cc2c(ccc4c5cc6c(cc5ccc24)-c2c4ccccc4cc4cccc-6c24)cc1-3] | 510 nm |

The basic skeleton of the formula [3] has a structure in which a benzene ring is fused at the 2-, 3-, 12-, and 13-positions of diacenaphtho[1,2-b:1',2'-k]chrysene. The basic skeleton of the formula [4] has a structure in which a benzene ring is fused at the 2-, 3-, 14-, and 15-positions of diacenaphtho[1,2-b:1',2'-k]chrysene. The basic skeleton of the formula [5] has a structure in which a benzene ring is fused at the 12-, 13-, 14-, and 15-positions of diacenaphtho[1,2-b:1',2'-k]chrysene. On the other hand, the comparative compound (4) has a structure in which a benzene ring is fused at the 1-, 2-, 11-, and 12-positions of diacenaphtho[1,2-b:1',2'-k]chrysene.

Table 8 shows that the comparative compound (4) has a higher singlet excited state (S1) than diacenaphtho[1,2-b:1', 2'-k]chrysene. In other words, the emission wavelength becomes longer. Thus, the comparative compound (4) has no emission wavelength in the blue emission region (420 to 480 nm) and cannot be used as a blue-light-emitting material. The blue-light-emitting material can have darker blue chromaticity, that is, a shorter emission wavelength, to expand the color reproduction range.

On the other hand, the basic skeleton of the compound of the second embodiment has S1 smaller than or equal to S1 of diacenaphtho[1,2-b:1',2'-k]chrysene in spite of the expansion of the fused ring. Furthermore, the basic skeleton itself has an emission wavelength in the blue emission region, and the compound of the second embodiment can be used as a blue-light-emitting material. As a matter of course, the compound of the second embodiment can have an appropriate substituent and can be used as a green- or red-light-emitting material.

Thus, the organic compound according to the second embodiment has a high quantum yield. The organic compound according to the second embodiment can be widely used as a light-emitting material from a blue region to a red region. In particular, the organic compound according to the second embodiment can be used as a light-emitting material in a dark blue region.

Furthermore, the organic compound can satisfy the following condition (5).

(5) Having a bulky substituent at the substitution position where the basic skeleton and the substituent have a large dihedral angle This is because satisfying the condition (5) increases the dihedral angle between the basic skeleton and the substituent and can further suppress molecular packing. Furthermore, when at least one substituent is a group other than a hydrogen atom, such as a bulky group, molecular packing in which basic skeletons overlap is suppressed. The dihedral angle was estimated using molecular orbital calculation. Table 9 shows the calculation results for the formula [3].

TABLE 9

| | Structure | Dihedral angle |
|---|---|---|
| 11-phenyl | 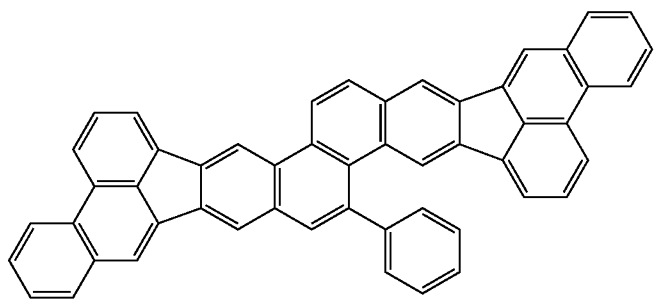 [SMILES: c1ccc(-c2cc3cc4c(cc3c3ccc5cc6c(cc5c23)-c2cccc3c2c-6cc2ccccc23)-c2cccc3c2c-4cc2ccccc23)cc1] | 58° |
| 12-phenyl | 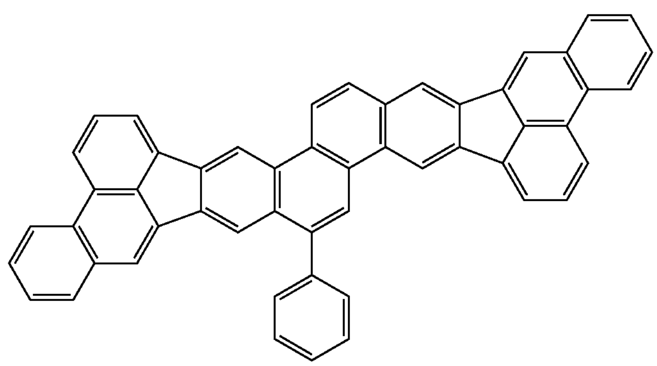 [SMILES: c1ccc(-c2cc3c4cc5c(cc4ccc3c3cc4c(cc23)-c2cc3ccccc3c3cccc-4c23)-c2cc3ccccc3c3cccc-5c23)cc1] | 59° |
| 13-phenyl | 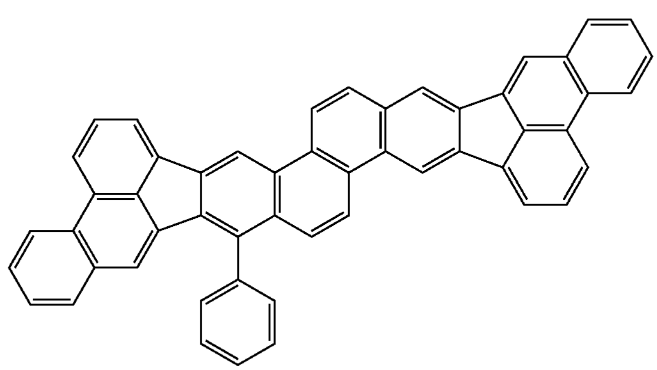 [SMILES: c1ccc(-c2c3c(cc4c2ccc2c5cc6c(cc5ccc42)-c2cc4ccccc4c4cccc-6c24)-c2cccc4c2c-3cc2ccccc24)cc1] | 90° |

TABLE 9-continued
| Structure | Dihedral angle |
|---|---|
| 14-phenyl 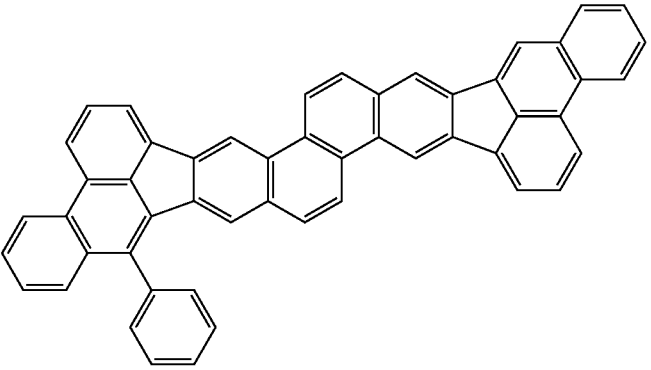 [SMILES: c1ccc(-c2c3c4c(cccc4c4ccccc24)-c2cc4c(ccc5c6cc7c(cc6ccc45)-c4cc5ccccc5c5cccc-7c45)cc2-3)cc1] | 89° |
| 15-phenyl 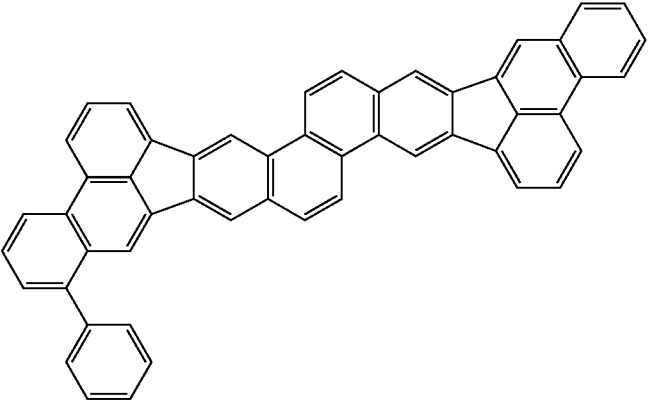 [SMILES: c1ccc(-c2cccc3c2cc2c4c(cccc43)-c3cc4c(ccc5c6cc7c(cc6ccc45)-c4cc5ccccc5c5cccc-7c45)cc3-2)cc1] | 57° |
| 16-phenyl 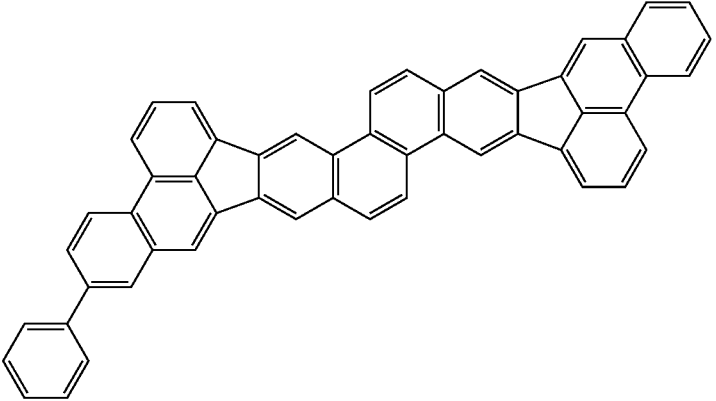 [SMILES: c1ccc(-c2ccc3c(c2)cc2c4c(cccc43)-c3cc4c(ccc5c6cc7c(cc6ccc45)-c4cc5ccccc5c5cccc-7c45)cc3-2)cc1] | 37° |
| 17-phenyl 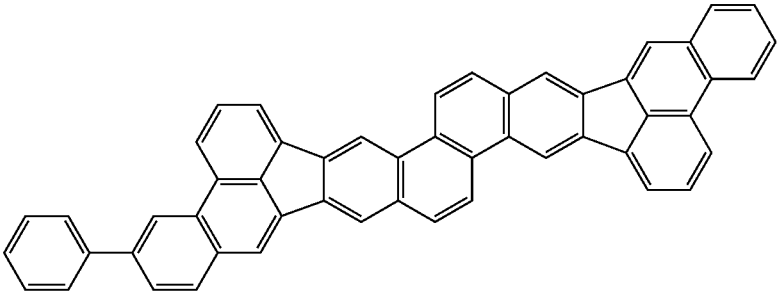 [SMILES: c1ccc(-c2ccc3cc4c5c(cccc5c3c2)-c2cc3c(ccc5c6cc7c(cc6ccc35)-c3cc5ccccc5c5cccc-7c35)cc2-4)cc1] | 37° |

TABLE 9-continued
| Structure | Dihedral angle |
|---|---|
| 18-phenyl 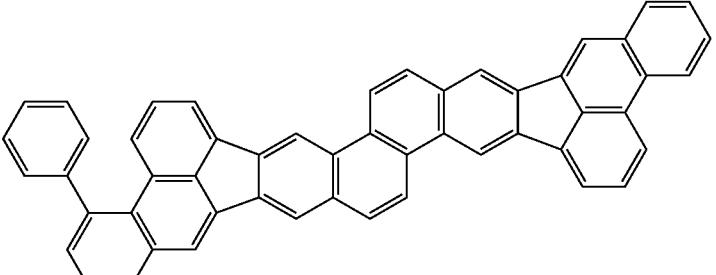 | 73° |
| 19-phenyl 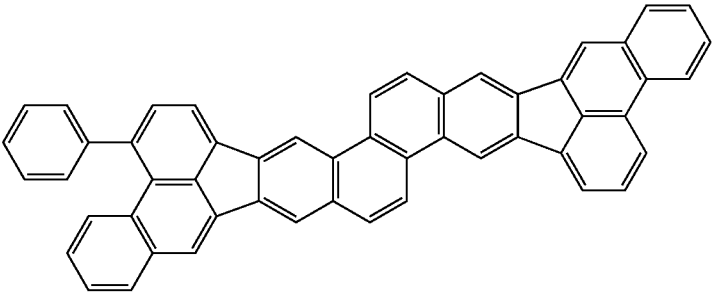 [SMILES: c1ccc(-c2ccc3c4c(cc5ccccc5c24)-c2cc4ccc5c6cc7c(cc6ccc5c4cc2-3)-c2cc3ccccc3c3cccc-7c23)cc1] | 68° |
| 20-phenyl 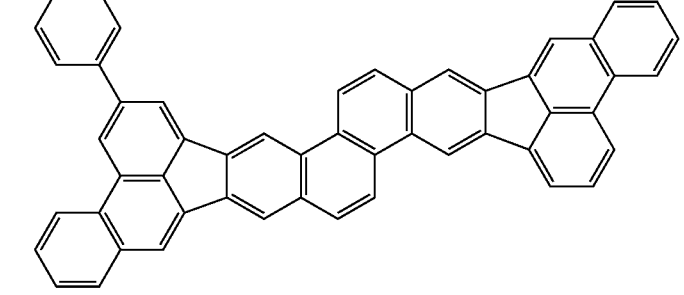 | 40° |
| 21-phenyl 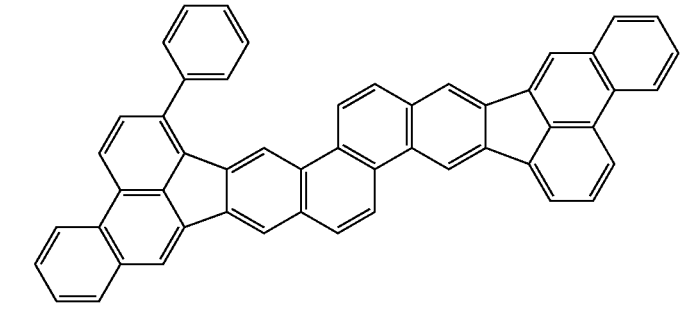 [SMILES: c1ccc(-c2ccc3c4c(cc5ccccc53)-c3cc5ccc6c7cc8c(cc7ccc6c5cc3-c24)-c2cc3ccccc3c3cccc-8c23)cc1] | 55° |
| 22-phenyl 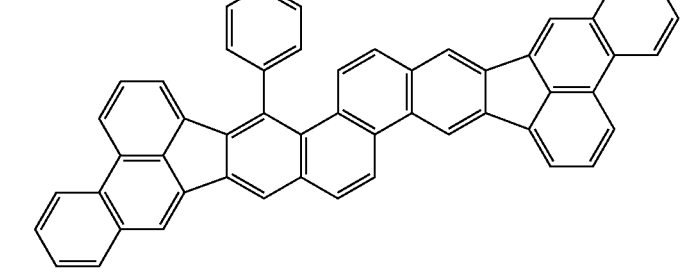 | 81° |

TABLE 9-continued
| | Structure | Dihedral angle |
|---|---|---|
| 1-phenyl | 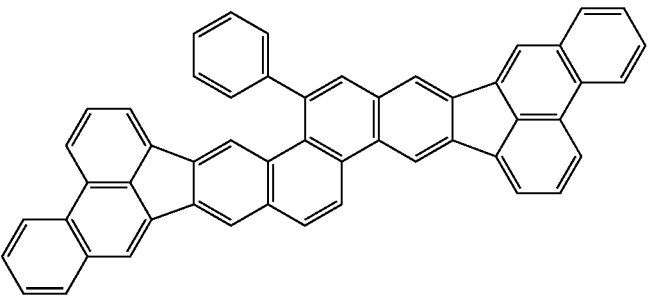 [SMILES: c1ccc(-c2cc3cc4c(cc3c3ccc5cc6c(cc5c23)-c2cccc3c2c-6cc2ccccc23)-c2cccc3c2c-4cc2ccccc23)cc1] | 58° |
| 2-phenyl | 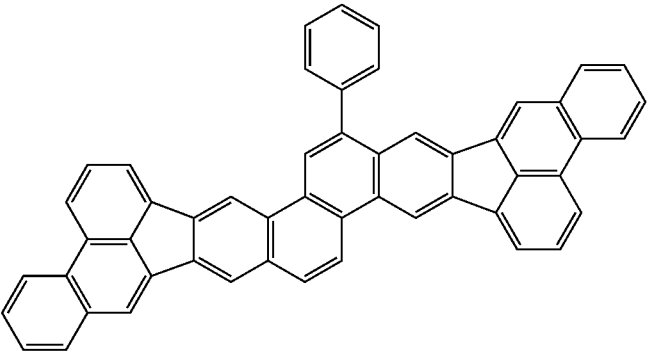 [SMILES: c1ccc(-c2cc3c4cc5c(cc4ccc3c3cc4c(cc23)-c2cc3ccccc3c3cccc-4c23)-c2cc3ccccc3c3cccc-5c23)cc1] | 59° |
| 3-phenyl | 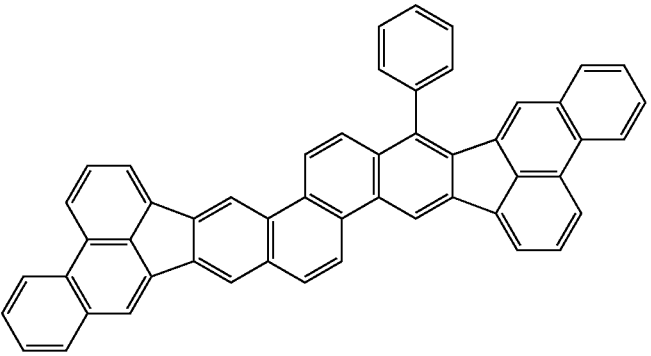 [SMILES: c1ccc(-c2c3c(cc4c2ccc2c5cc6c(cc5ccc42)-c2cc4ccccc4c4cccc-6c24)-c2cccc4c2c-3cc2ccccc24)cc1] | 90° |
| 4-phenyl | 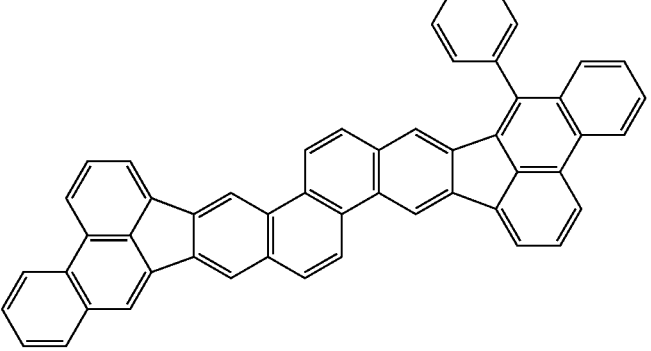 | 89° |

TABLE 9-continued
| Structure | Dihedral angle |
|---|---|
| 23-phenyl 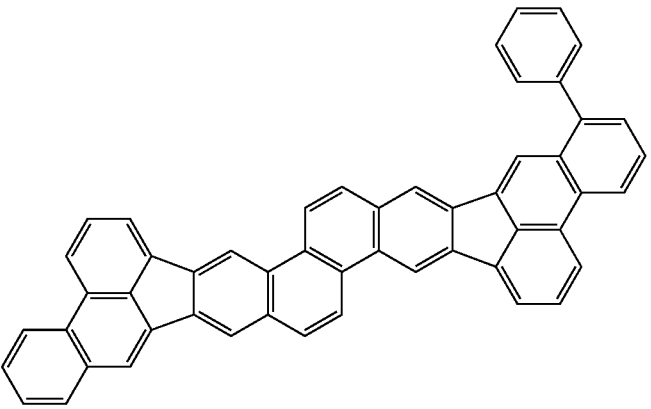 [SMILES: c1ccc(-c2cccc3c2cc2c4c(cccc43)-c3cc4c(ccc5c6cc7c(cc6ccc45)-c4cc5ccccc5c5cccc-7c45)cc3-2)cc1] | 57° |
| 24-phenyl 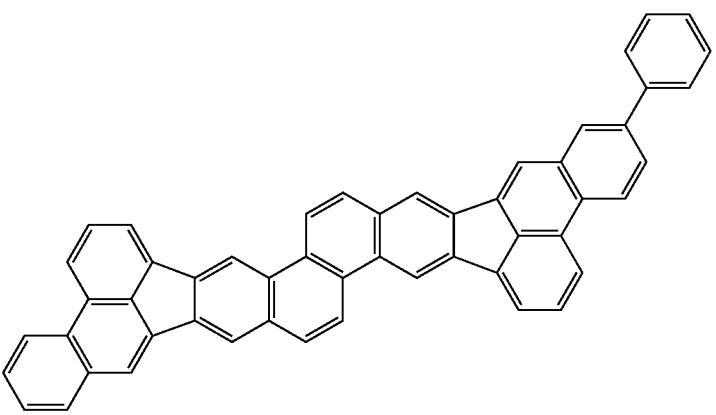 [SMILES: c1ccc(-c2ccc3c(c2)cc2c4c(cccc43)-c3cc4c(ccc5c6cc7c(cc6ccc45)-c4cc5ccccc5c5cccc-7c45)cc3-2)cc1] | 37° |
| 25-phenyl 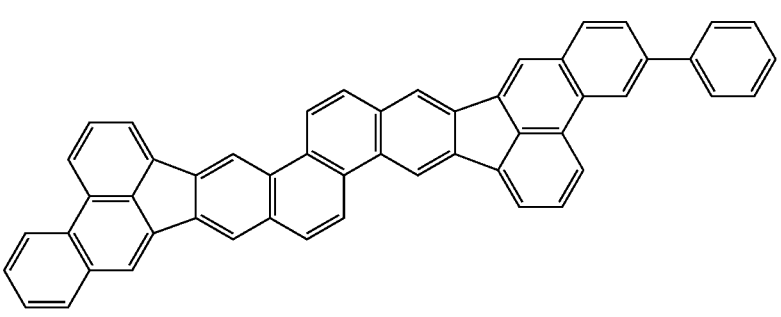 [SMILES: c1ccc(-c2ccc3cc4c5c(cccc5c3c2)-c2cc3c(ccc5c6cc7c(cc6ccc35)-c3cc5ccccc5c5cccc-7c35)cc2-4)cc1] | 37° |
| 26-phenyl 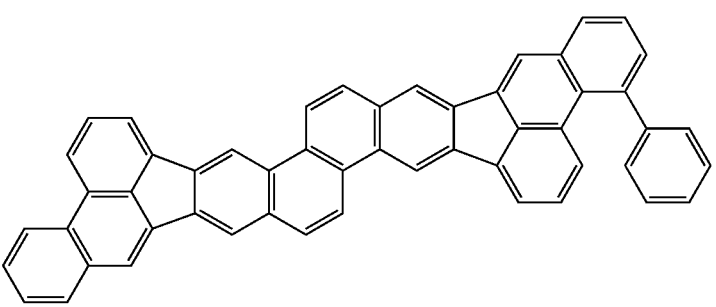 [SMILES: c1ccc(-c2cccc3cc4c5c(cccc5c23)-c2cc3c(ccc5c6cc7c(cc6ccc35)-c3cc5ccccc5c5cccc-7c35)cc2-4)cc1] | 71° |

TABLE 9-continued

| Structure | Dihedral angle |
|---|---|
| 7-phenyl | 69° |
| 8-phenyl | 40° |
| 9-phenyl | 57° |
| 10-phenyl | 81° |

Table 9 shows that $R_1$ to $R_4$, $R_7$, $R_{10}$ to $R_{14}$, $R_{15}$ and $R_{19}$, $R_{22}$, and $R_{26}$ in the formula [3] have a dihedral angle of 58 degrees or more. Due to their sufficiently large dihedral angles, the substituents (phenyl groups) can reduce π-π interaction between the basic skeletons. Thus, the material can have high solubility and good sublimation properties.

The substitution positions can be $R_1$ to $R_3$, $R_{10}$ to $R_{13}$, and $R_{22}$, or $R_2$ and $R_3$, $R_{10}$, $R_{12}$ and $R_{13}$, and $R_{22}$. This is because these substitution positions are the substitution positions of the chrysene moiety at the center of the molecule of the basic skeleton and can more effectively suppress molecular packing.

As a matter of course, the same results can be obtained for the formulae [4] and [5].

Specific examples of an organic compound according to the present disclosure are described below. However, the present disclosure is not limited to these examples.

A1
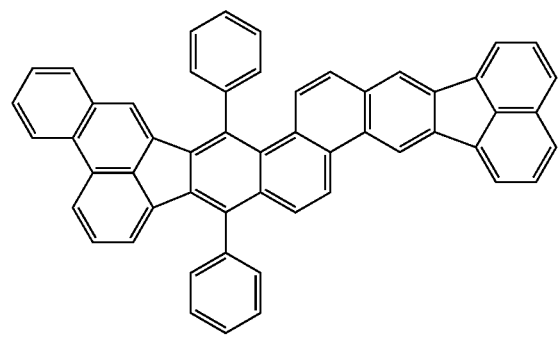
A4
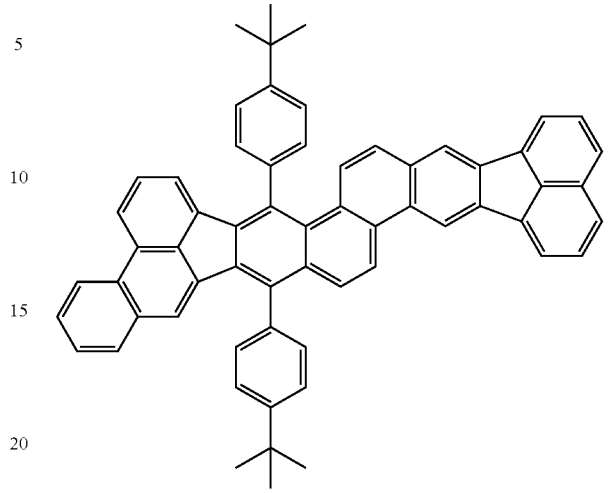
A2
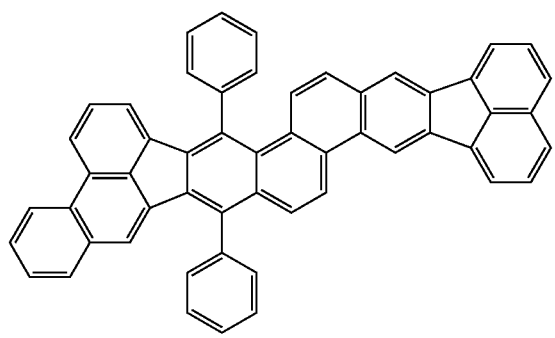
A5
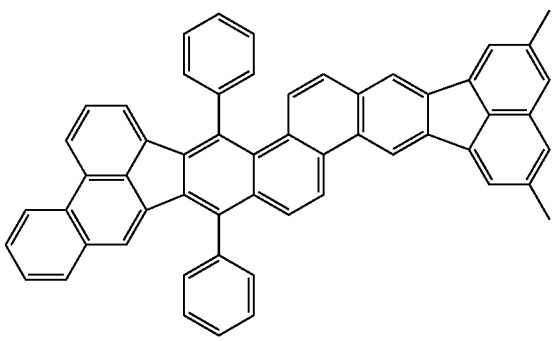
A6
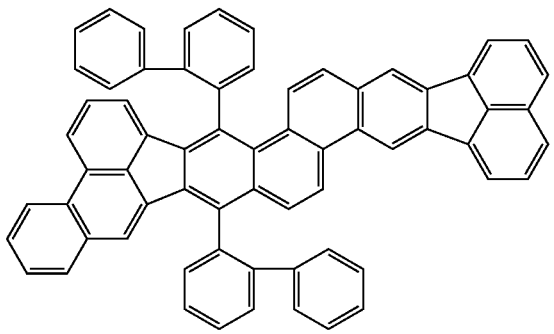
A3
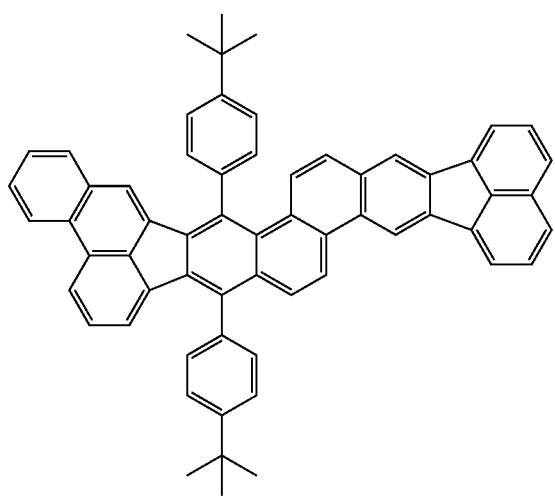
A7
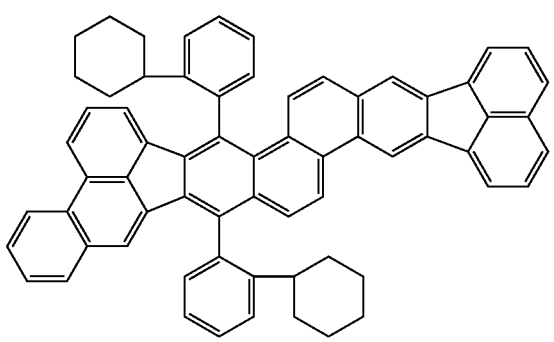

A8
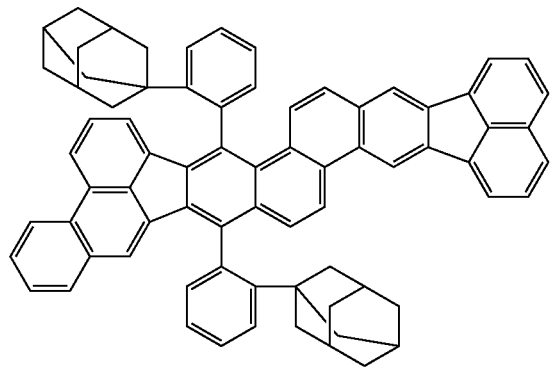
A12
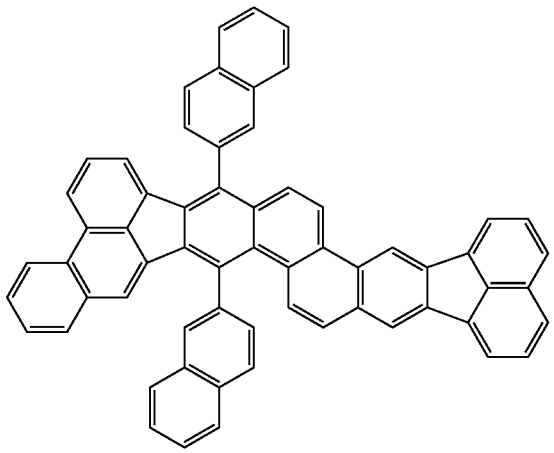
A9
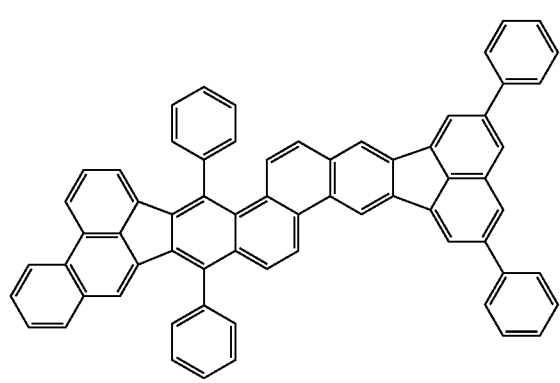
A13
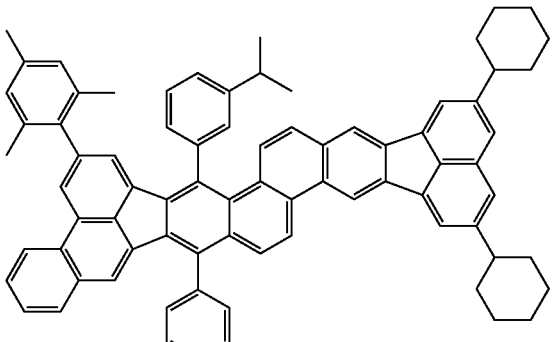
A10
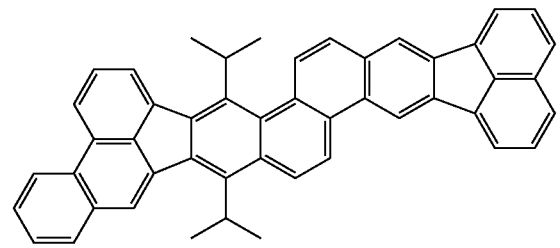
A11
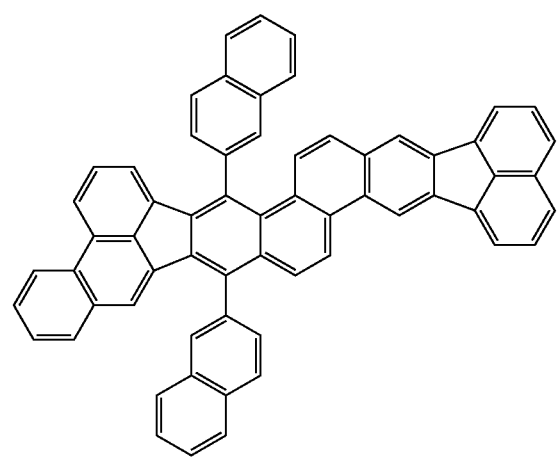
A14
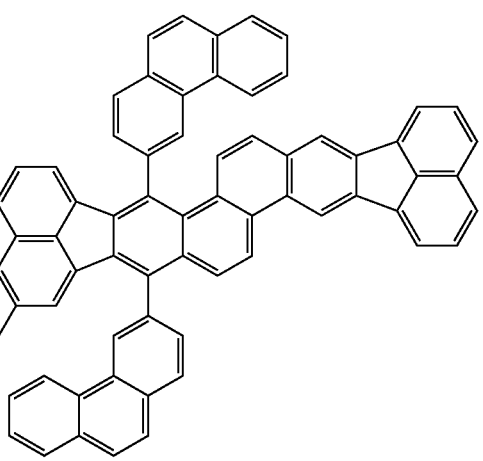

A15
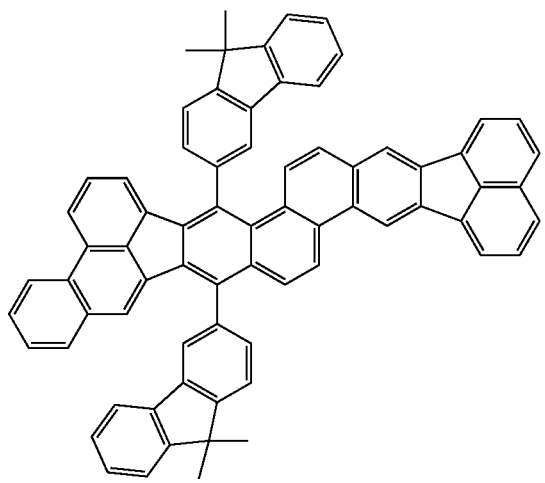
A16
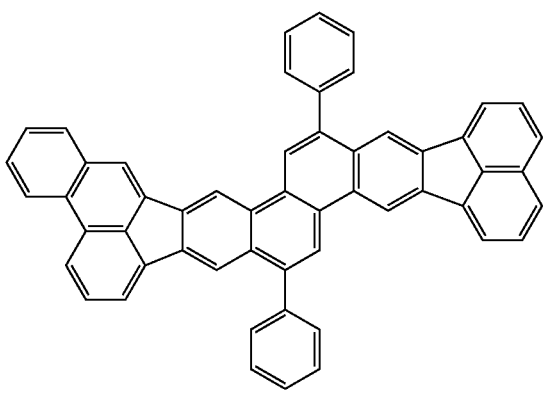
A17
A18
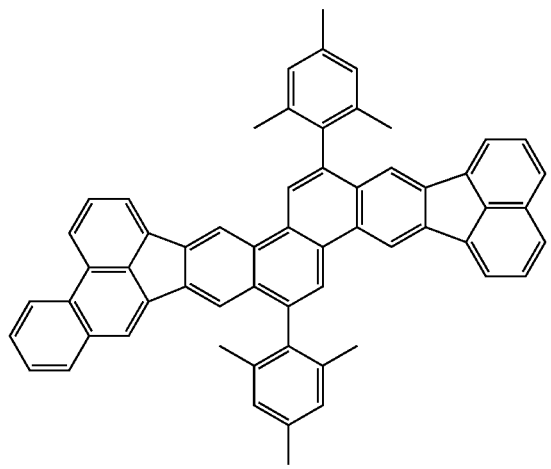
A19
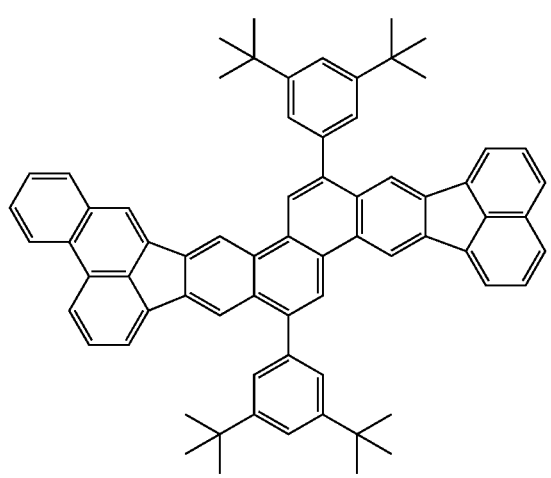
A20
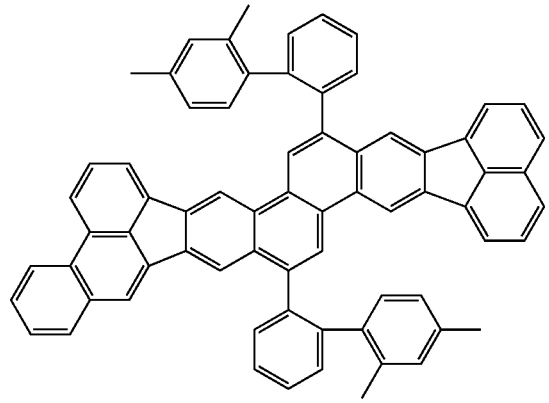

A21
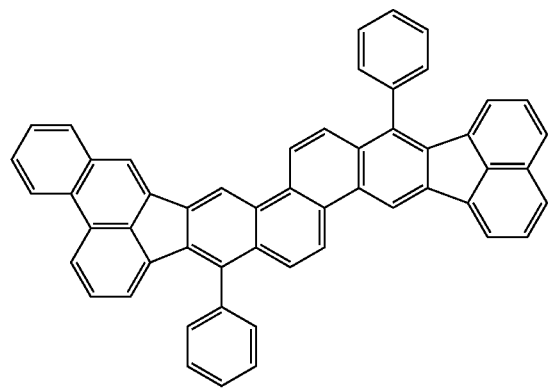
A22
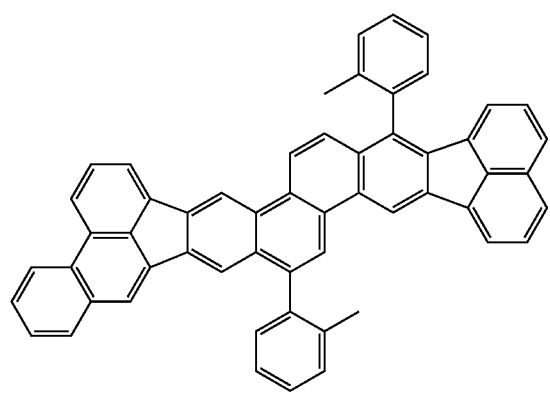
A23
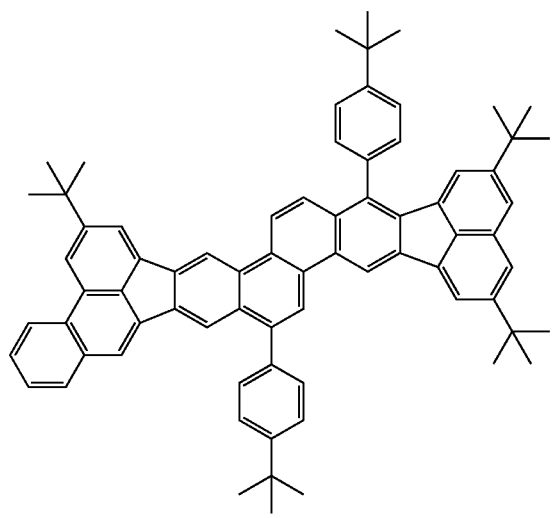
A24
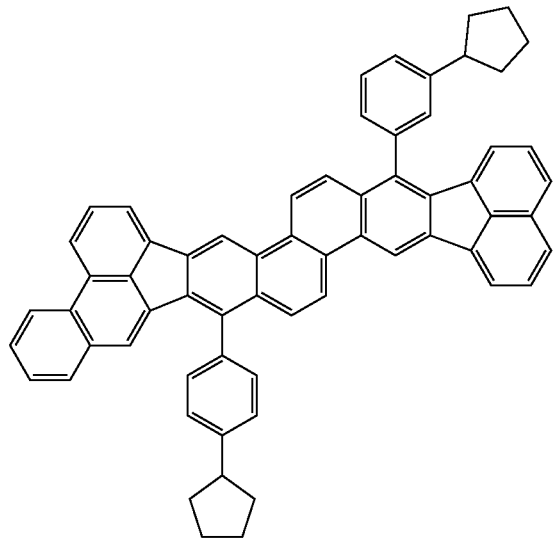
B1
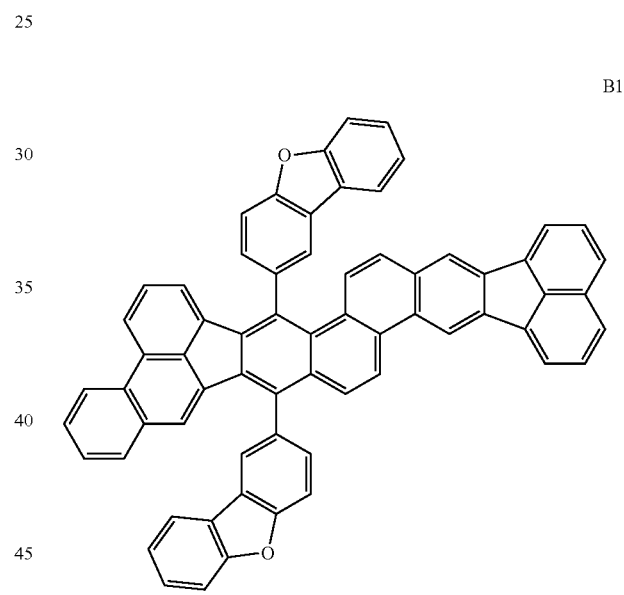
B2
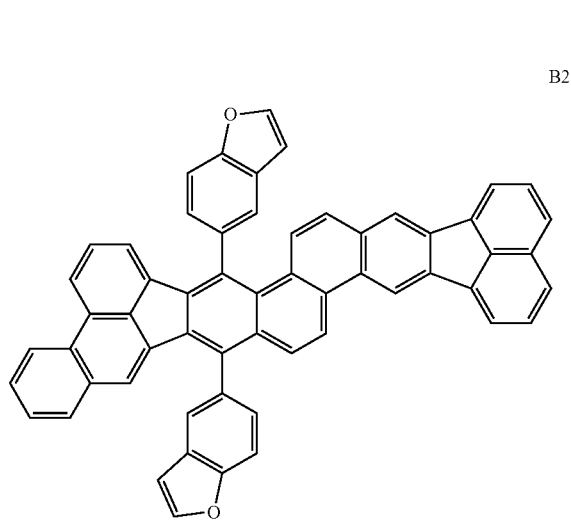

B3
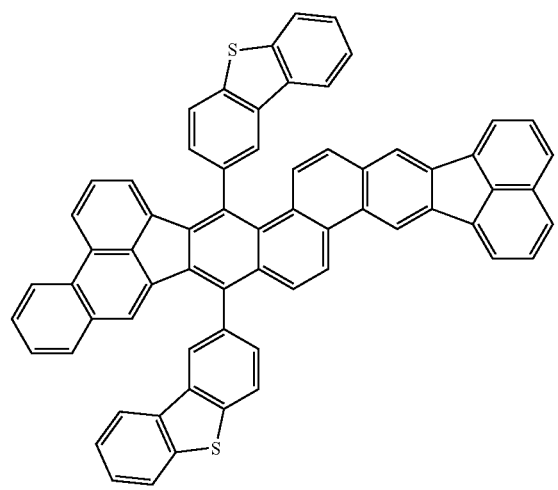
B4
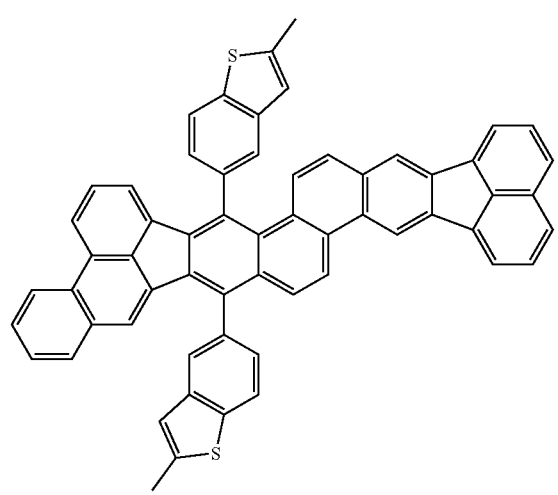
B5
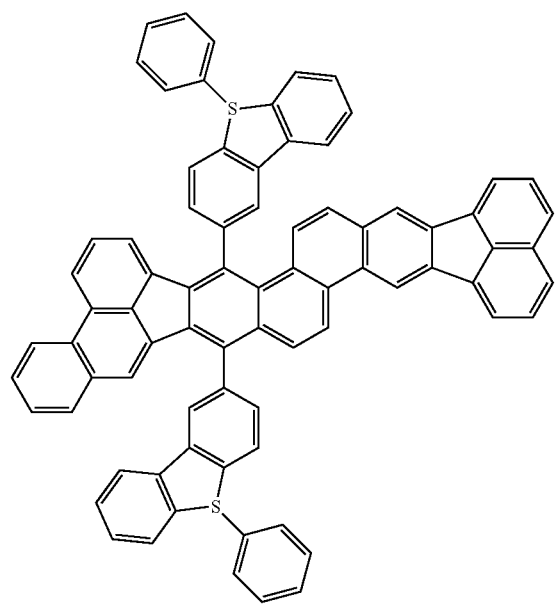
B6
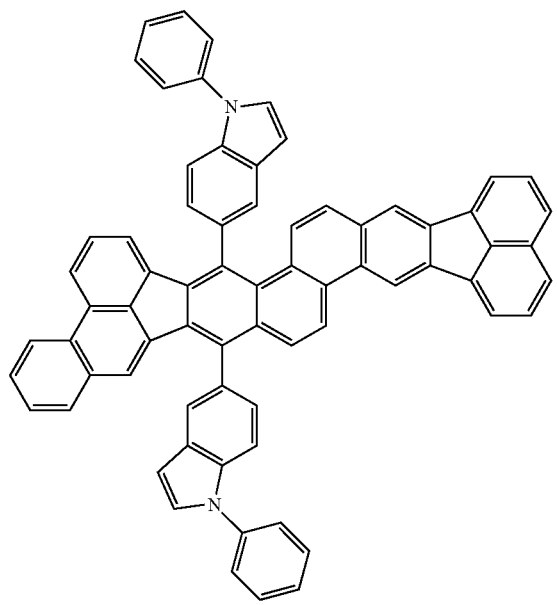
B7
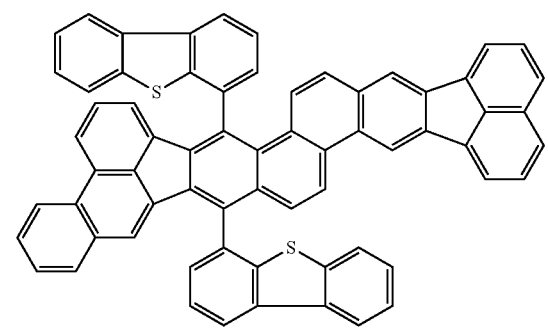
B8
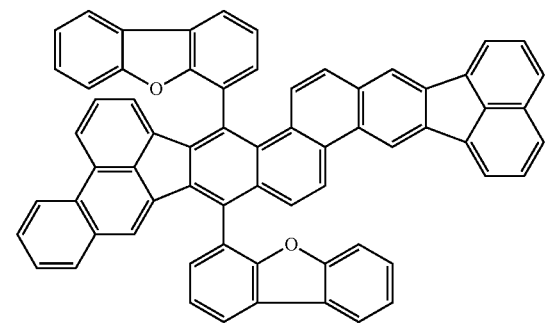

-continued
B9
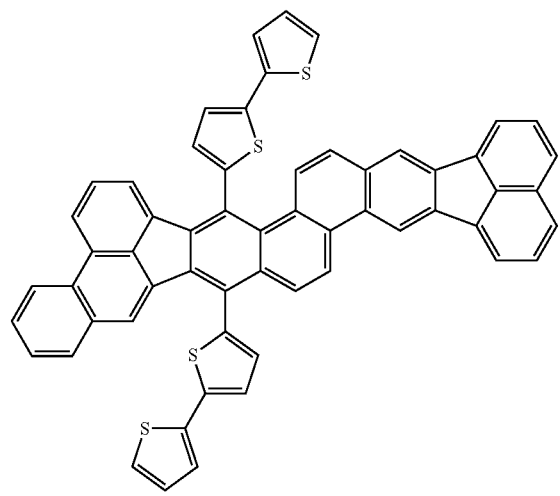
B10
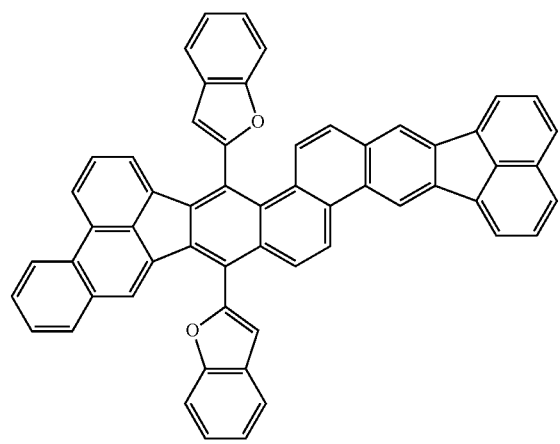
B11
-continued
B12
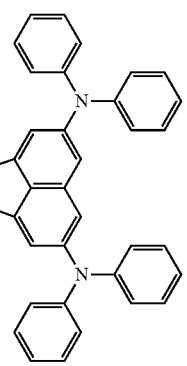
B13
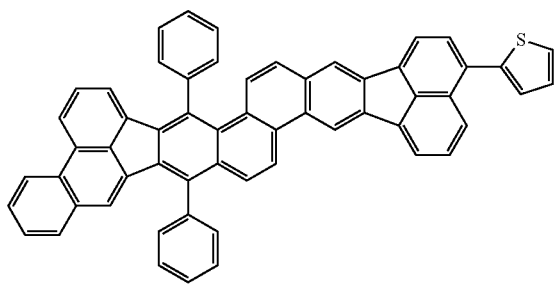
B14
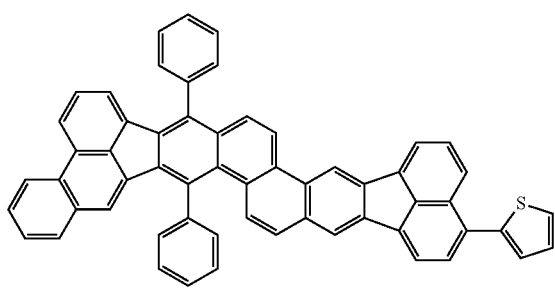
B15
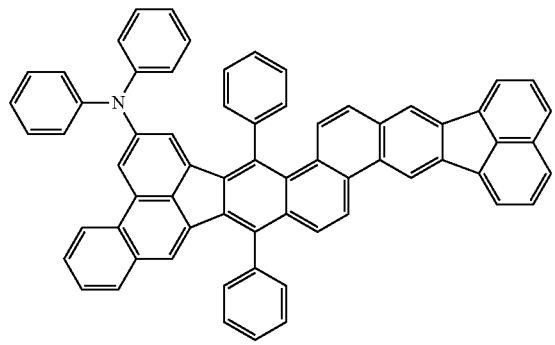

B16
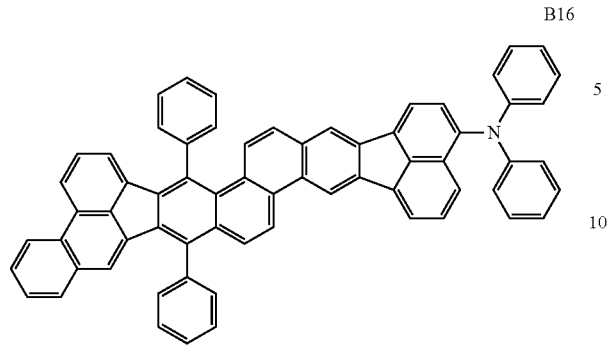
B17
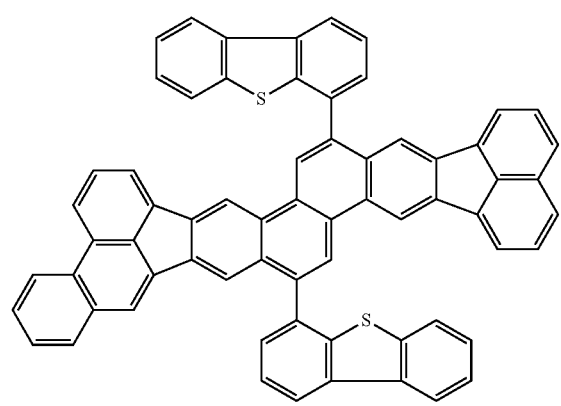
B18
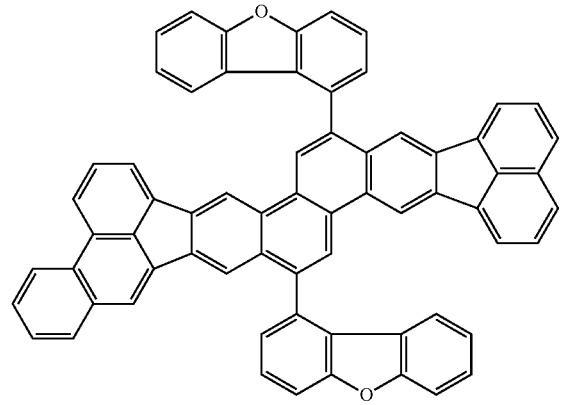
B19
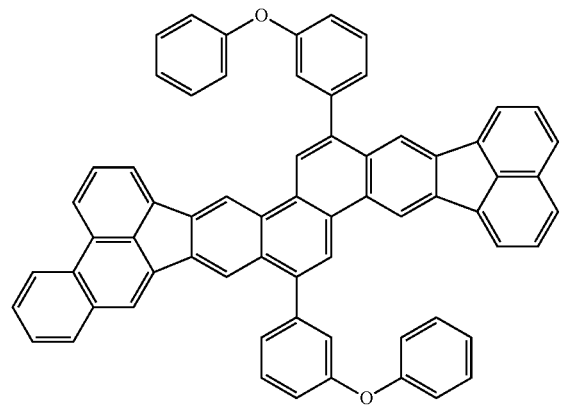
B20
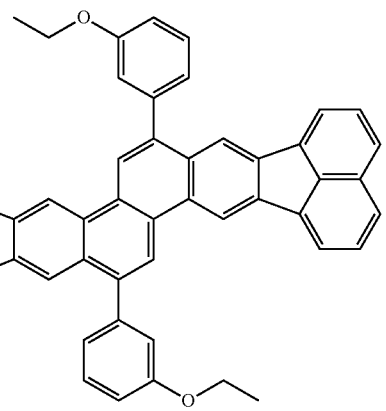
B21
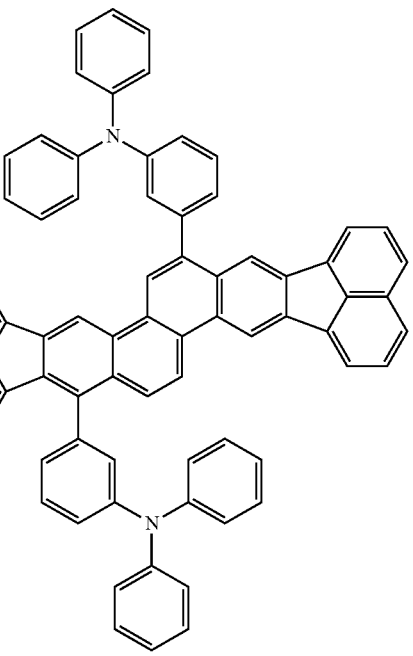
B22
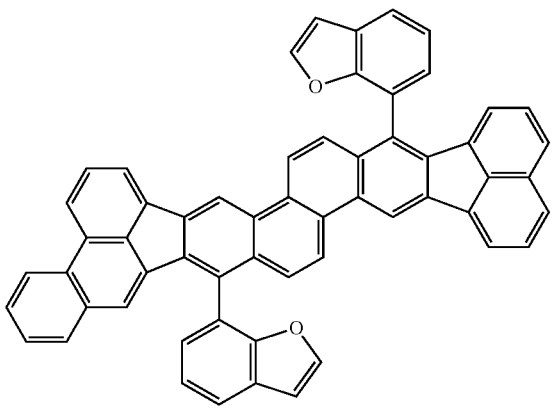

B23
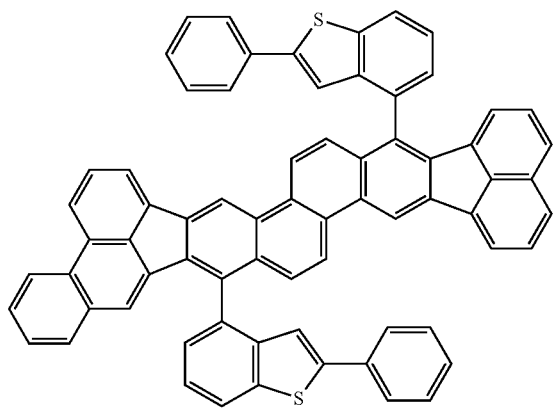
E2
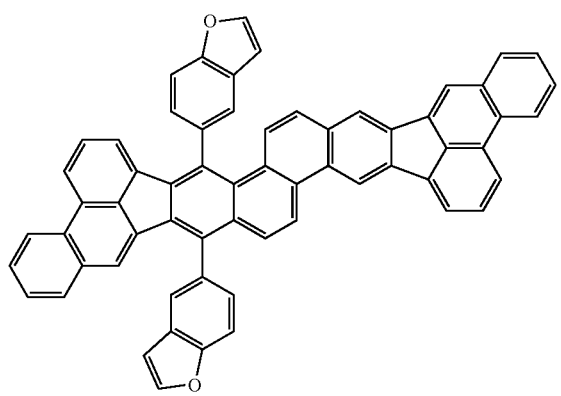
B24
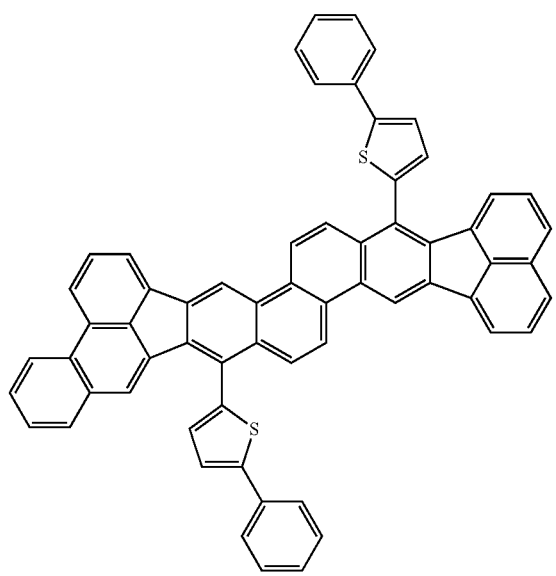
E3
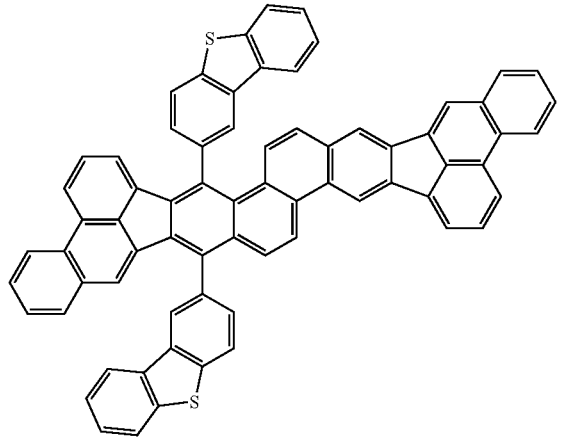
E1
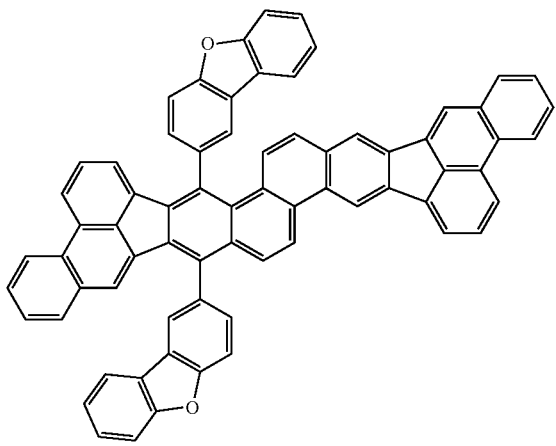
E4
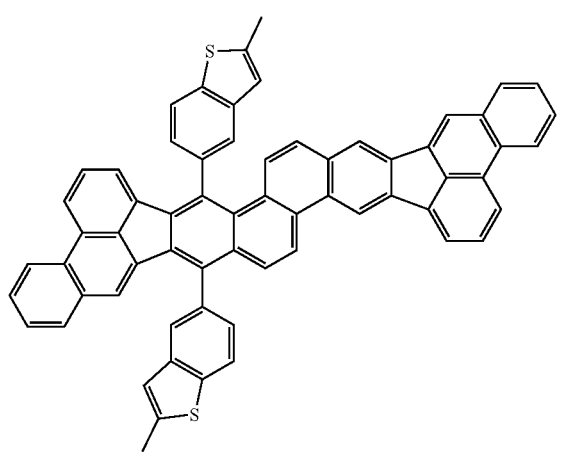

-continued
E5
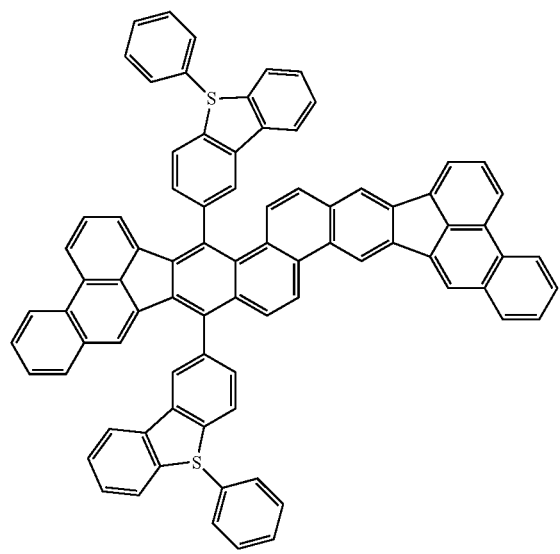
E6
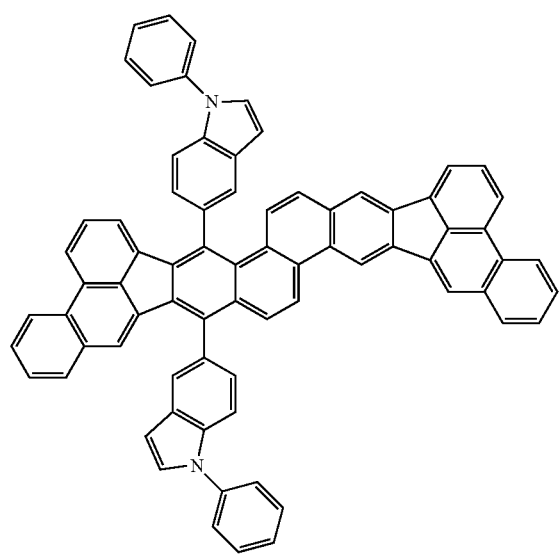
E7
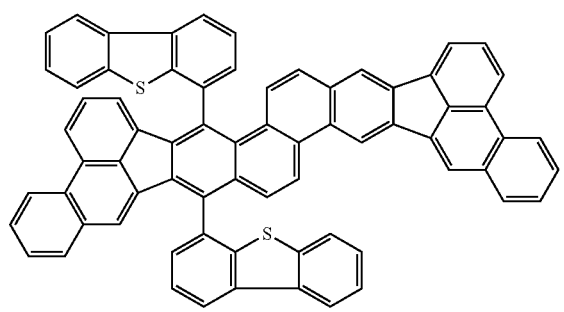
-continued
E8
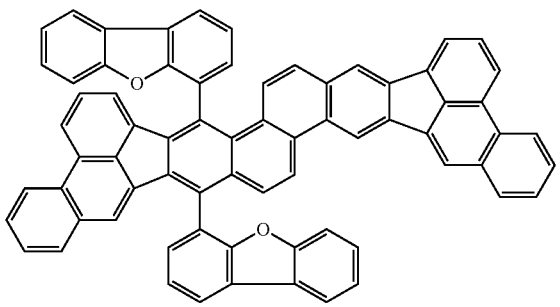
E9
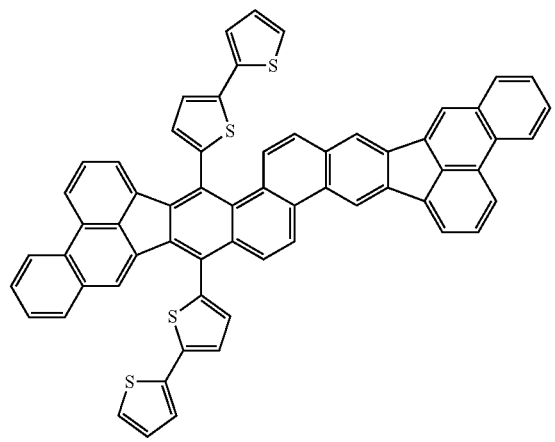
E10
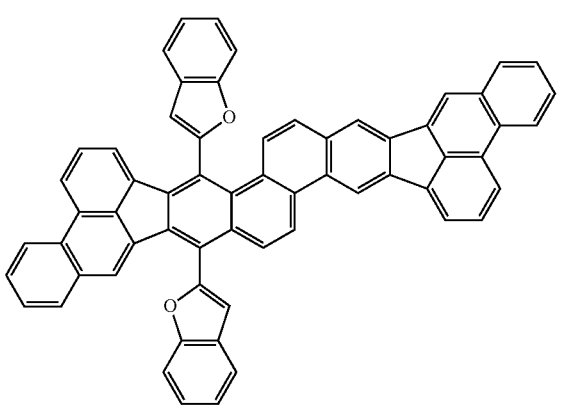
E11

-continued
E12
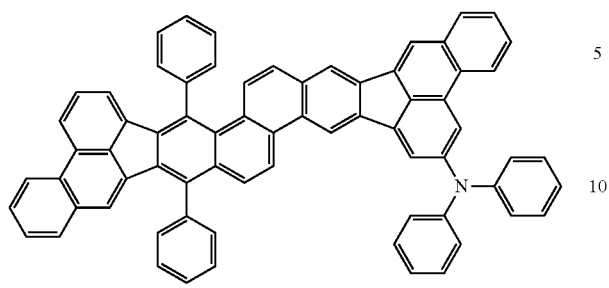
E13
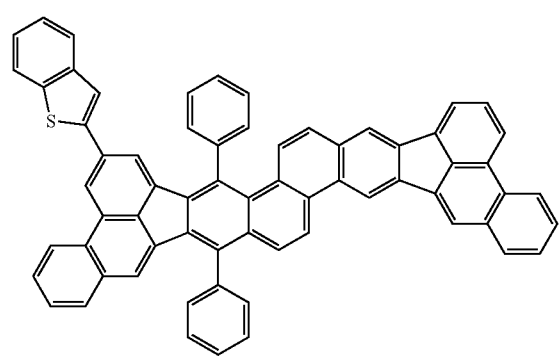
E14
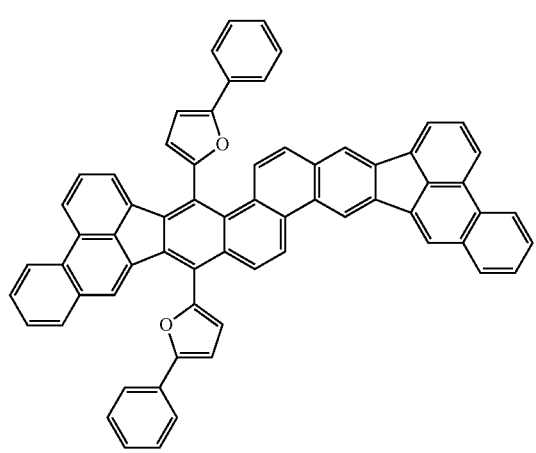
E15
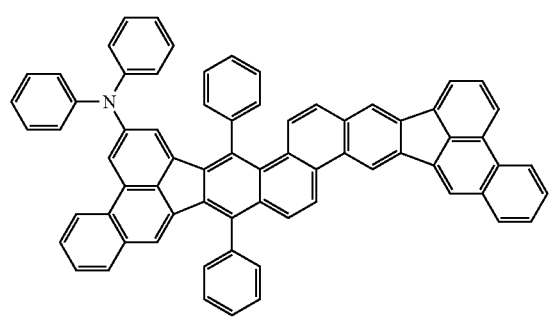
-continued
E16
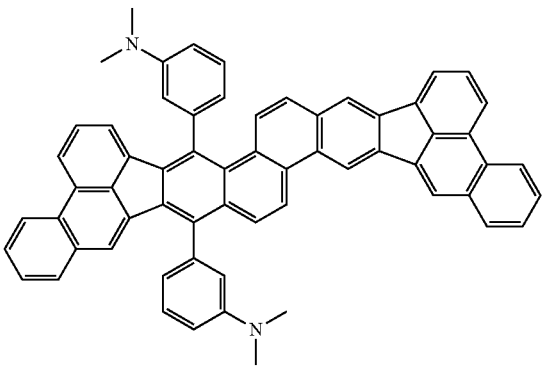
E17
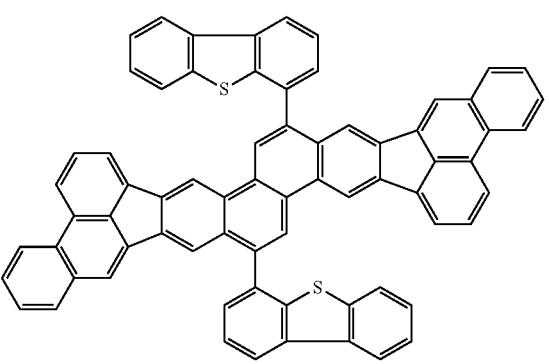
E18
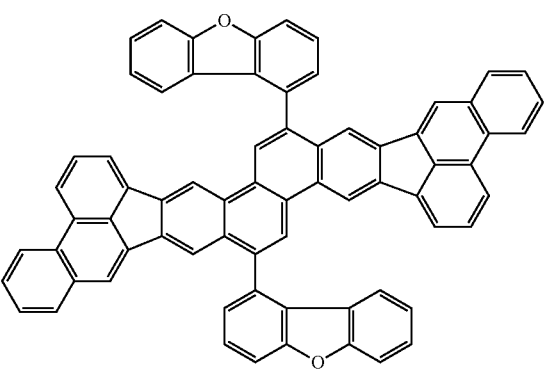
E19
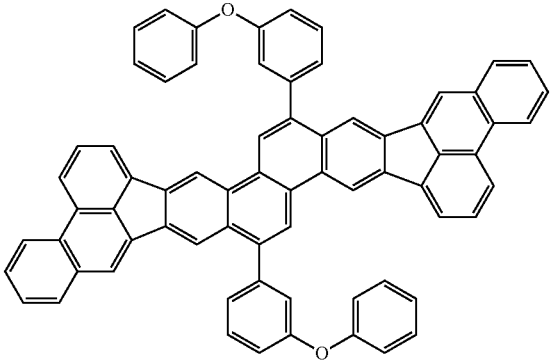

E20
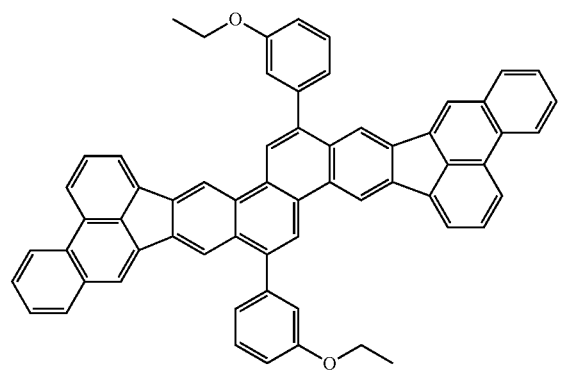
E21
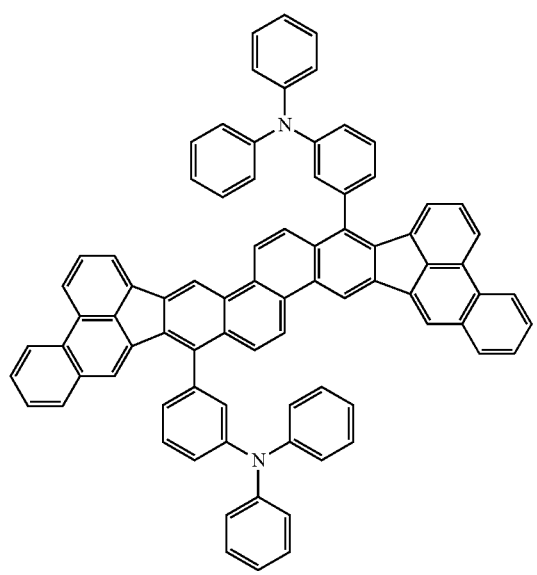
E22
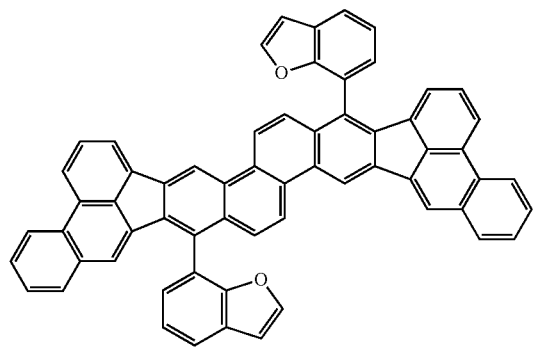
E23
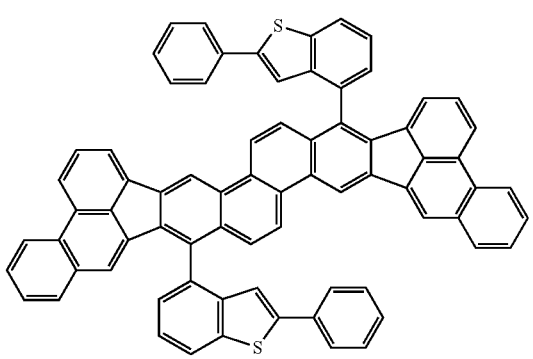
E24
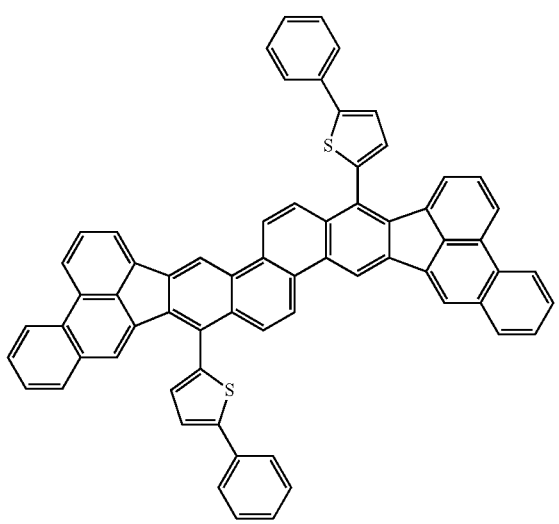
F1
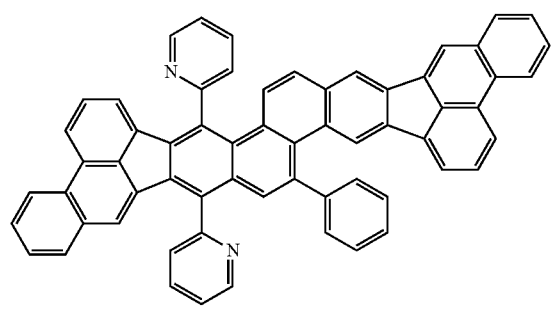
F2
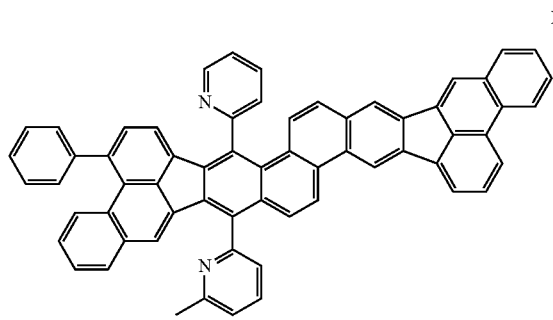

71 72
-continued -continued
F3
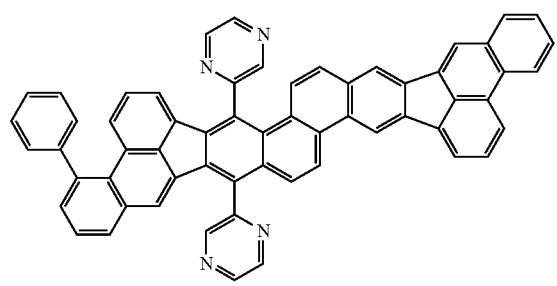
F4
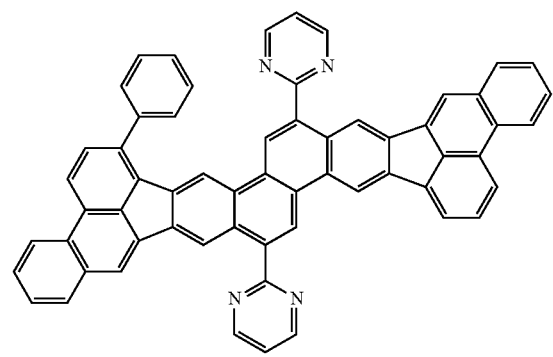
F5
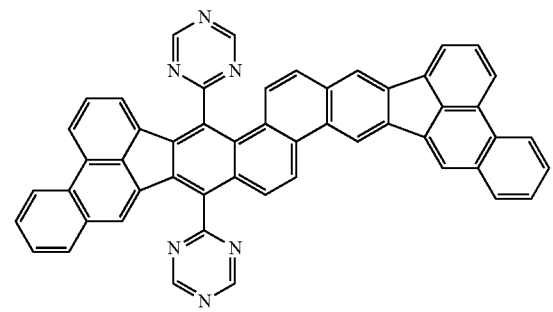
F6
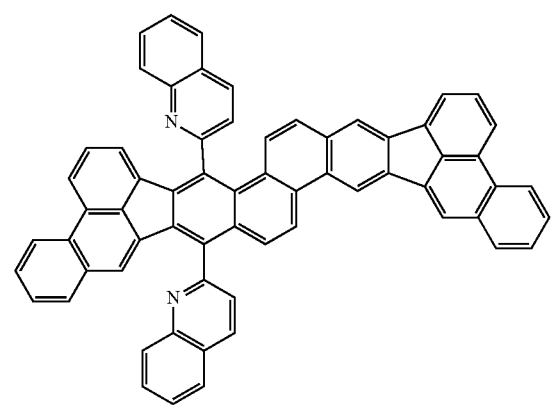
F7
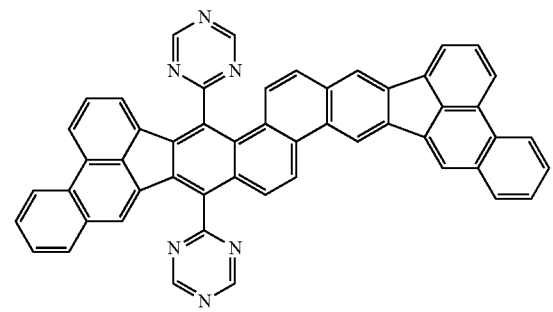
F8
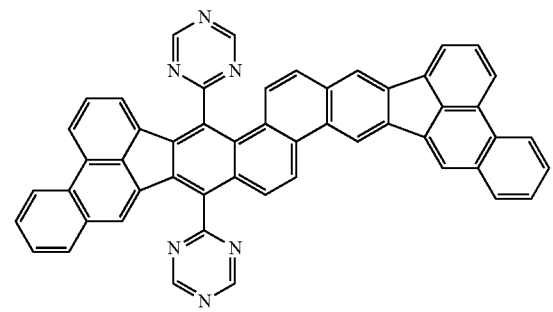
F9
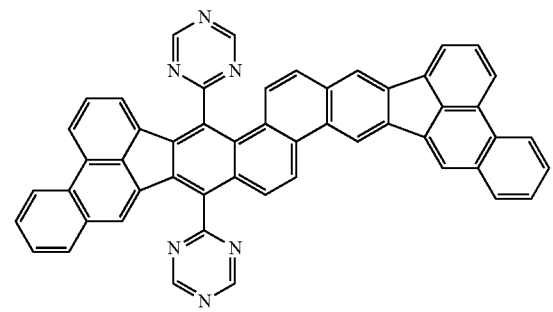
F10
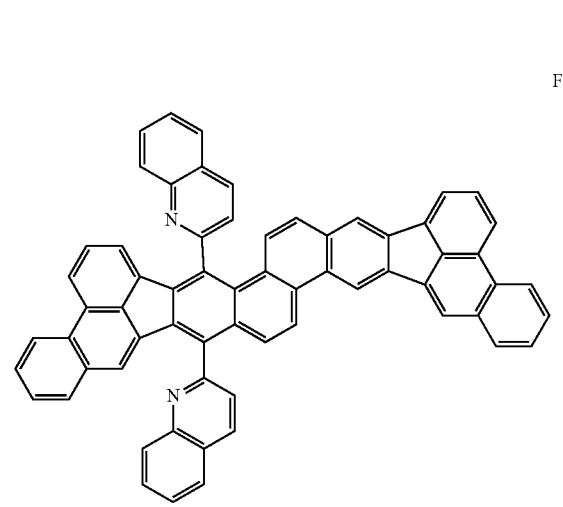

F11
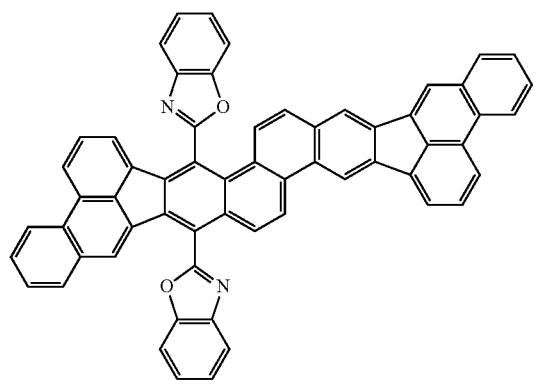
F15
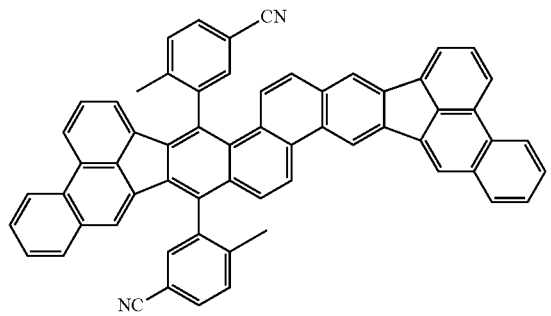
F12
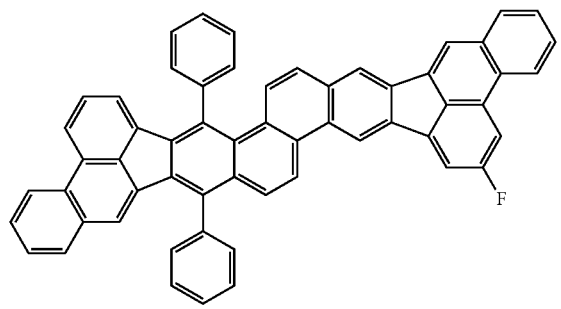
F16
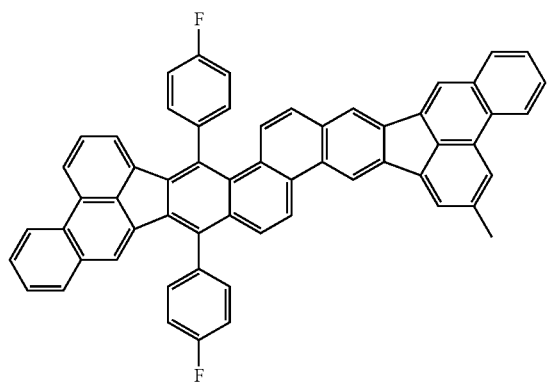
F13
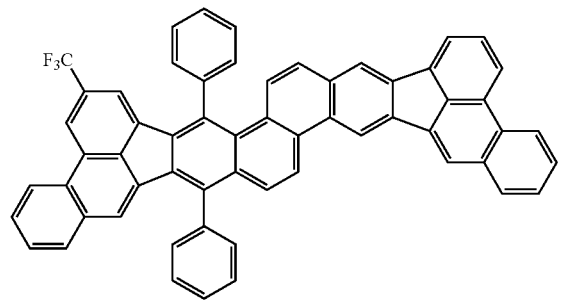
F17
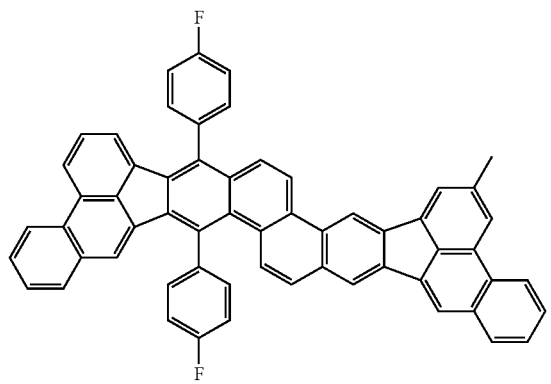
F14
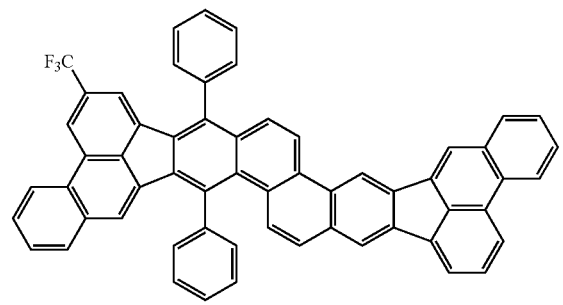
F18
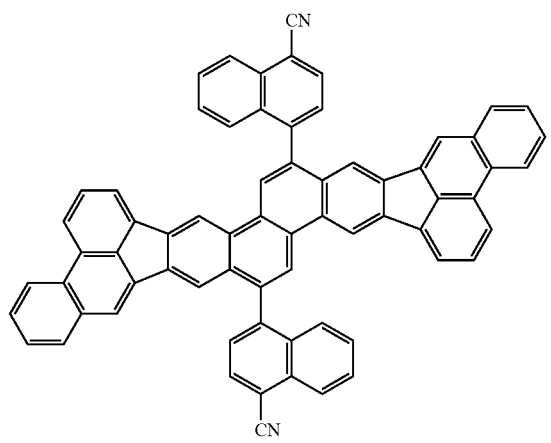

F19
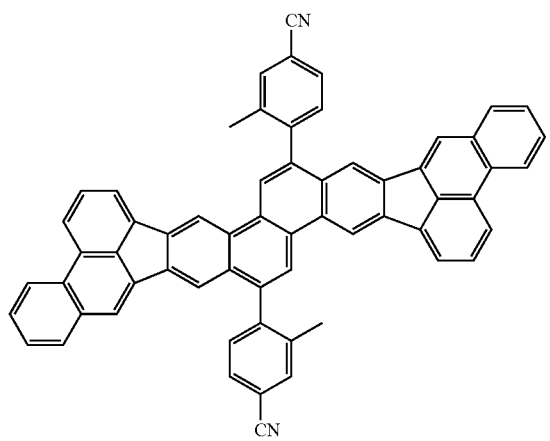

F20
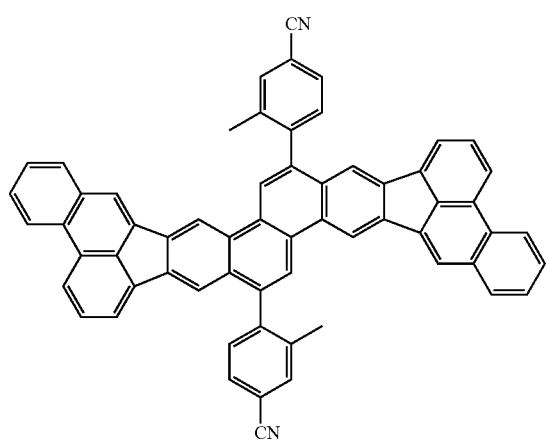

F21
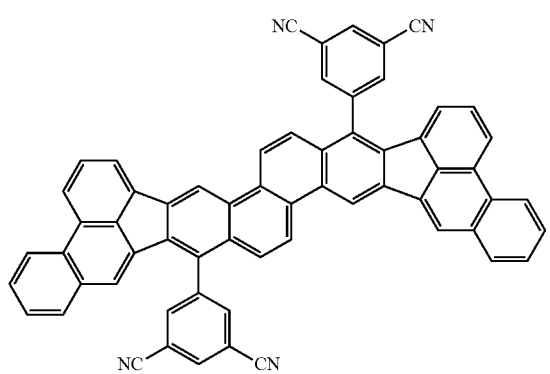

F22
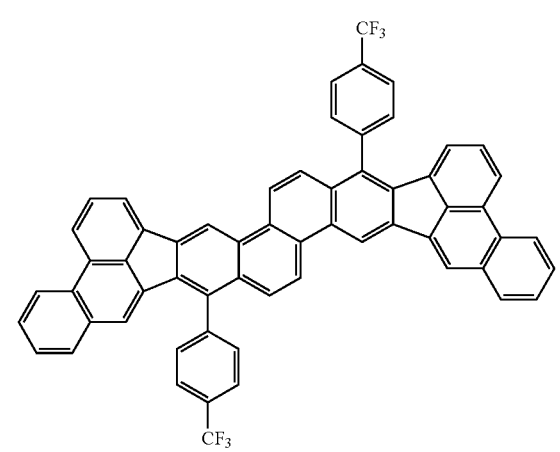

F23
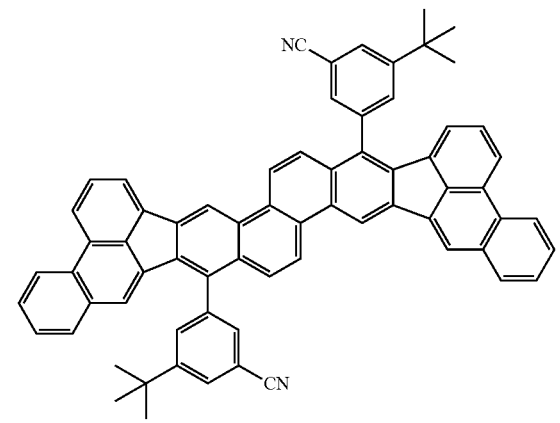

F24
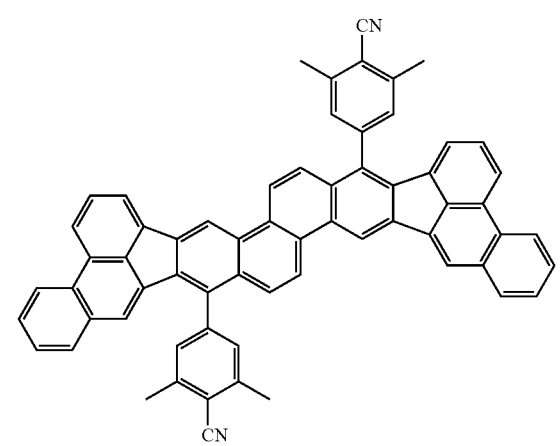

Exemplary compounds belonging to the group D are compounds in which $R_1$ to $R_{26}$ denote a hydrogen atoms, an alkyl group, or an aromatic hydrocarbon group. Thus, such a compound has high chemical stability. Thus, these compounds can be used to provide a light-emitting device with high durability.

Exemplary compounds belonging to the group E are compounds having as $R_1$ to $R_{26}$ or a substituent thereof a heterocyclic group or a group with a heteroatom. The heterocyclic group or the group with a heteroatom can adjust the HOMO level and the LUMO level of the compound and is suitable to adjust the carrier balance of a light-emitting device.

Exemplary compounds belonging to the group F are compounds having as $R_1$ to $R_{26}$ or a substituent thereof an electron-deficient heterocyclic group or an electron-withdrawing group. Thus, such a compound has a deep HOMO level (far from the vacuum level) and high oxidative stability. Also having a deep LUMO level, such a compound can be used as a light-emitting material for a light-emitting layer to provide a light-emitting device with an electron-trapping light-emitting layer. Such a compound can also be used as a material constituting an electron-injection layer adjacent to a cathode electrode or an electron-accepting layer in a charge-generating layer.

<<Organic Light-Emitting Device>>

An organic light-emitting device according to the present embodiment includes at least a pair of electrodes, a positive electrode and a negative electrode, and an organic compound layer between the electrodes. In the organic light-emitting device according to the present embodiment, the organic compound layer may be a single layer or a laminate of a plurality of layers, provided that the organic compound layer has a light-emitting layer.

When the organic compound layer is a laminate of a plurality of layers, the organic compound layer may have a hole-injection layer, a hole-transport layer, an electron-blocking layer, a hole/exciton-blocking layer, an electron-transport layer, and/or an electron-injection layer, in addition to the light-emitting layer. The light-emitting layer may be a single layer or a laminate of a plurality of layers.

In the organic light-emitting device according to the present embodiment, at least one layer of the organic compound layer contains the organic compound according to the present embodiment. More specifically, the organic compound according to the present embodiment is contained in any of the hole-injection layer, the hole-transport layer, the electron blocking layer, the light-emitting layer, the hole/exciton-blocking layer, the electron-transport layer, the electron-injection layer, and the like. The organic compound according to the present embodiment can be contained in the light-emitting layer.

In the organic light-emitting device according to the present embodiment, when the organic compound according to the present embodiment is contained in the light-emitting layer, the light-emitting layer may be composed only of the organic compound according to the present embodiment or may be composed of the organic compound according to the present embodiment and another compound. When the light-emitting layer is composed of the organic compound according to the present embodiment and another compound, the organic compound according to the present embodiment may be used as a host or a guest of the light-emitting layer. The organic compound may also be used as an assist material that may be contained in the light-emitting layer. The host is the compound with the highest weight ratio among the compounds constituting the light-emitting layer. The guest is a compound that has a lower weight ratio than the host among the compounds constituting the light-emitting layer and that is a principal light-emitting compound. The assist material is a compound that has a lower weight ratio than the host among the compounds constituting the light-emitting layer and that assists the guest in emitting light. The assist material is also referred to as a second host.

When the organic compound according to the present embodiment is used as a guest of the light-emitting layer, the concentration of the guest preferably ranges from 0.01% to 20% by mass, more preferably 0.1% to 5% by mass, of the entire light-emitting layer.

When the organic compound according to the present embodiment is used as a guest of the light-emitting layer, a material composed of an aromatic hydrocarbon can be used as a host. This is because the organic compound according to the present embodiment is a material with a basic skeleton composed of a fused polycyclic aromatic hydrocarbon, and a material composed of a similar aromatic hydrocarbon can be used as a host to provide a light-emitting layer with good compatibility between the host and the guest.

The present inventors have conducted various studies and have found that the organic compound according to the present embodiment can be used as a host or a guest of a light-emitting layer, particularly as a guest of the light-emitting layer, to provide a device that can efficiently emit bright light and that has very high durability. The light-emitting layer may be monolayer or multilayer. Blue light emission may be chosen as an emission color of the present embodiment for color mixture with a light-emitting material of another emission color. The multilayer means a laminate of the light-emitting layer and another light-emitting layer. In this case, the emission color of the organic light-emitting device is not limited to blue. More specifically, the emission color may be white or a neutral color. In the case of white, another light-emitting layer emits light of a color other than blue, such as green or red. Such a layer is formed by vapor deposition or coating. This is described in detail below in exemplary embodiments.

The organic compound according to the present embodiment can be used as a constituent material of an organic compound layer other than the light-emitting layer constituting the organic light-emitting device according to the present embodiment. More specifically, the organic compound according to the present embodiment may be used as a constituent material of an electron-transport layer, an electron-injection layer, a hole-transport layer, a hole-injection layer, and/or a hole-blocking layer. In such a case, the emission color of the organic light-emitting device is not limited to blue. More specifically, the emission color may be white or a neutral color.

If necessary, the organic compound according to the present embodiment may be used in combination with a known low-molecular-weight or high-molecular-weight hole-injection compound or hole-transport compound, host compound, light-emitting compound, electron-injection compound, or electron-transport compound. Examples of these compounds are described below.

The hole-injection or hole-transport material can be a material that can facilitate the injection of holes from a positive electrode and that has high hole mobility to transport the injected holes to a light-emitting layer. To prevent degradation of film quality, such as crystallization, in the organic light-emitting device, a material with a high glass transition temperature can be used. Examples of the low-molecular-weight or high-molecular-weight material with hole injection transport ability include, but are not limited to, triarylamine derivatives, aryl carbazole derivatives, phenylenediamine derivatives, stilbene derivatives, phthalocyanine derivatives, porphyrin derivatives, polyvinylcarbazole, polythiophene, and other electrically conductive polymers. The hole-injection or hole-transport material is also suitable for an electron-blocking layer. Specific examples of compounds that can be used as the hole-injection or hole-transport material are described below. As a matter of course, the present disclosure is not limited to these compounds.
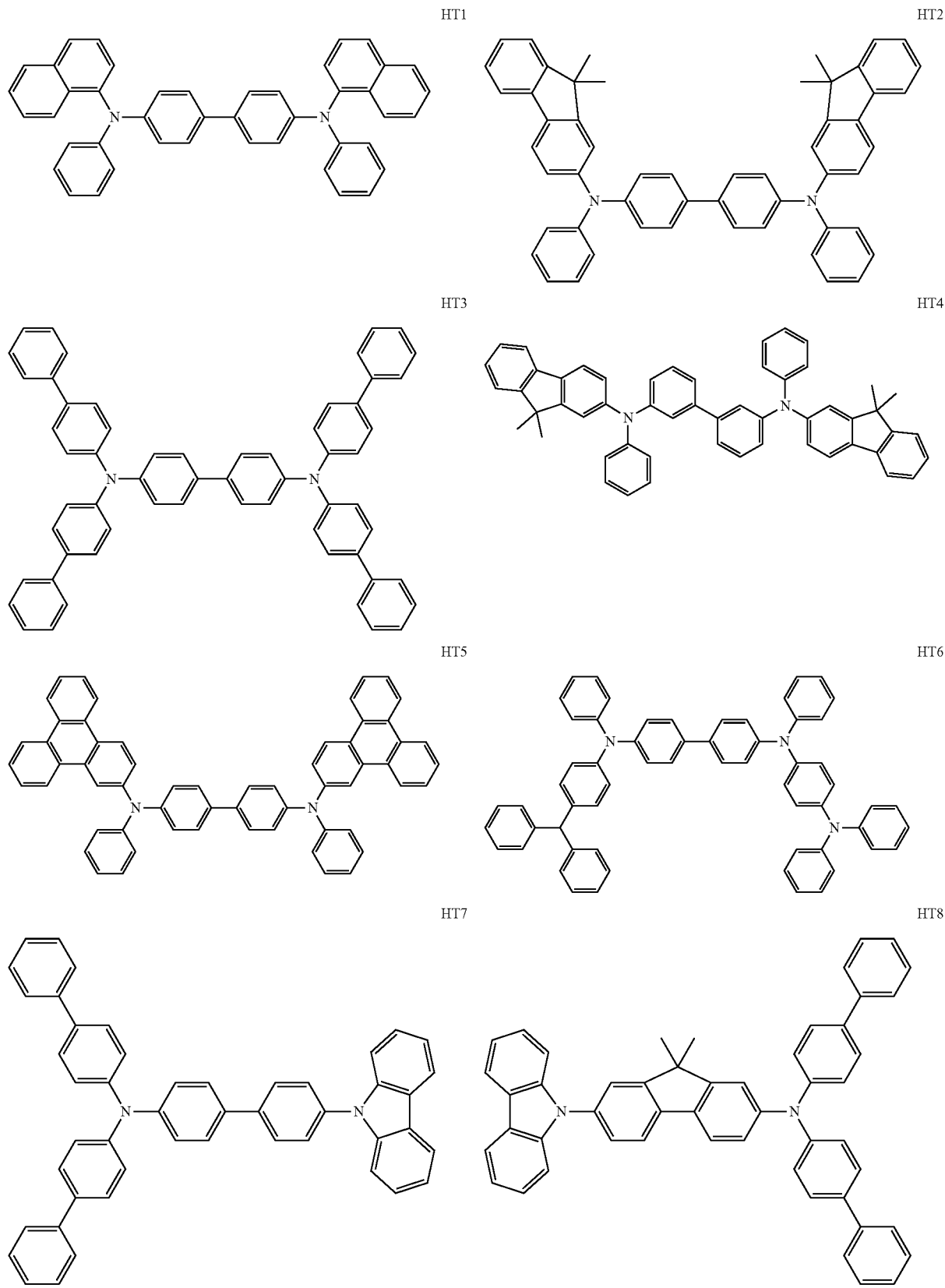

-continued
HT9
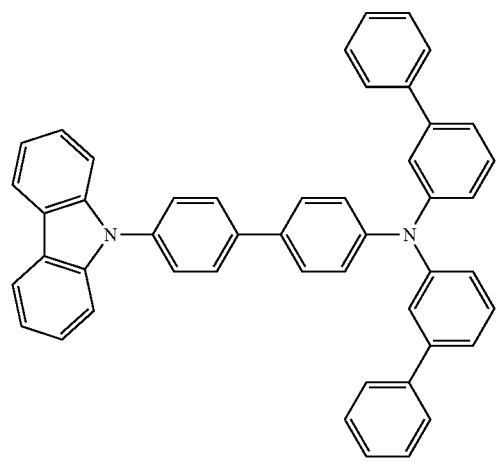
HT10
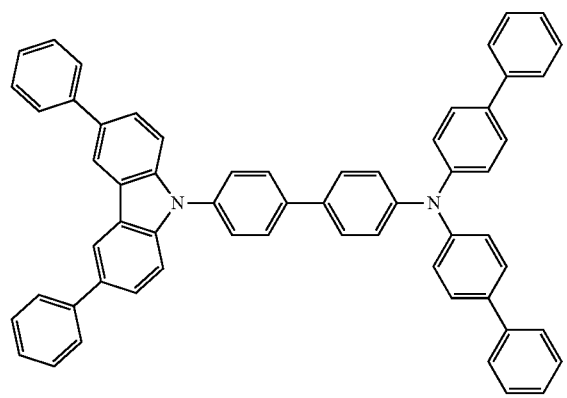
HT11
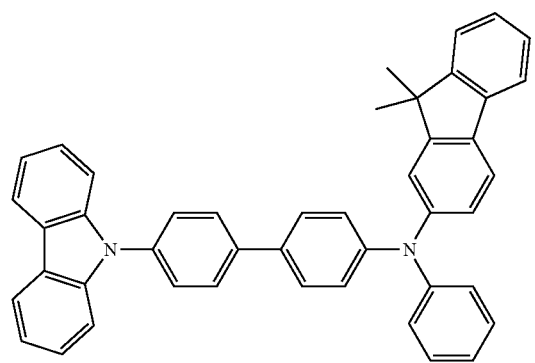
HT12
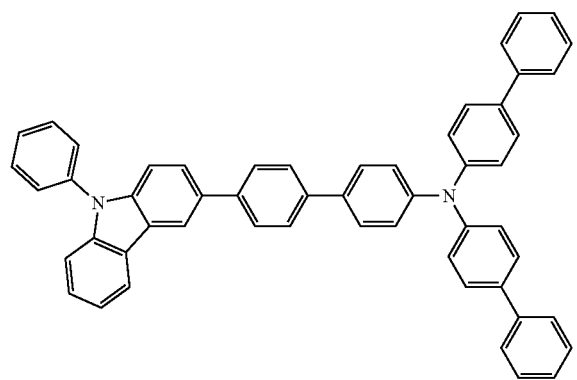
HT13
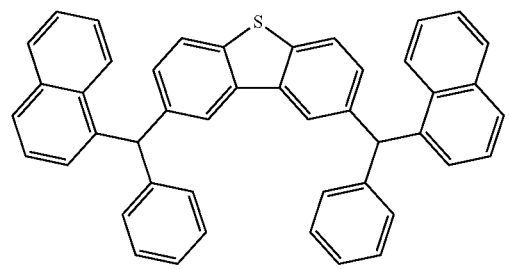
HT14
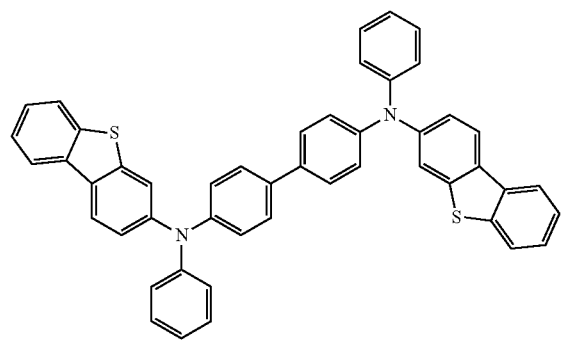
HT15
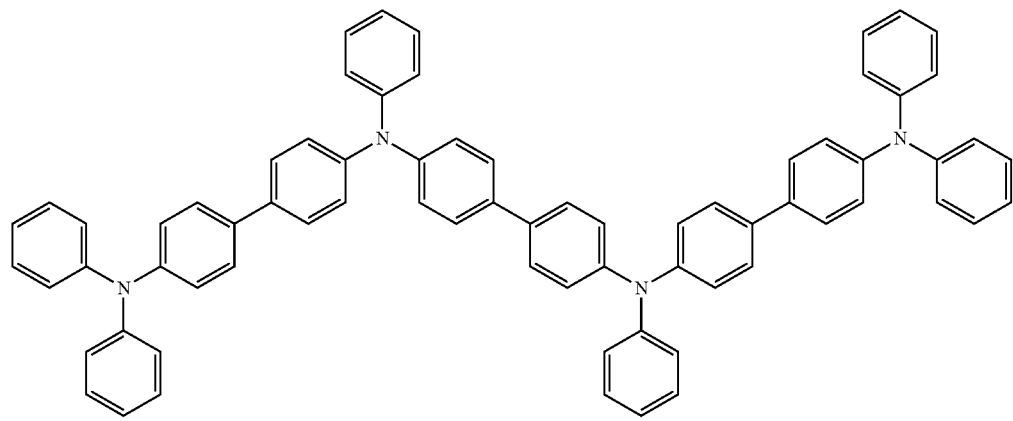

HT16 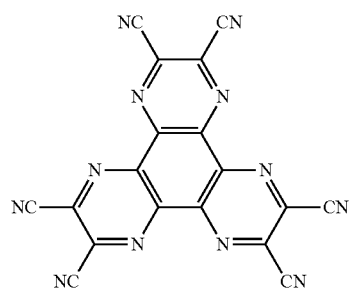

HT17 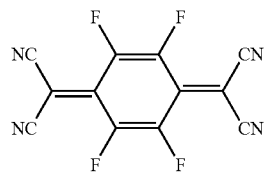

HT18 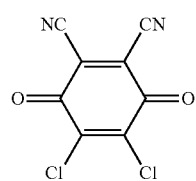

HT19 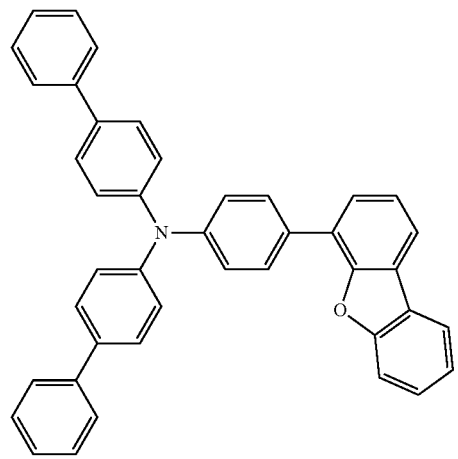

Examples of the light-emitting material mainly related to the light-emitting function include, in addition to the organic compound according to the present embodiment, fused-ring compounds (for example, fluorene derivatives, naphthalene derivatives, pyrene derivatives, perylene derivatives, tetracene derivatives, anthracene derivatives, rubrene, etc.), quinacridone derivatives, coumarin derivatives, stilbene derivatives, organoaluminum complexes, such as tris(8-quinolinolato) aluminum, iridium complexes, platinum complexes, rhenium complexes, copper complexes, europium complexes, ruthenium complexes, and polymer derivatives, such as poly(phenylene vinylene) derivatives, polyfluorene derivatives, and polyphenylene derivatives.

The organic compound according to the present embodiment has two electron-deficient five-membered rings in the basic skeleton and therefore has low HOMO/LUMO energy. Thus, when a mixture layer with another light-emitting material is formed, or when light-emitting layers are laminated, another light-emitting material can also have low HOMO/LUMO energy. This is because high HOMO/LUMO energy may result in the formation of a quenching component or a trap level, such as the formation of an exciplex with the organic compound according to the present embodiment.

Specific examples of compounds that can be used as the light-emitting material are described below. As a matter of course, the present disclosure is not limited to these compounds.

BD1 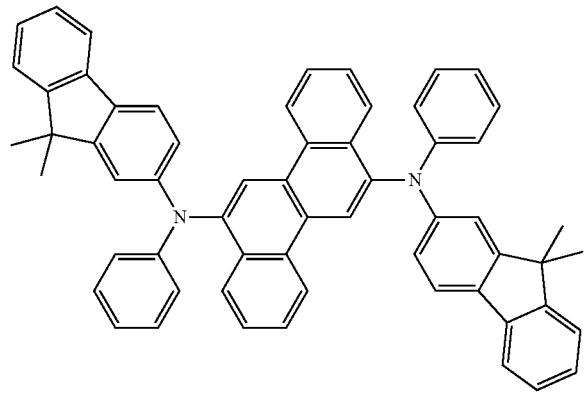

BD2 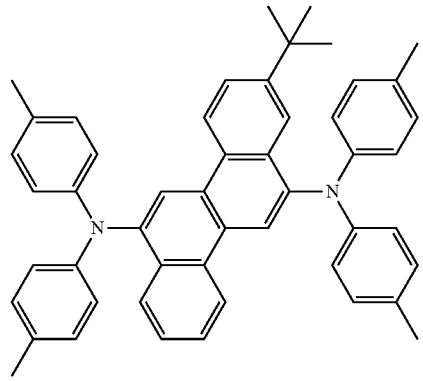

-continued
BD3
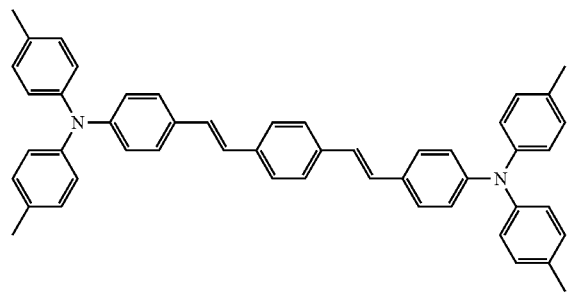
BD4
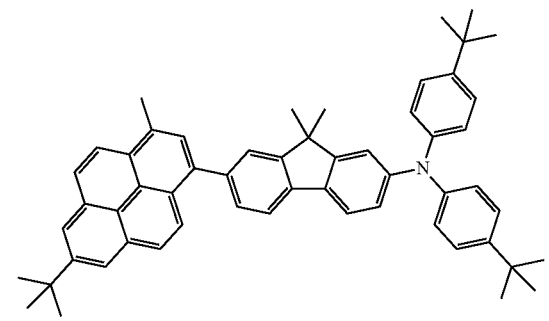
BD5
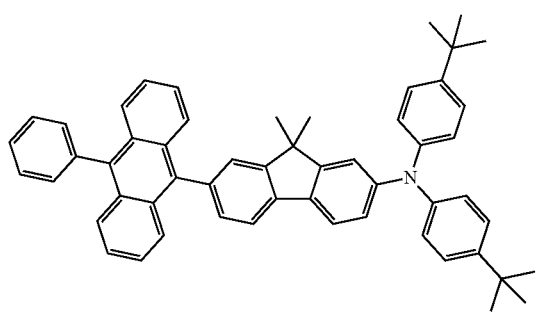
BD6
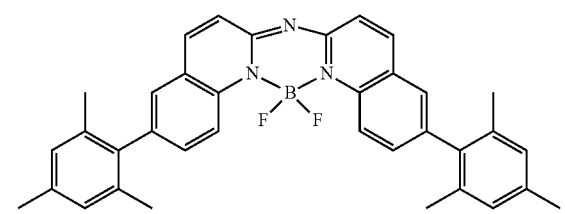
BD7
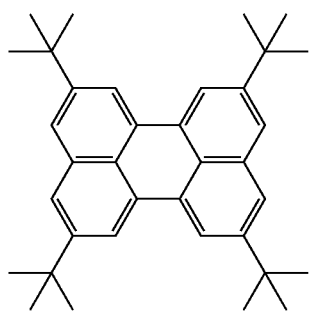
BD8
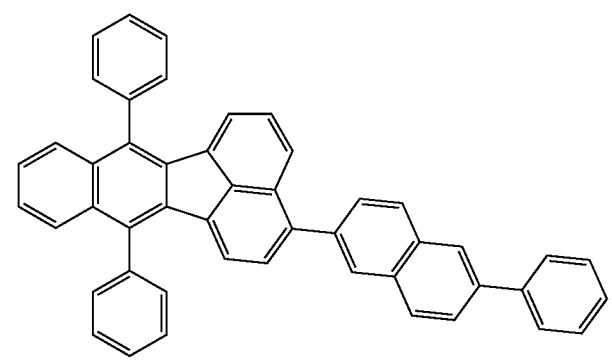
BD9
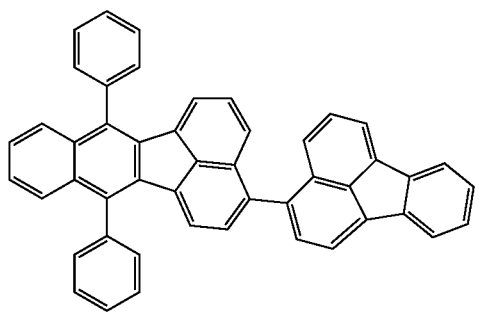
BD10
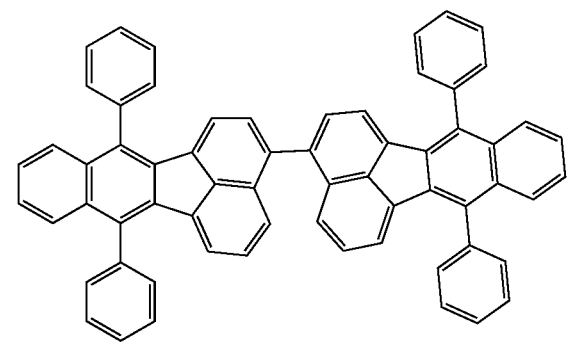

-continued
BD11
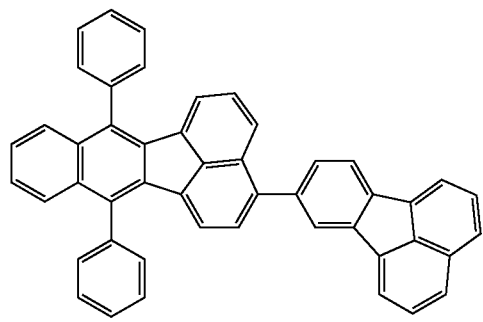
GD1
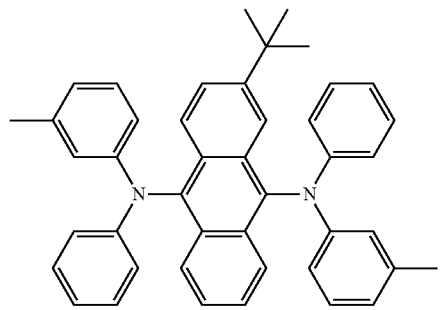
GD2
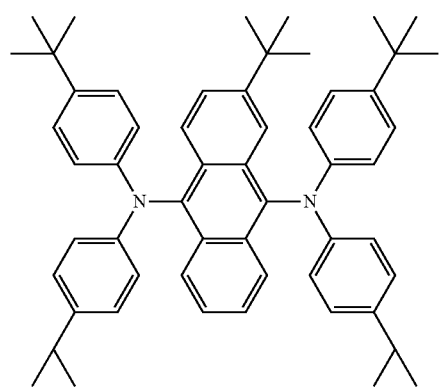
GD3
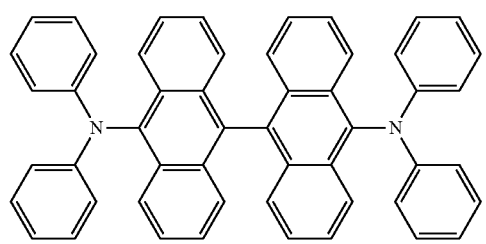
GD4
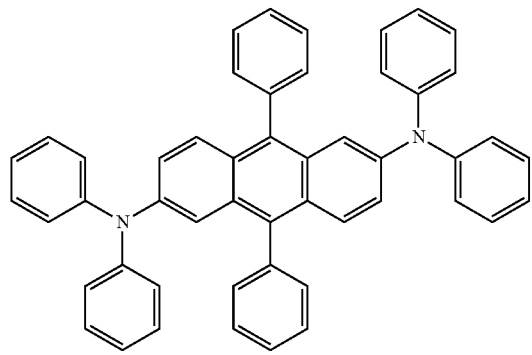
GD5
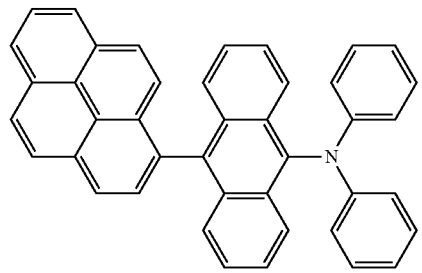
GD6
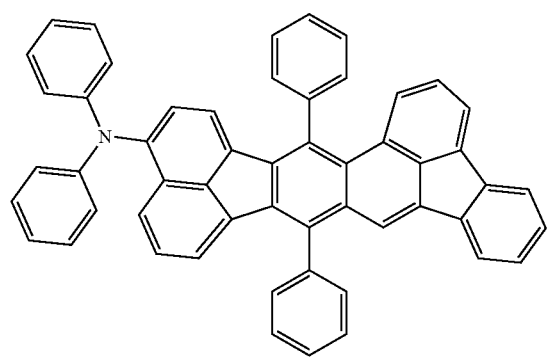
GD7
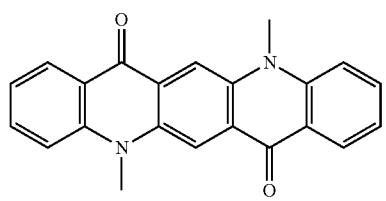

-continued
GD8
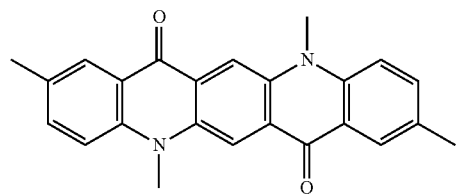
GD9
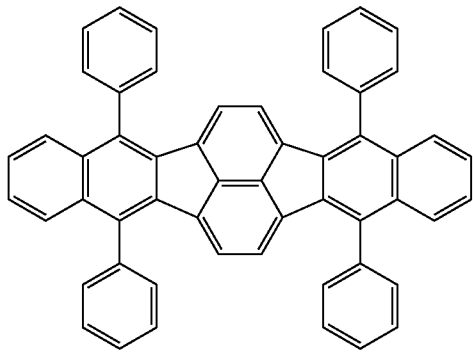
GD10
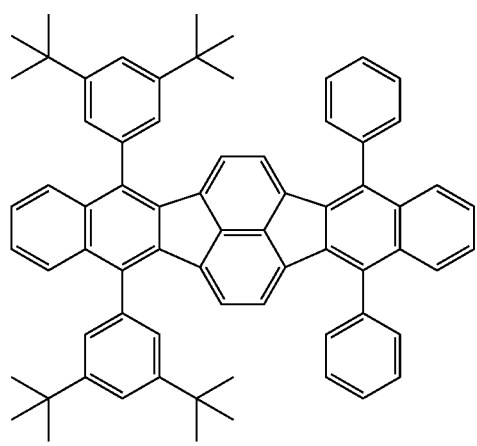
GD11
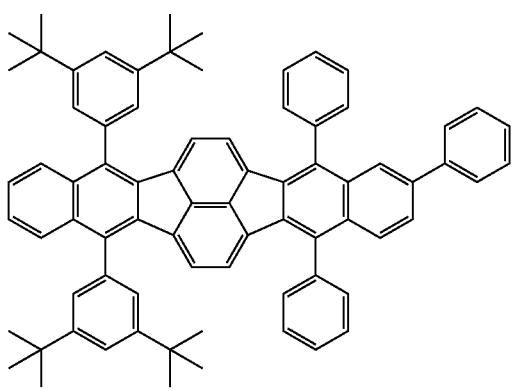
GD12
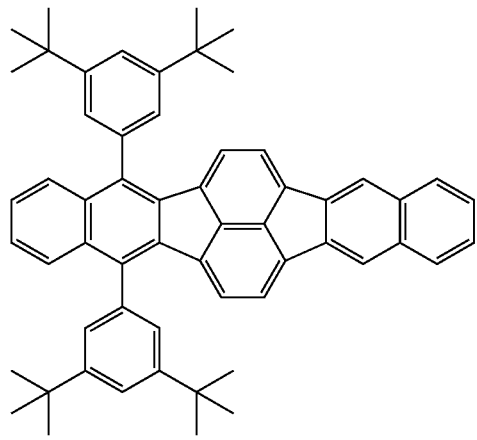
RD1
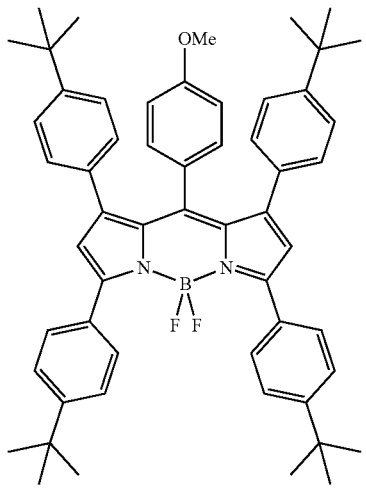
RD2
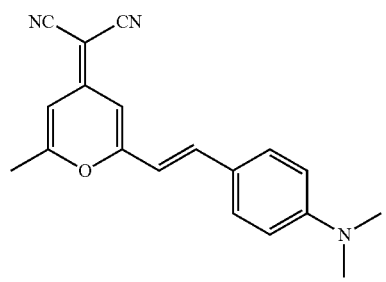

-continued

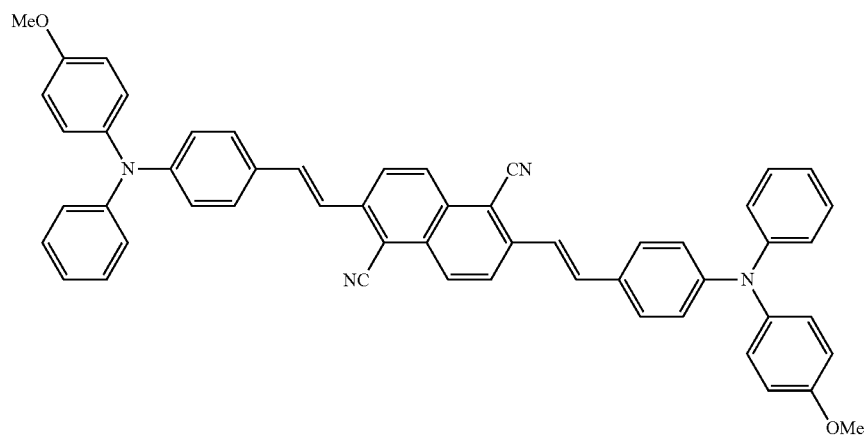
RD3

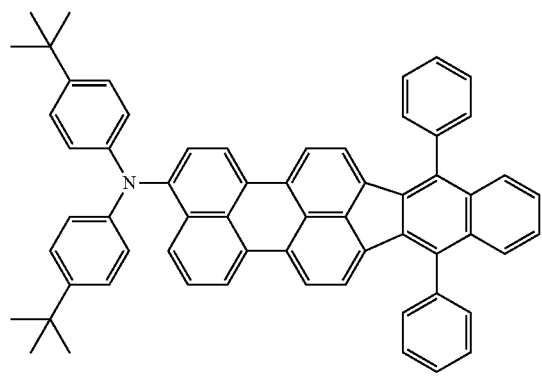
RD4

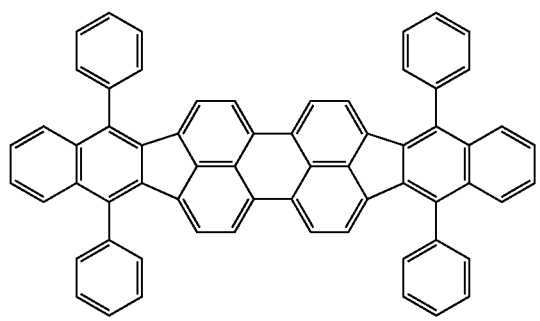
RD5

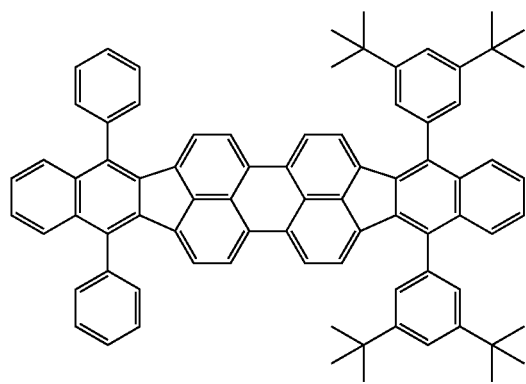
RD6

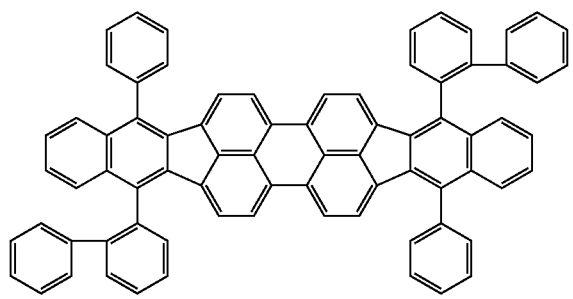
RD7

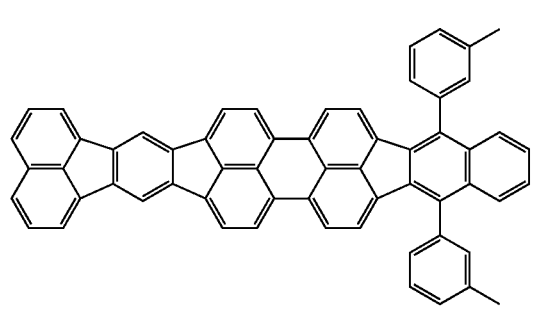
RD8

Examples of a light-emitting layer host or a light-emitting assist material in the light-emitting layer include aromatic hydrocarbon compounds and derivatives thereof, carbazole derivatives, dibenzofuran derivatives, dibenzothiophene derivatives, organoaluminum complexes, such as tris(8-quinolinolato) aluminum, and organic beryllium complexes.

The organic compound according to the present embodiment has low HOMO/LUMO energy, and the host material can also be formed of a hydrocarbon and have low HOMO/

LUMO energy. This is because a host material with a heteroatom, such as a nitrogen atom, has high HOMO/LUMO energy, which may result in the formation of a quenching component or a trap level, such as the formation of an exciplex with the organic compound according to the present embodiment.

In particular, the host material can have an anthracene, triphenylene, chrysene, fluoranthene, or pyrene skeleton in the molecular skeleton. This is because such a host material is composed of a hydrocarbon as described above and has S1 energy required for sufficient energy transfer to the organic compound according to the present embodiment.

Specific examples of a compound used as a light-emitting layer host or a light-emitting assist material in the light-emitting layer is described below. However, as a matter of course, the present disclosure is not limited to these examples.

EM1
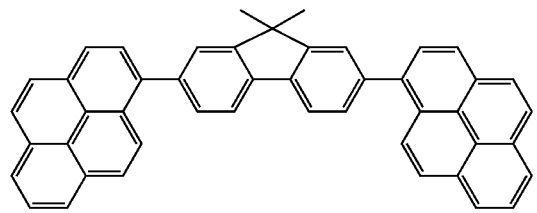

EM2
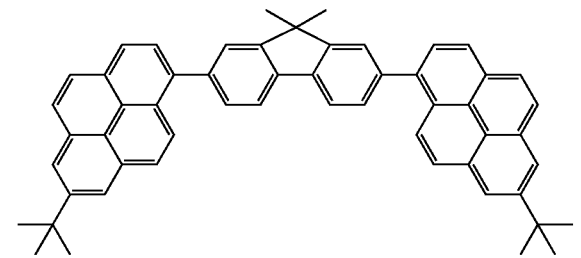

EM3
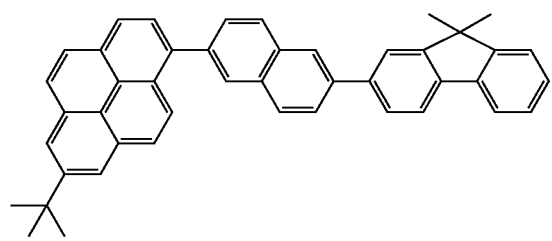

EM4
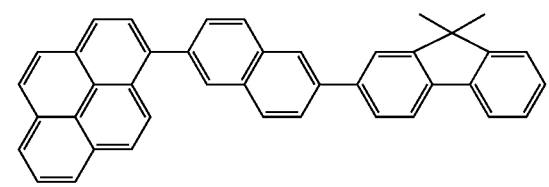

EM5
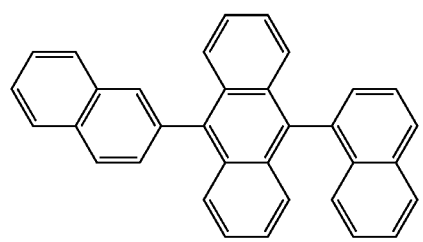

EM6
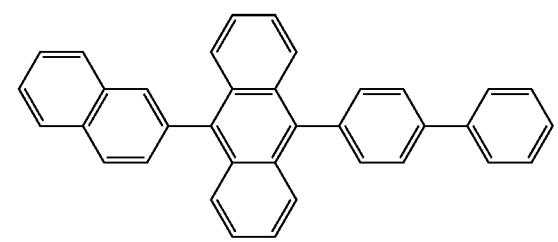

EM7
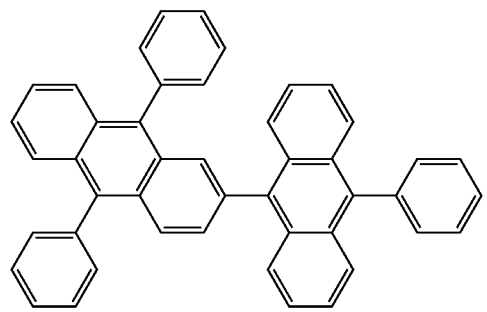

EM8
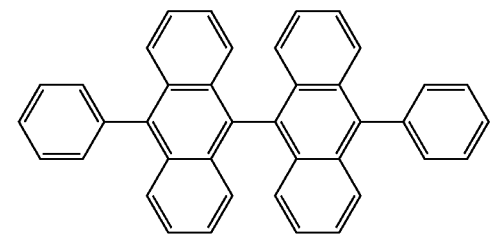

EM9
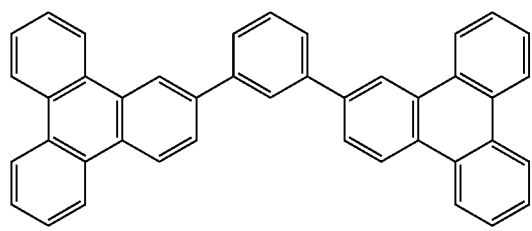

EM10
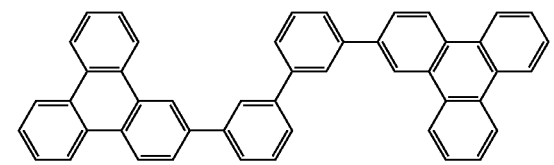

EM11
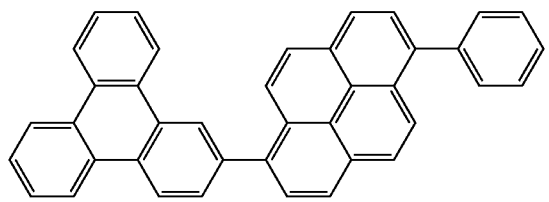
EM12
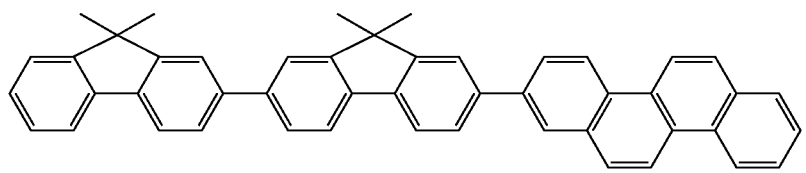
EM13
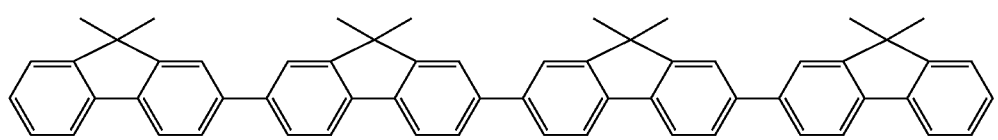
EM14
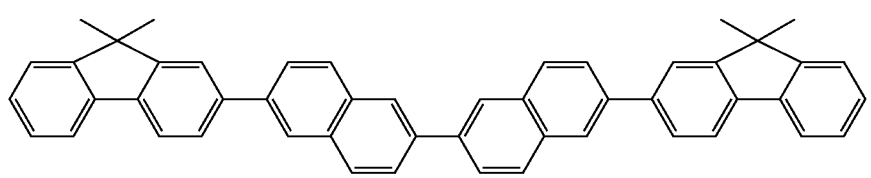
EM15
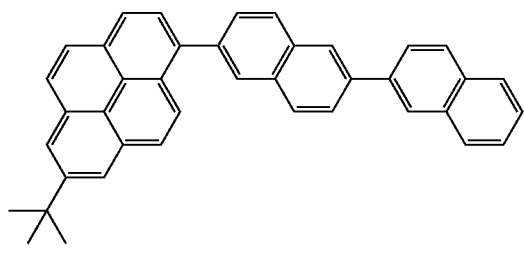
EM16
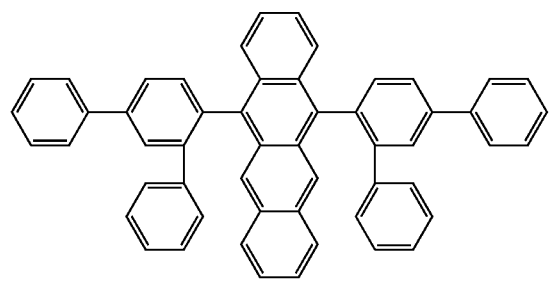
EM17
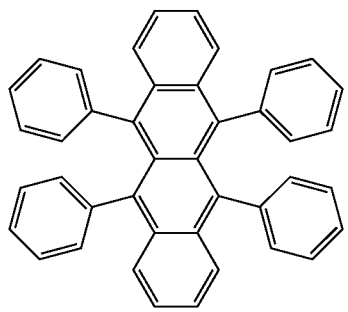
EM18
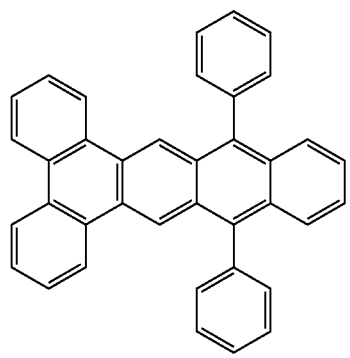

-continued
EM19
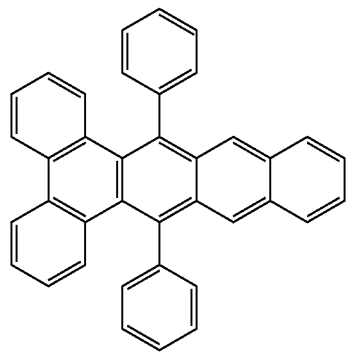
EM20
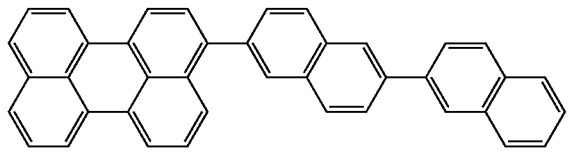
EM21
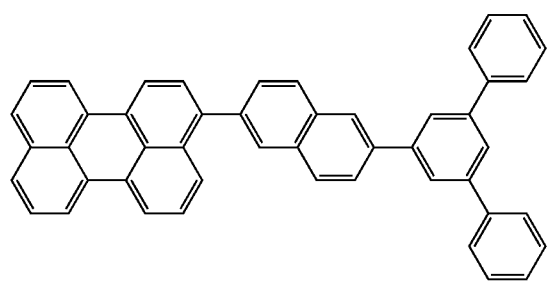
EM22
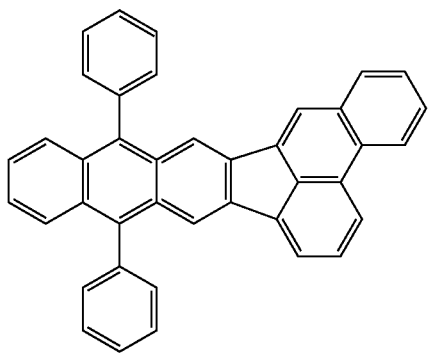
EM23
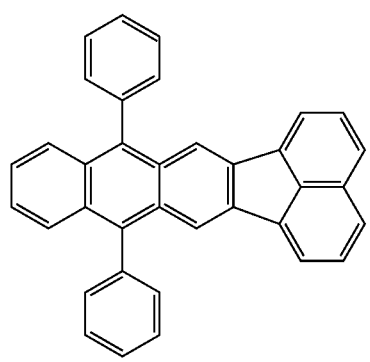
EM24
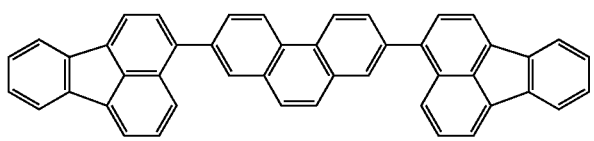
EM25
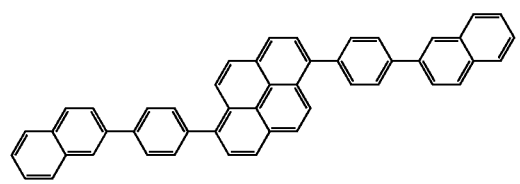
EM26
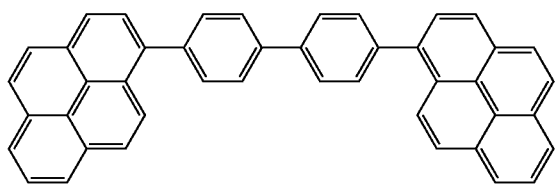
EM27
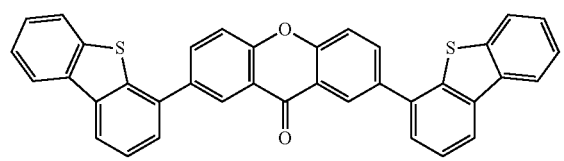
EM28
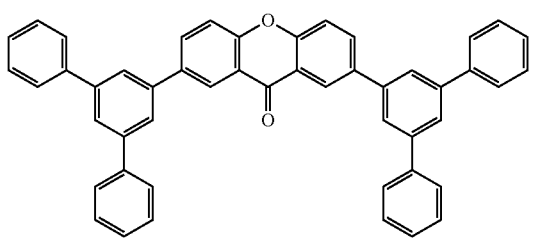

EM29
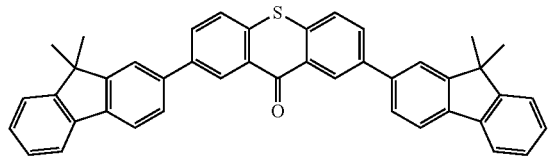

EM30
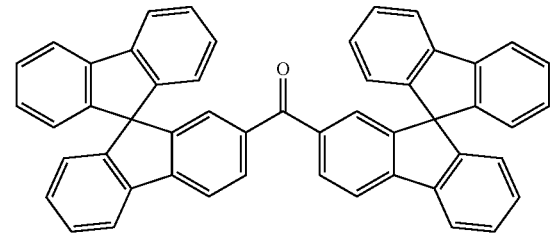

EM31
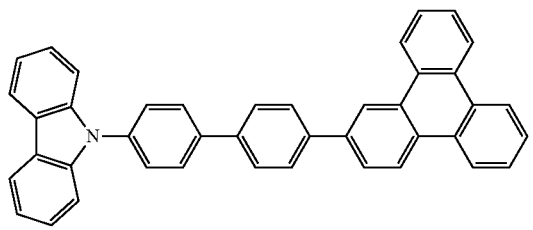

EM32
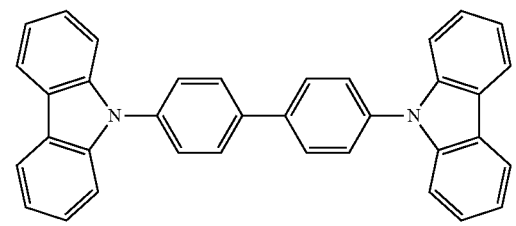

An electron-transport material can be selected from materials that can transport electrons injected from a negative electrode to the light-emitting layer and is selected in consideration of the balance with the hole mobility of the hole-transport material. Examples of materials with electron-transport ability include, but are not limited to, oxadiazole derivatives, oxazole derivatives, pyrazine derivatives, triazole derivatives, triazine derivatives, quinoline derivatives, quinoxaline derivatives, phenanthroline derivatives, organoaluminum complexes, and fused-ring compounds (for example, fluorene derivatives, naphthalene derivatives, chrysene derivatives, and anthracene derivatives). Furthermore, the electron-transport material is also suitable for a hole-blocking layer. Specific examples of compounds that can be used as the electron-transport material are described below. As a matter of course, the present disclosure is not limited to these compounds.

ET1
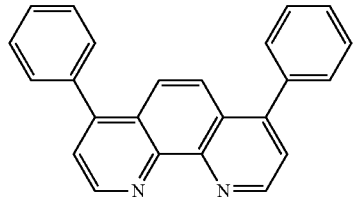

ET2
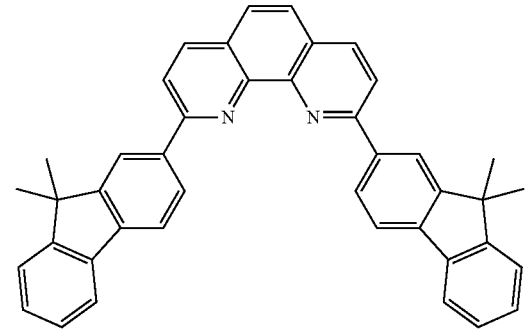

ET3
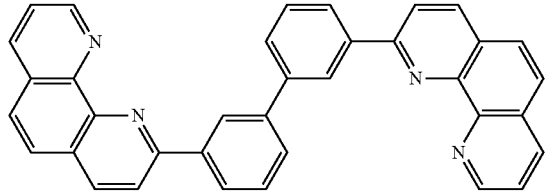

ET4
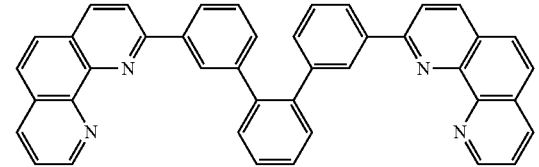

ET5
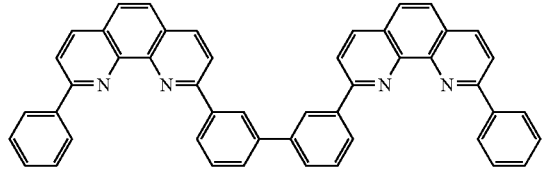

ET6
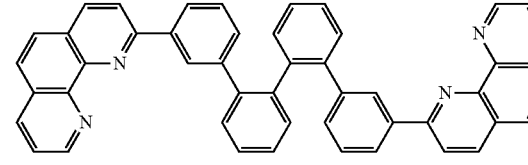

-continued
101
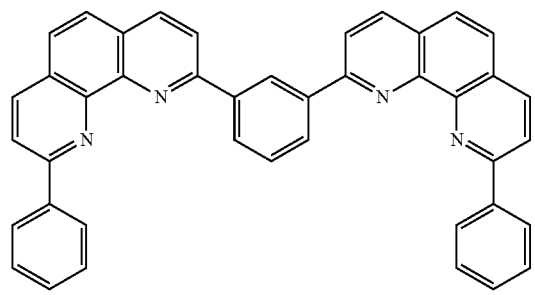
102
ET7
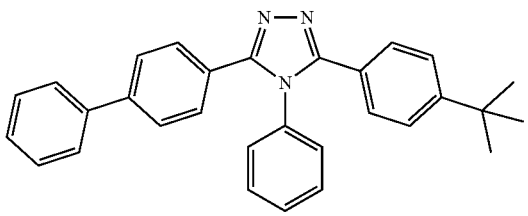
ET8
ET9
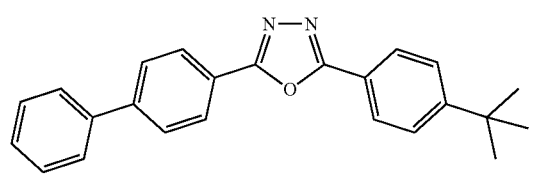
ET10
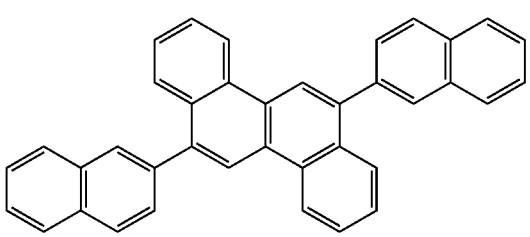
ET11
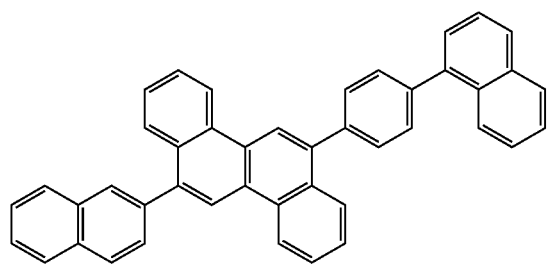
ET12
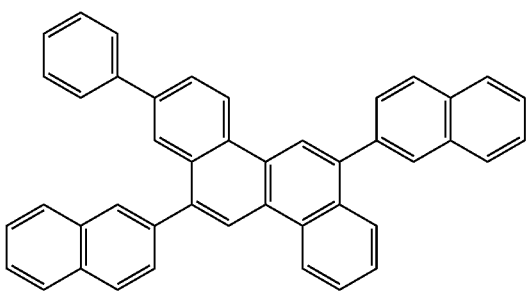
ET13
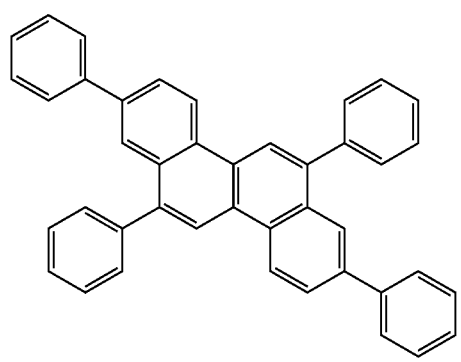
ET14
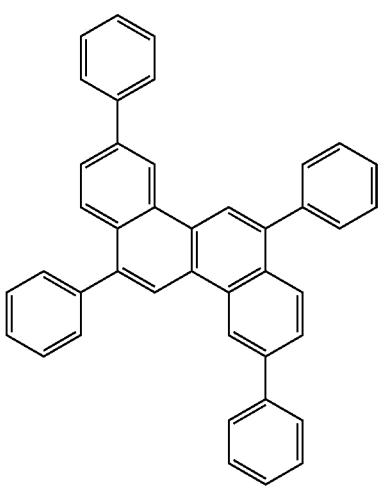

-continued
ET15
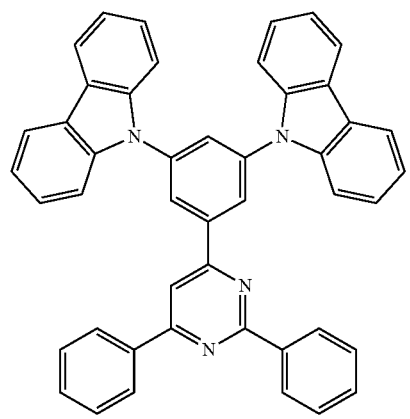
ET16
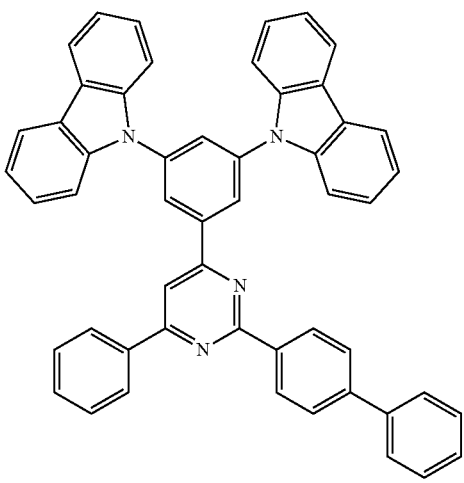
ET17
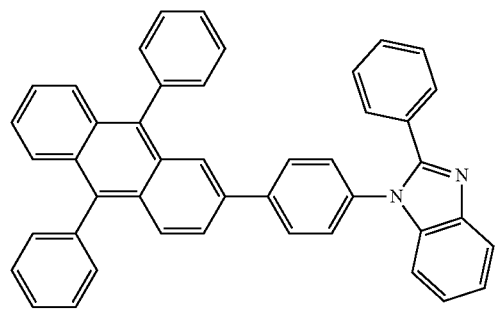
ET18
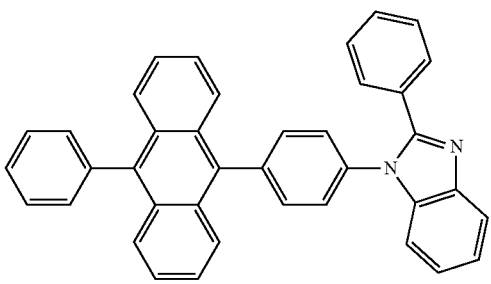
ET19
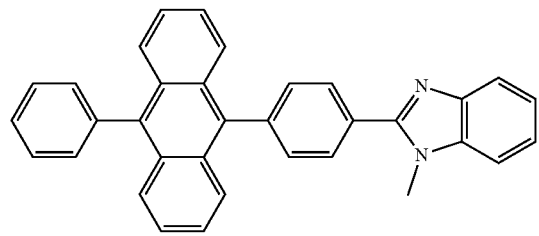
ET20
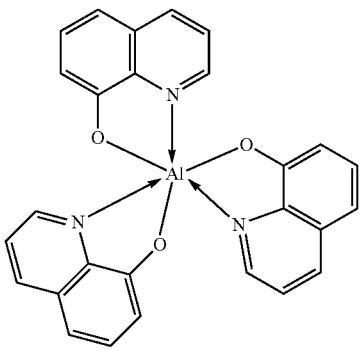
ET21
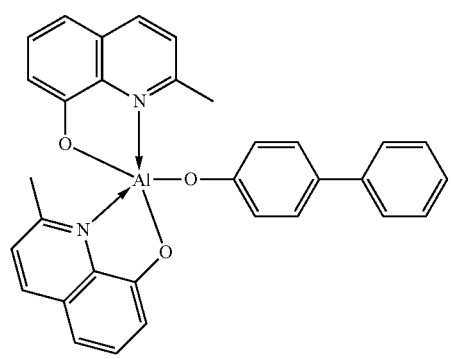
ET22
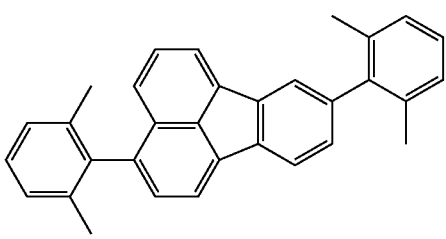

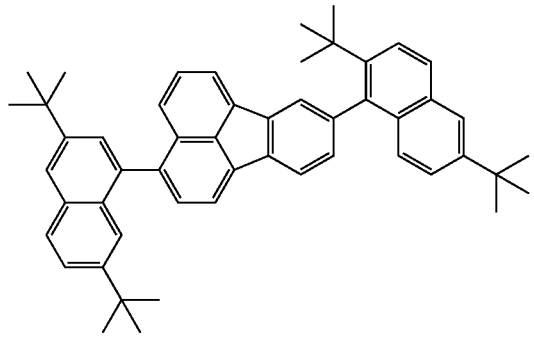

ET23

<Structure of Organic Light-Emitting Device>

An organic light-emitting device includes a positive electrode, an organic compound layer, and a negative electrode on a substrate. A protective layer, a color filter, or the like may be provided on the negative electrode. When a color filter is provided, a planarization layer may be provided between the color filter and a protective layer. The planarization layer may be composed of an acrylic resin or the like.

[Substrate]

The substrate may be formed of quartz, glass, silicon wafer, resin, metal, or the like. The substrate may have a switching device, such as a transistor, and a wire, on which an insulating layer may be provided. The insulating layer may be composed of any material, provided that the insulating layer can have a contact hole to ensure electrical connection between the positive electrode and the wire and is insulated from unconnected wires. For example, the insulating layer may be formed of a resin, such as polyimide, silicon oxide, or silicon nitride.

[Electrode]

A pair of electrodes can be used as the electrodes. The pair of electrodes may be a positive electrode and a negative electrode. When an electric field is applied in a direction in which the organic light-emitting device emits light, an electrode with a high electric potential is a positive electrode, and the other electrode is a negative electrode. In other words, the electrode that supplies holes to the light-emitting layer is a positive electrode, and the electrode that supplies electrons is a negative electrode.

A constituent material of the positive electrode can have as large a work function as possible. Examples of the constituent material include, but are not limited to, metallic elements, such as gold, platinum, silver, copper, nickel, palladium, cobalt, selenium, vanadium, and tungsten, mixtures thereof, alloys thereof, and metal oxides, such as tin oxide, zinc oxide, indium oxide, indium tin oxide (ITO), and indium zinc oxide. Electrically conductive polymers, such as polyaniline, polypyrrole, and polythiophene, may also be used.

These electrode materials may be used alone or in combination. The positive electrode may be monolayer or multilayer.

When used as a reflective electrode, for example, chromium, aluminum, silver, titanium, tungsten, molybdenum, an alloy thereof, or a laminate thereof can be used. When used as a transparent electrode, an oxide transparent conductive layer, such as indium tin oxide (ITO) or indium zinc oxide, can be used. However, the present disclosure is not limited to these. The electrodes may be formed by photolithography.

A constituent material of the negative electrode can be a material with a small work function. For example, an alkali metal, such as lithium, an alkaline-earth metal, such as calcium, a metallic element, such as aluminum, titanium, manganese, silver, lead, or chromium, or a mixture thereof may be used. An alloy of these metallic elements may also be used. For example, magnesium-silver, aluminum-lithium, aluminum-magnesium, silver-copper, or zinc-silver may be used. A metal oxide, such as indium tin oxide (ITO), may also be used. These electrode materials may be used alone or in combination. The negative electrode may have a monolayer or multilayer structure. Among them, silver can be used, and a silver alloy can be used to reduce the aggregation of silver. As long as the aggregation of silver can be reduced, the alloy may have any ratio. For example, it may be 1:1.

The negative electrode may be an oxide conductive layer, such as ITO, for a top emission device or may be a reflective electrode, such as aluminum (Al), for a bottom emission device. The negative electrode may be formed by any method. A direct-current or alternating-current sputtering method can achieve good film coverage and easily decrease resistance.

[Protective Layer]

A protective layer may be provided on the negative electrode. For example, a glass sheet with a moisture absorbent may be attached to the negative electrode to prevent water or the like from entering the organic compound layer and reduce the occurrence of display defects. In another embodiment, a passivation film, such as silicon nitride, may be provided on the negative electrode to prevent water or the like from entering the organic compound layer. For example, after the negative electrode is formed, the negative electrode is transferred to another chamber without breaking the vacuum, and a silicon nitride film with a thickness of 2 μm may be formed as a protective layer by a CVD method. The protective layer may be formed by the CVD method followed by an atomic layer deposition (ALD) method.

[Color Filter]

A color filter may be provided on the protective layer. For example, a color filter that matches the size of the organic light-emitting device may be provided on another substrate and may be bonded to the substrate on which the organic light-emitting device is provided, or a color filter may be patterned on the protective layer by photolithography. The color filter may be composed of a polymer.

[Planarization Layer]

A planarization layer may be provided between the color filter and the protective layer. The planarization layer may be composed of an organic compound and may be composed of a low-molecular-weight compound or a high-molecular-weight compound.

The planarization layer may be provided above and below the color filter, and the constituent materials thereof may be the same or different. Specific examples include polyvinylcarbazole resins, polycarbonate resins, polyester resins, ABS resins, acrylic resins, polyimide resins, phenolic resins, epoxy resins, silicone resins, and urea resins.

[Counter Substrate]

A counter substrate may be provided on the planarization layer. The counter substrate is so called because it faces the substrate. The counter substrate may be composed of the same material as the substrate.

[Organic Layer]

An organic compound layer (a hole-injection layer, a hole-transport layer, an electron-blocking layer, a light-emitting layer, a hole-blocking layer, an electron-transport layer, an electron-injection layer, etc.) constituting an organic light-emitting device according to an embodiment of the present disclosure is formed by the following method.

An organic compound layer constituting an organic light-emitting device according to an embodiment of the present disclosure can be formed by a dry process, such as a vacuum evaporation method, an ionized deposition method, sputtering, or plasma. Instead of the dry process, a wet process may also be employed in which a layer is formed by a known coating method (for example, spin coating, dipping, a casting method, an LB method, an ink jet method, etc.) using an appropriate solvent.

A layer formed by a vacuum evaporation method, a solution coating method, or the like undergoes little crystallization or the like and has high temporal stability. When a film is formed by a coating method, the film may also be formed in combination with an appropriate binder resin.

Examples of the binder resin include, but are not limited to, polyvinylcarbazole resins, polycarbonate resins, polyester resins, ABS resins, acrylic resins, polyimide resins, phenolic resins, epoxy resins, silicone resins, and urea resins.

These binder resins may be used alone as a homopolymer or a copolymer or may be used in combination. If necessary, an additive agent, such as a known plasticizer, antioxidant, and/or ultraviolet absorber, may also be used.

<Applications of Organic Light-Emitting Device According to Present Embodiment>

An organic light-emitting device according to an embodiment of the present disclosure can be used as a constituent of a display apparatus or a lighting apparatus. Other applications include an exposure light source of an electrophotographic image-forming apparatus, a backlight of a liquid crystal display, and a light-emitting apparatus with a color filter in a white light source.

The display apparatus may include an image input unit for inputting image information from an area CCD, a linear CCD, a memory card, or the like, may include an information processing unit for processing the input information, and may be an image-information-processing apparatus for displaying an input image on a display unit. The display apparatus may have a plurality of pixels, and at least one of the pixels includes the organic light-emitting device according to the present embodiment and a transistor coupled to the organic light-emitting device.

A display unit of an imaging apparatus or an ink jet printer may have a touch panel function. A driving system of the touch panel function may be, but is not limited to, an infrared ray system, an electrostatic capacitance system, a resistive film system, or an electromagnetic induction system. The display apparatus may be used as a display of a multifunction printer.

Next, the display apparatus according to the present embodiment is described with reference to the accompanying drawings. FIG. 1 is a schematic cross-sectional view of a display apparatus that includes an organic light-emitting device and a TFT device coupled to the organic light-emitting device. The TFT device is an example of an active device.

A display apparatus 10 in FIG. 1 includes a substrate 11, such as a glass sheet, and a moisture-proof film 12 on the substrate 11. The moisture-proof film 12 protects a TFT device or an organic compound layer. Reference numeral 13 denotes a metal gate electrode. Reference numeral 14 denotes a gate-insulating film, and reference numeral 15 denotes a semiconductor layer.

A TFT device 18 includes a semiconductor layer 15, a drain electrode 16, and a source electrode 17. The TFT device 18 is covered with an insulating film 19. A positive electrode 21 of an organic light-emitting device 26 is coupled to the source electrode 17 through a contact hole 20.

The method for electrically connecting the electrodes (the positive electrode 21 and a negative electrode 23) of the organic light-emitting device 26 to the electrodes (the source electrode 17 and the drain electrode 16) of the TFT device 18 is not limited to the embodiment illustrated in FIG. 1. More specifically, it is only necessary to electrically connect either the positive electrode 21 or the negative electrode 23 to either the source electrode 17 or the drain electrode 16 of the TFT device 18.

Although an organic compound layer 22 is a single layer in the display apparatus 10 illustrated in FIG. 1, the organic compound layer 22 may be composed of a plurality of layers. The negative electrode 23 is covered with a first protective layer 24 and a second protective layer 25 for preventing degradation of the organic light-emitting device 26.

Although the display apparatus 10 in FIG. 1 includes a transistor as a switching device, a MIM device may be used instead as the switching device.

The transistor used in the display apparatus 10 in FIG. 1 is not limited to a transistor including a single crystal silicon wafer and may also be a thin-film transistor including an active layer on an insulating surface of the substrate. The active layer may be single-crystal silicon, non-single-crystal silicon, such as amorphous silicon or microcrystalline silicon, or a non-single-crystal oxide semiconductor, such as indium zinc oxide or indium gallium zinc oxide. The thin-film transistor is also referred to as a TFT device.

The transistor in the display apparatus 10 of FIG. 1 may be formed within a substrate, such as a Si substrate. The phrase "formed within a substrate" means that the substrate, such as a Si substrate, itself is processed to form the transistor. Thus, the transistor within the substrate can be considered that the substrate and the transistor are integrally formed.

In the organic light-emitting device according to the present embodiment, the emission luminance is controlled with a TFT, which is an example of a switching device. The organic light-emitting device can be provided on a plurality of planes to display an image at each emission luminance. The switching device according to the present embodiment is not limited to the TFT and may be a transistor formed of low-temperature polysilicon or an active-matrix driver formed on a substrate, such as a Si substrate. "On a substrate" may also be referred to as "within a substrate".

Whether a transistor is provided within a substrate or a TFT is used depends on the size of a display unit. For example, for a display unit with approximately 0.5 inches, an organic light-emitting device can be provided on a Si substrate.

Figure 2:
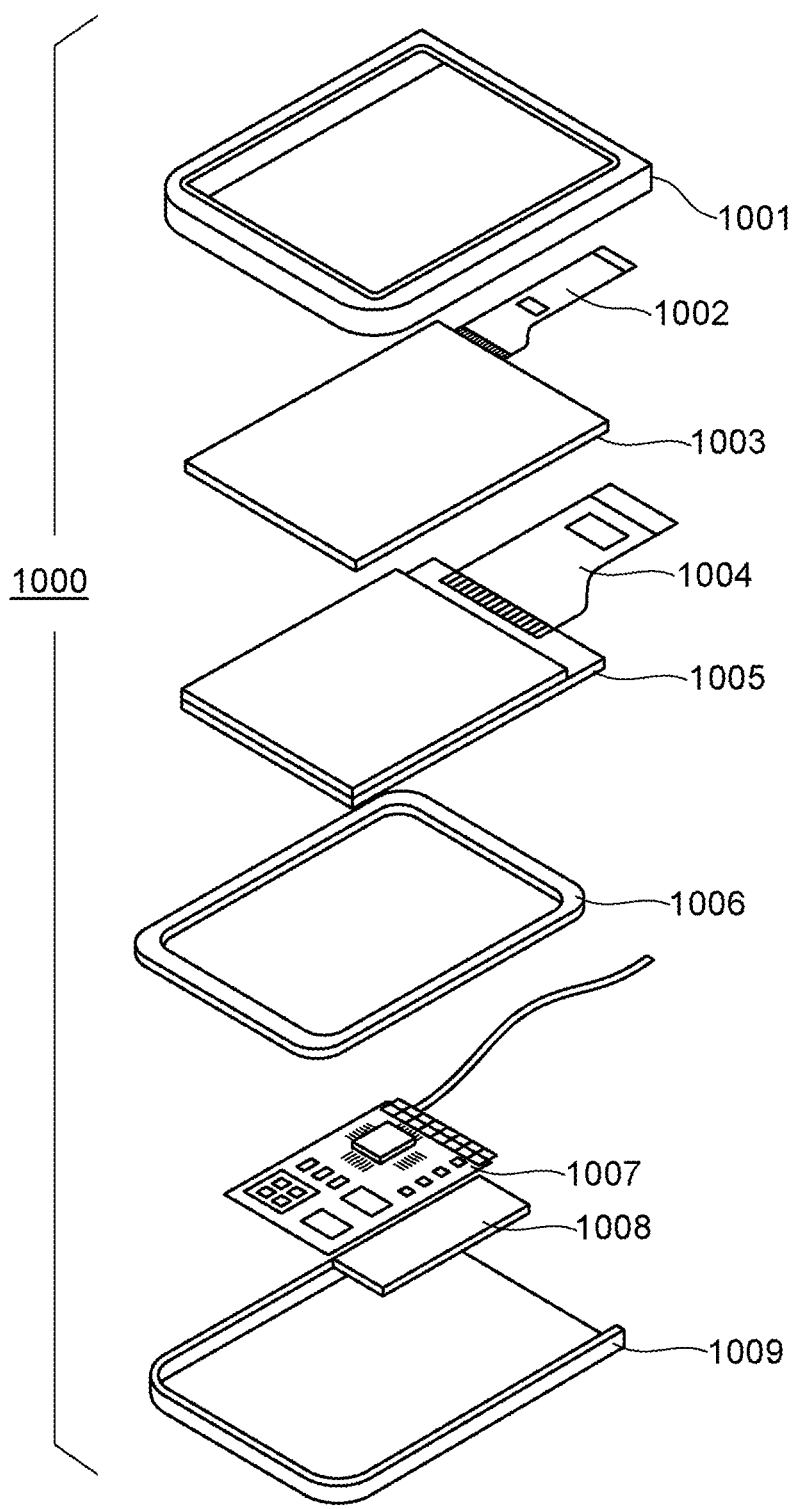
FIG. 2 is a schematic view of an example of a display apparatus according to an embodiment of the present disclosure.

FIG. 2 is a schematic view of an example of the display apparatus according to the present embodiment. A display apparatus 1000 may include a touch panel 1003, a display panel 1005, a frame 1006, a circuit substrate 1007, and a battery 1008 between an upper cover 1001 and a lower cover 1009. The touch panel 1003 and the display panel 1005 are coupled to flexible printed circuits FPC 1002 and 1004, respectively. Transistors are printed on the circuit substrate 1007. The battery 1008 may not be provided when the display apparatus is not a mobile device, or may be provided at another position even when the display apparatus is a mobile device.

The display apparatus according to the present embodiment may be used in a display unit of a photoelectric conversion apparatus, such as an imaging apparatus, that includes an optical unit with a plurality of lenses and an imaging device for receiving light passing through the optical unit. The imaging apparatus may include a display unit for displaying information acquired by the imaging device. The display unit may be a display unit exposed outside from the imaging apparatus or a display unit located in a finder. The imaging apparatus may be a digital camera or a digital video camera.

Figure 3A:
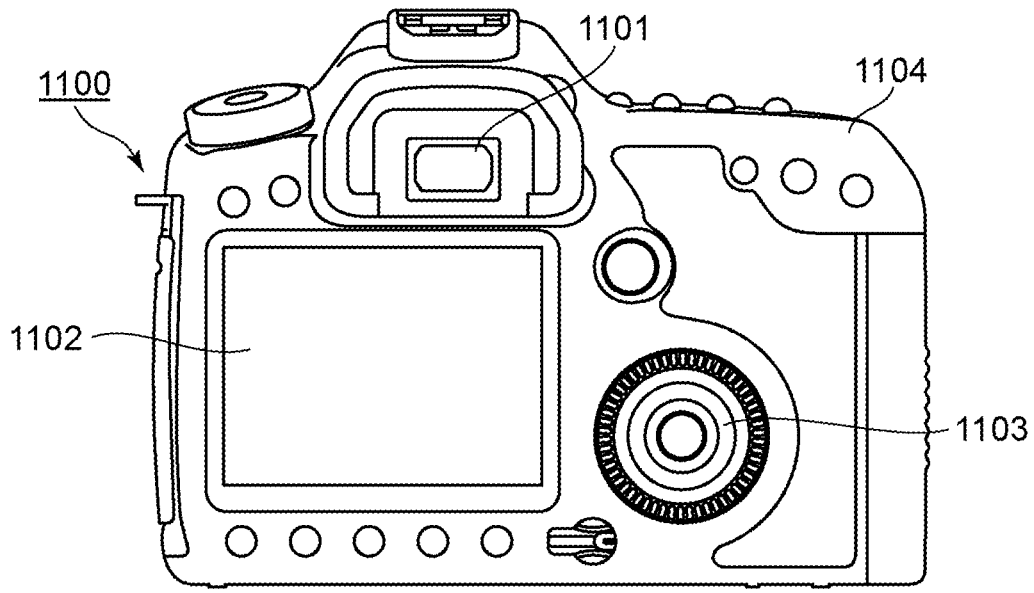
FIG. 3A is a schematic view of an example of an imaging apparatus according to an embodiment of the present disclosure.

FIG. 3A is a schematic view of an example of an imaging apparatus according to the present embodiment. An imaging apparatus 1100 may include a viewfinder 1101, a rear display 1102, an operating unit 1103, and a housing 1104. The viewfinder 1101 may include the display apparatus according to the present embodiment. In such a case, the display apparatus may display environmental information, imaging instructions, and the like as well as an image to be captured. The environmental information may include the intensity and direction of external light, the travel speed of the photographic subject, and the possibility that the subject is shielded by a shield, and the like.

Because the appropriate timing for imaging is a short time, it is better to display information as soon as possible. Thus, a display apparatus including the organic light-emitting device according to the present embodiment can be used. This is because the organic light-emitting device has a high response speed. A display apparatus including the organic light-emitting device can be more suitably used than these apparatuses and liquid crystal displays that require a high display speed.

The imaging apparatus 1100 includes an optical unit (not shown). The optical unit has a plurality of lenses and focuses an image on an imaging device in the housing 1104. The focus of the lenses can be adjusted by adjusting their relative positions. This operation can also be automatically performed.

The display apparatus according to the present embodiment may include color filters of red, green, and blue colors. The color filters may be arranged such that the red, green, and blue colors are arranged in a delta arrangement.

The display apparatus according to the present embodiment may be used for a display unit of electronic equipment, such as a mobile terminal. Such a display apparatus may have both a display function and an operation function. Examples of the mobile terminals include mobile phones, such as smartphones, tablets, and head-mounted displays.

Figure 3B:
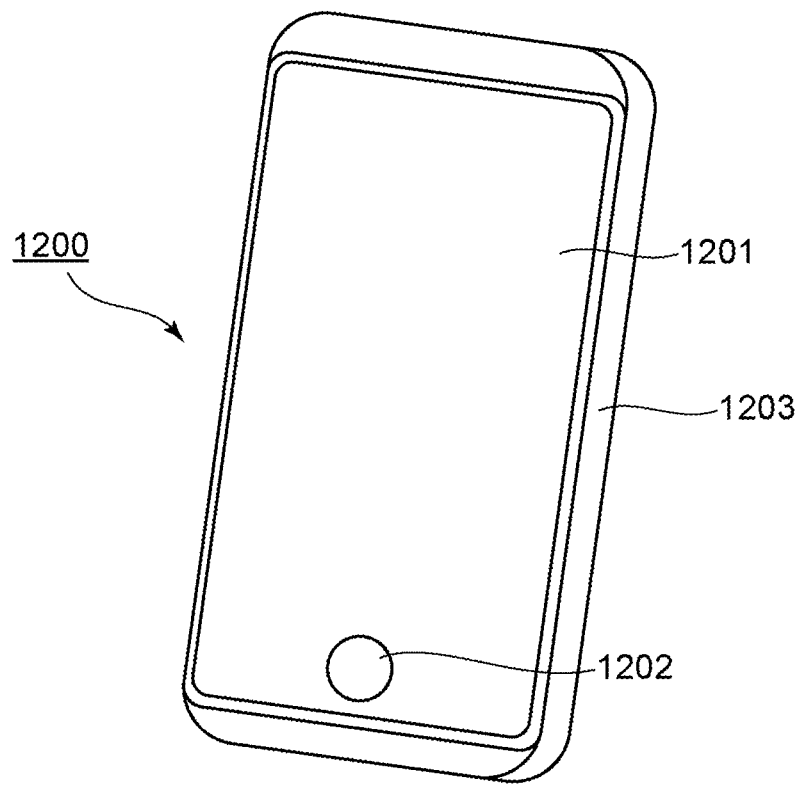
FIG. 3B is a schematic view of an example of electronic equipment according to an embodiment of the present disclosure.

FIG. 3B is a schematic view of an example of electronic equipment according to the present embodiment. Electronic equipment 1200 includes a display unit 1201, an operating unit 1202, and a housing 1203. The housing 1203 may include a circuit, a printed circuit board including the circuit, a battery, and a communication unit. The operation unit 1202 may be a button or a touch panel response unit. The operating unit may be a biometric recognition unit that recognizes a fingerprint and releases the lock. Electronic equipment including a communication unit may also be referred to as a communication apparatus.

Figure 4A:
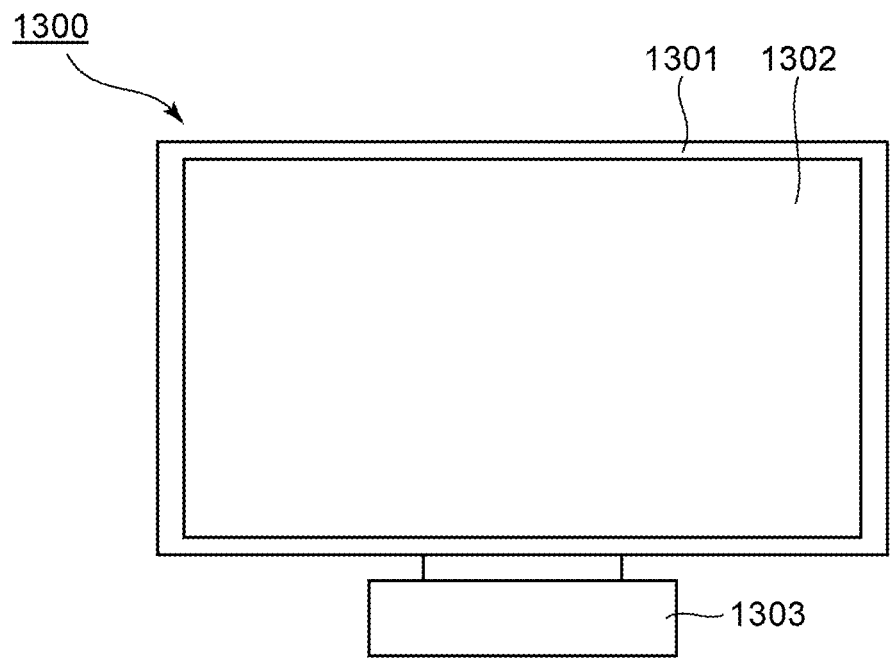
FIG. 4A is a schematic view of an example of a display apparatus according to an embodiment of the present disclosure.
Figure 4B:
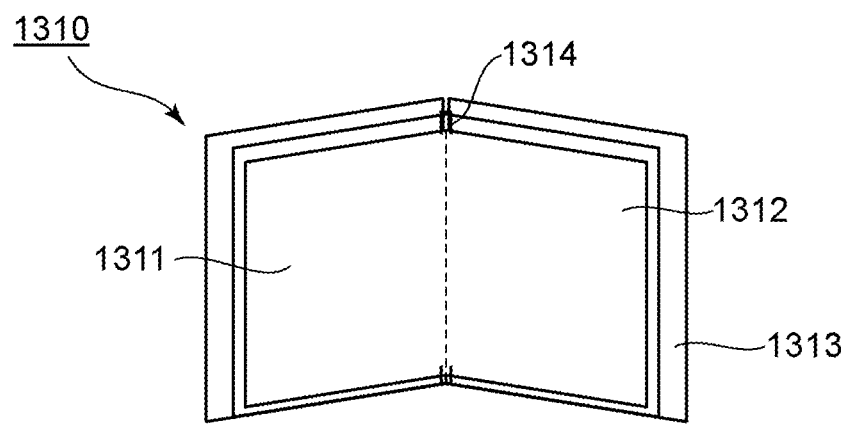
FIG. 4B is a schematic view of an example of a bendable display apparatus.

FIGS. 4A and 4B are schematic views of an example of the display apparatus according to the present embodiment. FIG. 4A illustrates a display apparatus, such as a television monitor or a PC monitor. A display apparatus 1300 includes a frame 1301 and a display unit 1302. The light-emitting apparatus according to the present embodiment may be used for the display unit 1302. The frame 1301 and the display unit 1302 are supported by a base 1303. The base 1303 is not limited to the structure illustrated in FIG. 4A. The lower side of the frame 1301 may also serve as the base. The frame 1301 and the display unit 1302 may be bent. The radius of curvature may range from 5000 to 6000 mm.

FIG. 4B is a schematic view of another example of the display apparatus according to the present embodiment. A display apparatus 1310 in FIG. 4B is configured to be foldable and is a so-called foldable display apparatus. The display apparatus 1310 includes a first display unit 1311, a second display unit 1312, a housing 1313, and a folding point 1314. The first display unit 1311 and the second display unit 1312 may include the light-emitting apparatus according to the present embodiment. The first display unit 1311 and the second display unit 1312 may be a single display apparatus without a joint. The first display unit 1311 and the second display unit 1312 can be divided by a folding point. The first display unit 1311 and the second display unit 1312 may display different images or one image.

Figure 5A:
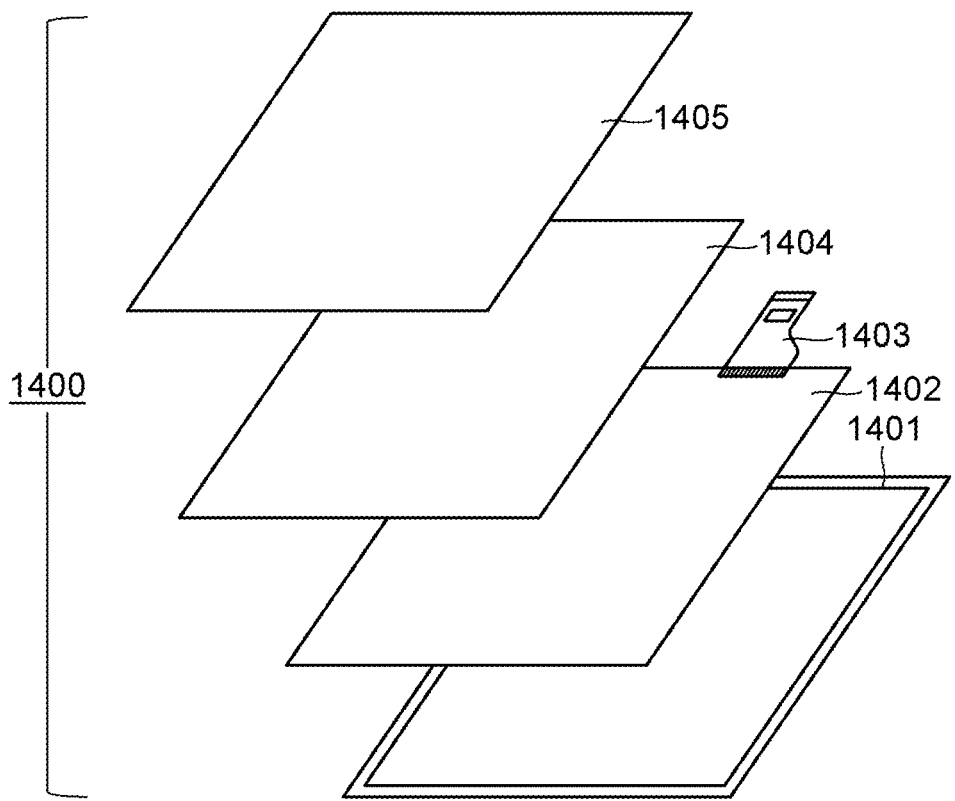
FIG. 5A is a schematic view of an example of a lighting apparatus according to an embodiment of the present disclosure.

FIG. 5A is a schematic view of an example of a lighting apparatus according to the present embodiment. A lighting apparatus 1400 may include a housing 1401, a light source 1402, a circuit substrate 1403, an optical filter 1404 that transmits light emitted by the light source 1402, and a light diffusing unit 1405. The light source 1402 may include the organic light-emitting device according to the present embodiment. The optical filter 1404 may be a filter that improves the color rendering properties of the light source. The light diffusing unit 1405 can effectively diffuse light from the light source and widely spread light as in illumination. The optical filter 1404 and the light diffusing unit 1405 may be provided on the light output side of the illumination. If necessary, a cover may be provided on the outermost side.

For example, the lighting apparatus is an interior lighting apparatus. The lighting apparatus may emit white light, neutral white light, or light of any color from blue to red. The lighting apparatus may have a light control circuit for controlling such light. The lighting apparatus may include the organic light-emitting device according to the present embodiment and a power supply circuit coupled thereto. The power supply circuit converts an AC voltage to a DC voltage. White has a color temperature of 4200 K, and neutral white has a color temperature of 5000 K. The lighting apparatus may have a color filter.

The lighting apparatus according to the present embodiment may include a heat dissipation unit. The heat dissipation unit releases heat from the apparatus to the outside and may be a metal or liquid silicon with a high specific heat.

Figure 5B:
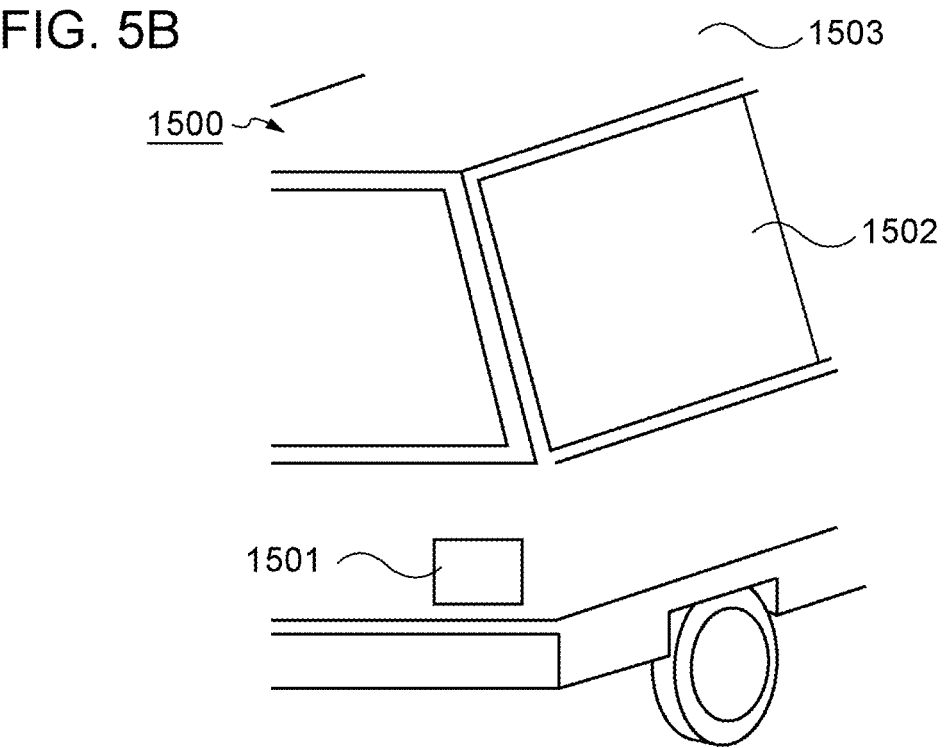
FIG. 5B is a schematic view of an example of an automobile with a vehicle lamp according to an embodiment of the present disclosure.

FIG. 5B is a schematic view of an automobile as an example of a moving body according to the present embodiment. The automobile has a taillight as an example of a lamp. An automobile 1500 may have a taillight 1501, which comes on when a brake operation or the like is performed.

The taillight 1501 may include the organic light-emitting device according to the present embodiment. The taillight 1501 may include a protective member for protecting the organic light-emitting device. The protective member may be formed of any transparent material with moderately high strength and can be formed of polycarbonate or the like. The polycarbonate may be mixed with a furan dicarboxylic acid derivative, an acrylonitrile derivative, or the like.

The automobile 1500 may have a body 1503 and a window 1502 on the body 1503. The window 1502 may be a transparent display as long as it is not a window for checking the front and rear of the automobile. The transparent display may include the organic light-emitting device according to the present embodiment. In such a case, constituent materials, such as electrodes, in the organic light-emitting device are transparent materials.

The moving body according to the present embodiment may be a ship, an aircraft, a drone, or the like. The moving body may include a body and a lamp provided on the body. The lamp may emit light to indicate the position of the body. The lamp includes the organic light-emitting device according to the present embodiment.

Figure 6:
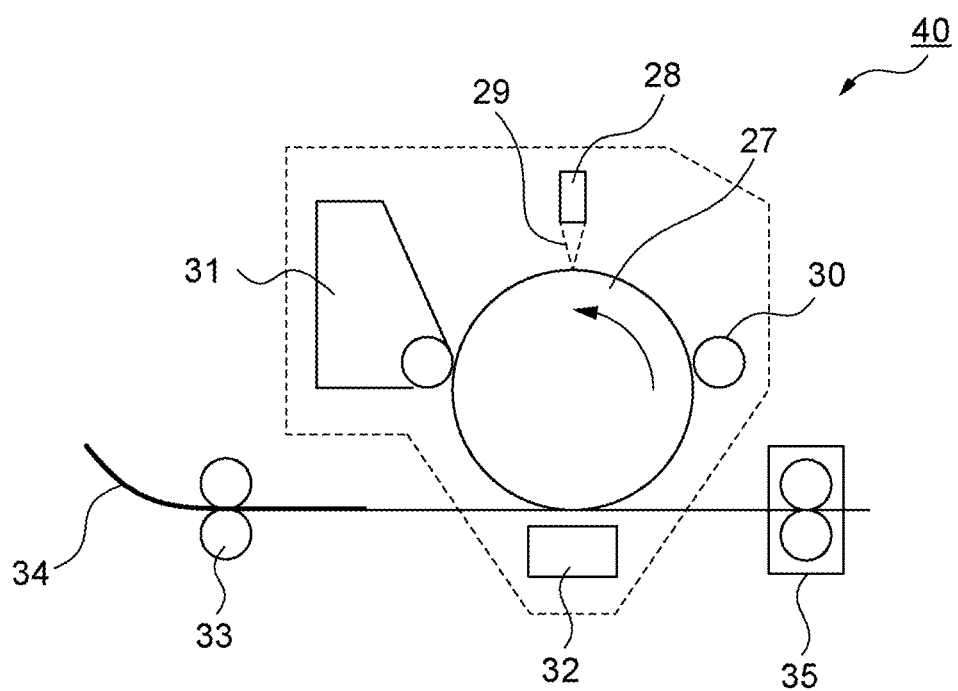
FIG. 6 is a schematic view of an example of an image-forming apparatus according to an embodiment of the present disclosure.

FIG. 6 is a schematic view of an example of an image-forming apparatus according to the present embodiment. An image-forming apparatus 40 is an electrophotographic image-forming apparatus and includes a photosensitive unit 27, an exposure light source 28, a charging unit 30, a developing unit 31, a transfer unit 32, a conveying roller 33, and a fixing unit 35. The exposure light source 28 emits light 29, and an electrostatic latent image is formed on the surface of the photosensitive unit 27. The exposure light source 28 includes the organic light-emitting device according to the present embodiment. The developing unit 31 contains toner and the like. The charging unit 30 electrifies the photosensitive unit 27. The transfer unit 32 transfers a developed image onto a recording medium 34. The conveying roller 33 conveys the recording medium 34. The recording medium 34 is paper, for example. The fixing unit 35 fixes an image on the recording medium 34.

Figure 7A:
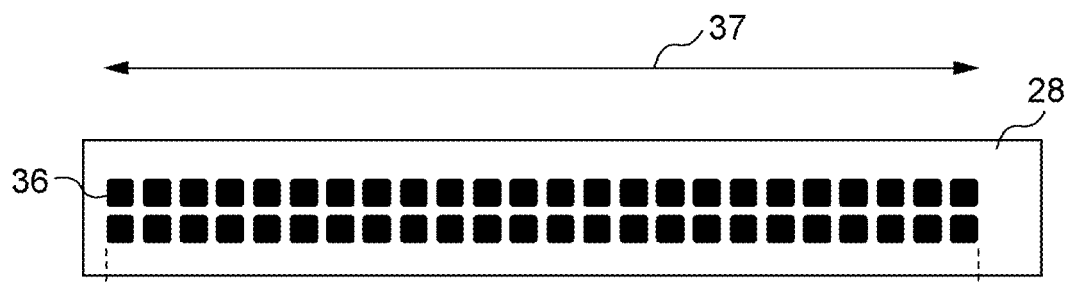
FIGS. 7A and 7B are schematic views of an example of an exposure light source of an image-forming apparatus according to an embodiment of the present disclosure.
Figure 7B:
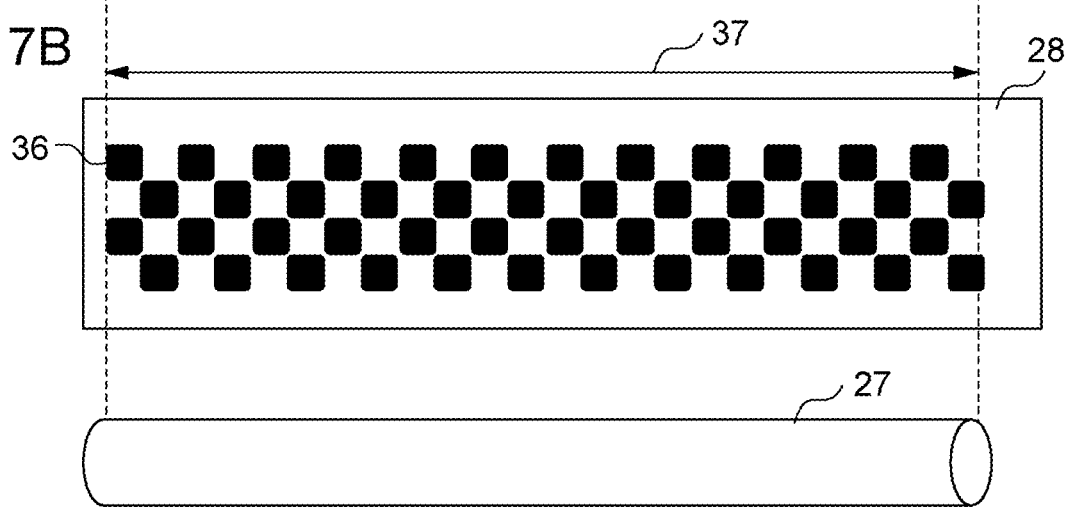

FIGS. 7A and 7B are schematic views of an exposure light source 28, wherein a plurality of light-emitting portions 36 are arranged on a long substrate. An arrow 37 indicates a longitudinal direction in which the organic light-emitting devices are arranged. The longitudinal direction is the same as the direction of the rotation axis of a photosensitive unit 27. This direction can also be referred to as the major-axis direction of the photosensitive unit 27. In FIG. 7A, the light-emitting portions 36 are arranged in the major-axis direction of the photosensitive unit 27. In FIG. 7B, unlike FIG. 7A, the light-emitting portions 36 are alternately arranged in the longitudinal direction in the first and second rows. The first row and the second row are arranged at different positions in the transverse direction. In the first row, the light-emitting portions 36 are arranged at intervals. In the second row, the light-emitting portions 36 are arranged at positions corresponding to the spaces between the light-emitting portions 36 of the first row. Thus, the light-emitting portions 36 are also arranged at intervals in the transverse direction. The arrangement in FIG. 7B can be referred to as a grid-like pattern, a staggered pattern, or a checkered pattern, for example.

As described above, the apparatus including the organic light-emitting device according to the present embodiment can be used to stably display a high-quality image for extended periods.

EXAMPLES

The present disclosure is described below with exemplary embodiments. However, the present disclosure is not limited to these exemplary embodiments.

Exemplary Embodiment 1 (Synthesis of Exemplary Compounds A1 and A2)

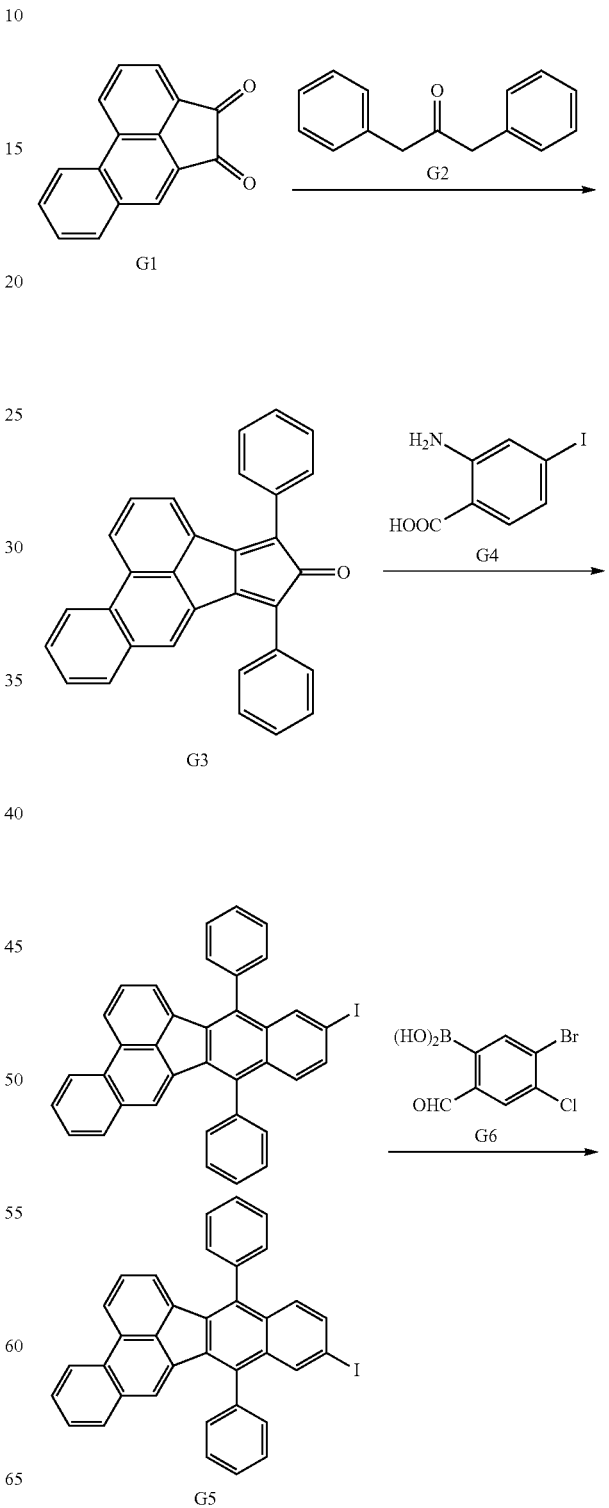

113
-continued
114
-continued
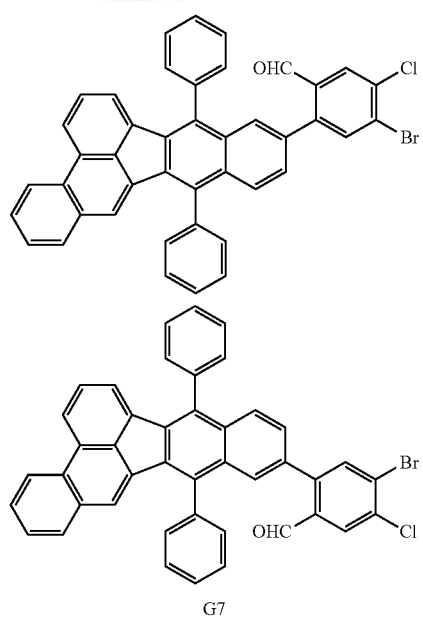
G7
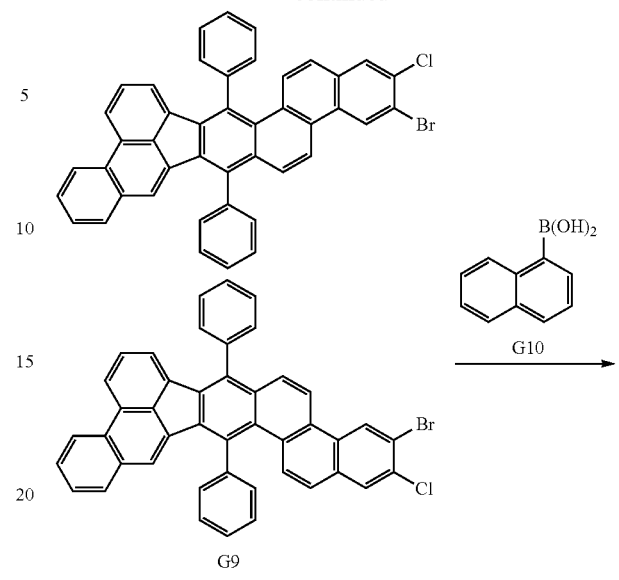
G9
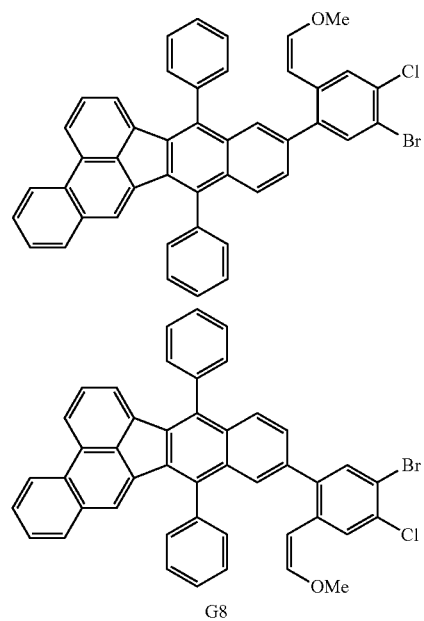
G8
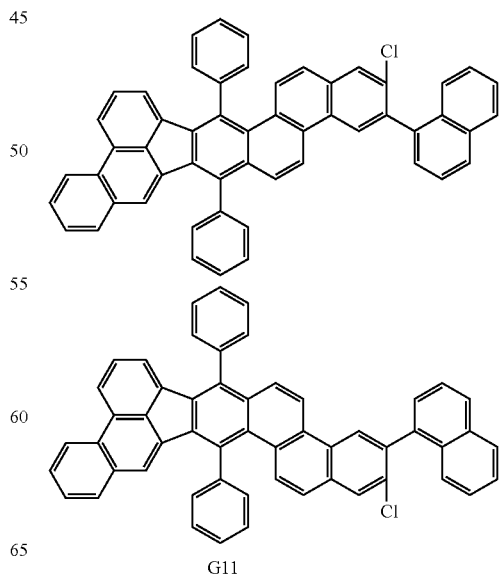
G11

-continued

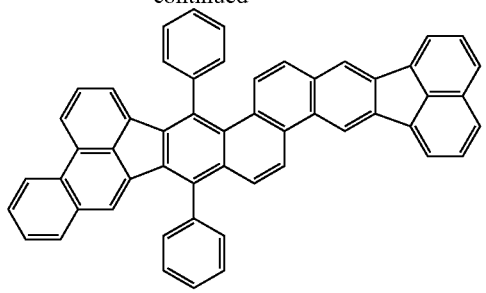

A1

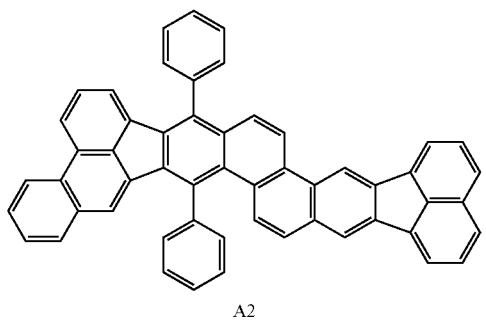

A2

(1) Synthesis of Compound G3

A 200-ml recovery flask was charged with the following reagents and solvent.
Compound G1: 2.32 g (10 mmol)
Compound G2: 2.10 g (10 mmol)
Ethanol: 100 ml Next, the reaction solution was heated to 70° C. in a nitrogen stream, and a KOH ethanol solution was added dropwise to the reaction solution. The reaction solution was stirred at this temperature (70° C.) for 6 hours. After completion of the reaction, water was added to the product, and the precipitate was filtered. The filter cake was subjected to dispersion washing with methanol. Thus, 3.04 g (yield: 75%) of a gray compound G3 was produced.

(2) Synthesis of Compound G5

A 100-ml recovery flask was charged with the following reagents and solvent.
Compound G3: 2.84 g (7 mmol)
Compound G4: 2.37 g (9 mmol)
Isoamyl nitrite: 1.05 g (9 mmol)
Toluene: 40 ml Next, the reaction solution was heated to 110° C. in a nitrogen stream and was stirred at this temperature (110° C.) for 3 hours. After completion of the reaction, the product was washed twice with 40 ml of water. The organic layer was washed with saturated saline, was dried over magnesium sulfate, and was filtered. The filtrate was concentrated. A brown liquid was produced. The brown liquid was purified by column chromatography (chloroform/heptane=1:4) and was then recrystallized in chloroform/methanol. Thus, 3.45 g (yield: 85%) of a yellow crystalline compound G5 was produced.

(3) Synthesis of Compound G7

A 200-ml recovery flask was charged with the following reagents and solvents.
Compound G5: 1.74 g (3 mmol)
Compound G6: 0.79 g (3 mmol)
Pd(PPh$_3$)$_4$: 0.03 g
Toluene: 50 ml
Ethanol: 20 ml
2 M aqueous sodium carbonate: 50 ml Next, the reaction solution was heated to 80° C. in a nitrogen stream and was stirred at this temperature (80° C.) for 6 hours. After completion of the reaction, water was added to the product for separation. The product was dissolved in chloroform, was purified by column chromatography (chloroform), and was recrystallized in chloroform/methanol. Thus, 1.51 g (yield: 75%) of a yellow crystalline compound G7 was produced.

(4) Synthesis of Compound G8

The following reagent and solvent in a 100-ml recovery flask were stirred in a nitrogen stream at room temperature for 30 minutes.
(Methoxymethyl)triphenylphosphonium chloride: 1.03 g (3 mmol)
THF: 10 ml Next, the following reagents were added in this order, and the mixture was stirred in a nitrogen stream at room temperature for 2 hours.
12% tetrahydrofuran solution of potassium tert-butoxide: 3 ml
Compound G7: 1.01 g (1.5 mmol)

After completion of the reaction, water and ethyl acetate were added to the reaction solution. Next, after the organic layer was recovered by a solvent extraction operation, the recovered organic layer was dried over sodium sulfate. Next, the solvent in the organic layer was distilled off under reduced pressure, and the residue was purified by silica gel column chromatography (mobile phase: toluene:heptane=1:1). Thus, 0.94 g (yield: 90%) of a compound G8 was produced as a pale yellow oil.

(5) Synthesis of Compound G9

The following reagent and solvent in a 200-ml recovery flask were stirred in a nitrogen stream at room temperature for 30 minutes.
Compound G8: 0.84 g (1.20 mmol)
Dichloromethane: 25 ml Next, the following reagent was added, and the mixture was stirred in a nitrogen stream at room temperature for 1 hour.
Methanesulfonic acid: 0.17 g (1.80 mmol)

After completion of the reaction, methanol was added to the reaction solution, and the precipitate was collected. The precipitate was purified by dispersion washing (solvent: methanol). Thus, 0.40 g (yield: 50%) of a compound G9 was produced as a pale yellow solid.

(6) Synthesis of Compound G11

A 200-ml recovery flask was charged with the following reagents and solvents.
Compound G9: 0.30 g (0.45 mmol)
Compound G10: 0.09 g (0.54 mmol)
Pd(PPh$_3$)$_4$: 0.005 g
Toluene: 50 ml
Ethanol: 20 ml
2 M aqueous sodium carbonate: 50 ml Next, the reaction solution was heated to 80° C. in a nitrogen stream and was stirred at this temperature (80° C.) for 6 hours. After completion of the reaction, water was added to the product for separation. The product was dissolved in chloroform, was purified by column chromatography (chloroform), and was recrystallized in chloroform/methanol. Thus, 0.24 g (yield: 75%) of a yellow crystalline compound G11 was produced.

(7) Synthesis of Exemplary Compounds A1 and A2

A 50-ml recovery flask was charged with the following reagents and solvent.
Compound G11: 214 mg (0.3 mmol)
Pd(dba)$_2$: 51 mg
Tricyclohexylphosphine (P(Cy)$_3$): 50 mg
Diazabicycloundecene (DBU): 114 mg
DMF: 5 ml Next, the reaction solution was heated to 145° C. in a nitrogen stream and was stirred at this temperature (145° C.) for 6 hours. After completion of the reaction, ethanol was added to precipitate crystals. The crystals were separated by filtration and were subjected to dispersion washing successively with water, ethanol, and heptane. The resulting yellowish brown crystals were then heated and dissolved in toluene, were subjected to hot filtration, and were recrystallized in toluene/methanol. Thus, 122 mg (yield: 60%) of a yellow solid was produced.

The resulting compound was a mixture of exemplary compounds A1 and A2, and the mixture had a purity of 99% or more as measured by HPLC.

The compound was subjected to mass spectrometry with a MALDI-TOF-MS (Autofle x LRF manufactured by Bruker).

[MALDI-TOF-MS]

Actual value: m/z=678.75 Calculated value: $C_{54}H_{30}$=678.83

<Exemplary Embodiment 2 (Synthesis of Exemplary Compounds A3 and A4)>

A mixture of exemplary compounds A3 and A4 was prepared in the same manner as in Exemplary Embodiment 1 except that the following compound G12 was used instead of the compound G2.

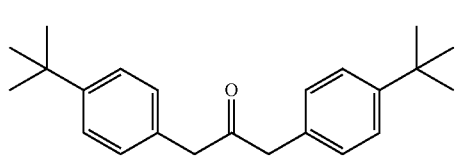

G12

The mixture had a purity of 98% or more as measured by HPLC. Mass spectrometry was performed with the MALDI-TOF-MS used in Exemplary Embodiment 1.

[MALDI-TOF-MS]

Actual value: m/z=903.43 Calculated value: $C_{70}H_{32}$=903.27

Exemplary Embodiment 3 (Synthesis of Exemplary Compounds C16 and C17)

A mixture of exemplary compounds C16 and C17 was prepared in the same manner as in Exemplary Embodiment 1 except that the following compound G13 was used instead of the compound G2, and the following compound G14 was used instead of the compound G10.

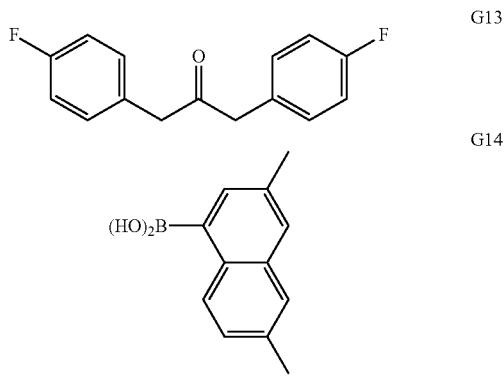

G13

G14

The mixture had a purity of 98% or more as measured by HPLC. Mass spectrometry was performed with the MALDI-TOF-MS used in Exemplary Embodiment 1.

[MALDI-TOF-MS]

Actual value: m/z=742.42 Calculated value: $C_{56}H_{32}F_2$=742.87

Comparative Example 1 (Synthesis of Comparative Compound (2))

A comparative compound (2) was prepared in the same manner as in Exemplary Embodiment 1 except that the following compound G15 was used instead of the compound G1.

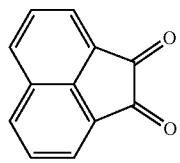

G15

The compound had a purity of 98% or more as measured by HPLC. Mass spectrometry was performed with the MALDI-TOF-MS used in Exemplary Embodiment 1.

[MALDI-TOF-MS]

Actual value: m/z=628.85 Calculated value: $C_{50}H_{28}$=628.77

Exemplary Embodiment 4 (Synthesis of Exemplary Compound A19)

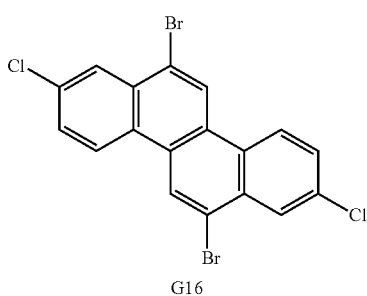

G16

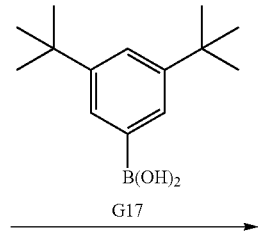

G17

-continued
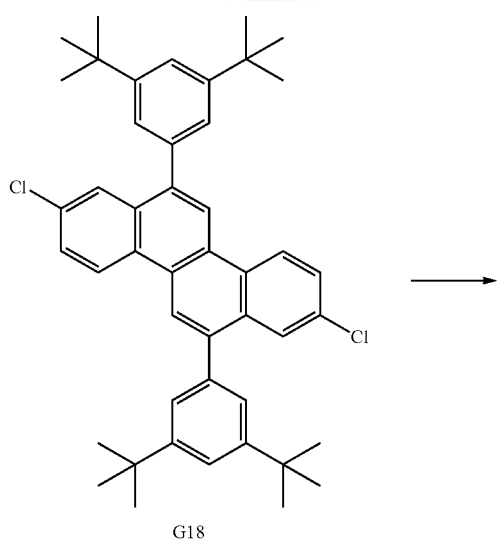
G18
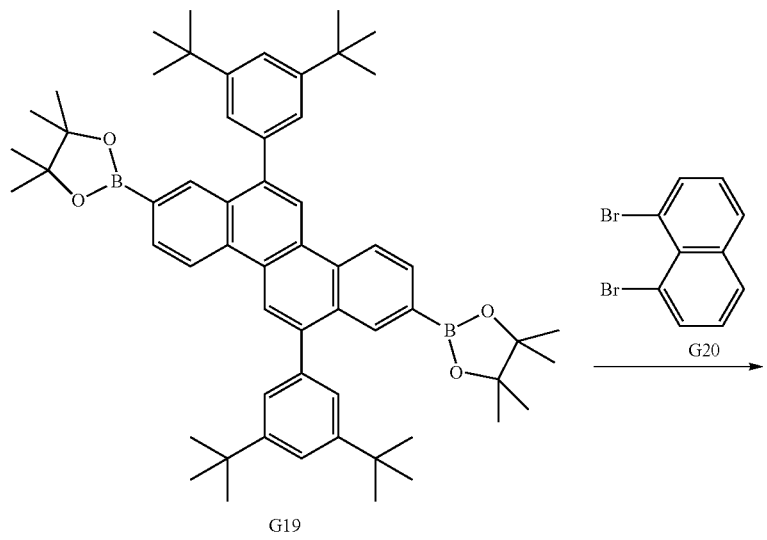
G19
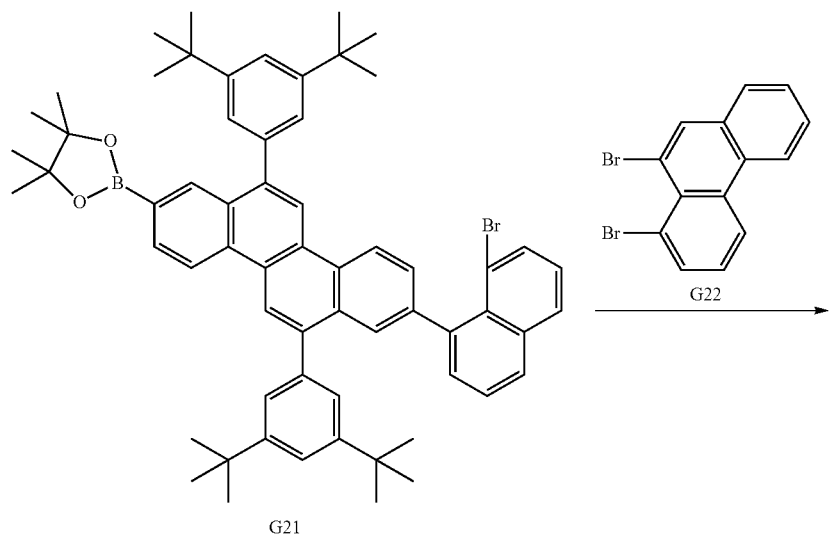
G21

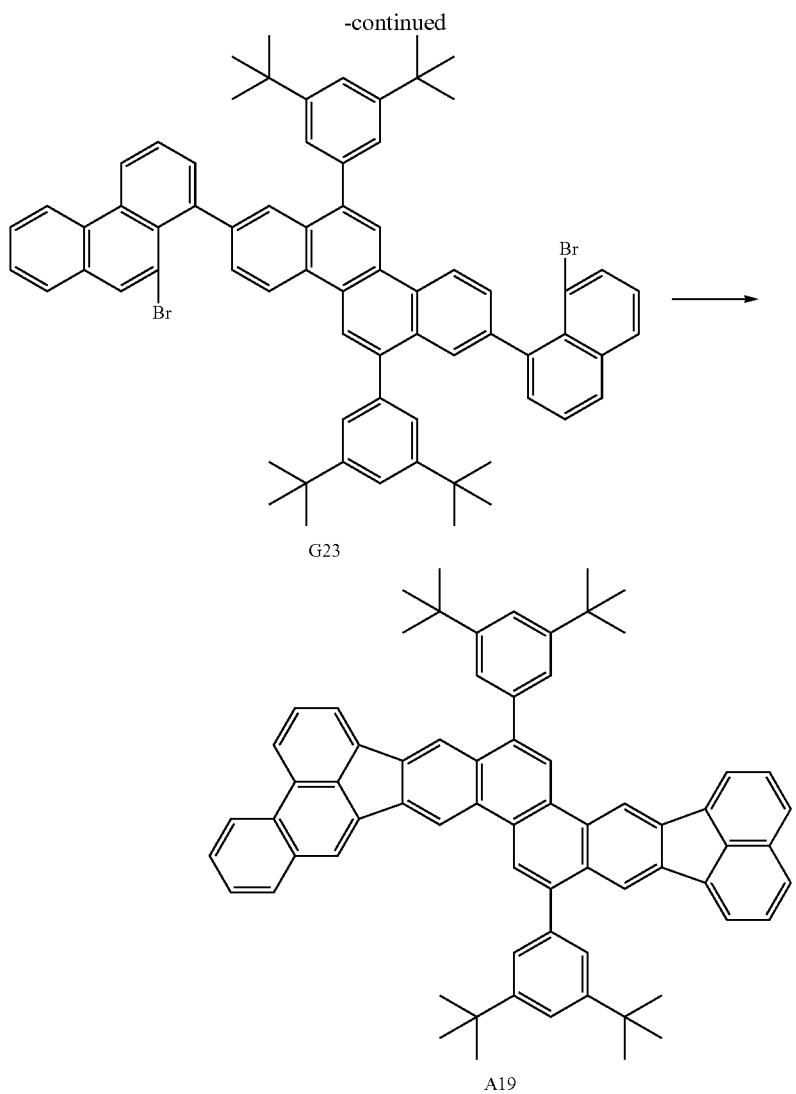

(1) Synthesis of Compound G18

A 500-ml recovery flask was charged with the following reagents and solvents.

Compound G16: 4.54 g (10 mmol)
Compound G17: 5.15 g (22 mmol)
Pd(PPh$_3$)$_4$: 0.2 g
Toluene: 200 ml
Ethanol: 100 ml
2 M aqueous sodium carbonate: 100 ml Next, the reaction solution was heated to 80° C. in a nitrogen stream and was stirred at this temperature (80° C.) for 6 hours. After completion of the reaction, water was added to the product for separation. The product was dissolved in chloroform, was purified by column chromatography (chloroform), and was recrystallized in chloroform/methanol. Thus, 5.26 g (yield: 78%) of a yellow crystalline compound G18 was produced.

(2) Synthesis of Compound G19

A 500-ml recovery flask was charged with the following reagents and solvent.

Compound G18: 5.00 g (7.4 mmol)
Bis(pinacolborane): 11.3 g (44.5 mmol)
Pd(dba)$_2$: 854 mg
Tricyclohexylphosphine (P(Cy)$_3$): 1247 mg
Toluene: 300 ml Next, the reaction solution was heated to 110° C. in a nitrogen stream and was stirred at this temperature (110° C.) for 3 hours. After completion of the reaction, the product was washed twice with 40 ml of water. The organic layer was washed with saturated saline, was dried over magnesium sulfate, and was filtered. The filtrate was concentrated. A brown liquid was produced. The brown liquid was purified by column chromatography (chloroform/heptane=1:4) and was then recrystallized in chloroform/methanol. Thus, 5.41 g (yield: 85%) of a gray crystalline compound G19 was produced.

(3) Synthesis of Compound G21

A 500-ml recovery flask was charged with the following reagents and solvent.

Compound G19: 5.00 g (5.8 mmol)
Compound G20: 1.67 g (5.8 mmol)
Pd(PPh$_3$)$_2$Cl$_2$: 0.41 g
DMSO: 200 ml
Sodium carbonate: 1.24 g Next, the reaction solution was heated to 80° C. in a nitrogen stream and was stirred at this temperature (80° C.)

for 6 hours. After completion of the reaction, water was added to the product for separation. The product was dissolved in chloroform, was purified by column chromatography (chloroform), and was recrystallized in chloroform/methanol. Thus, 3.82 g (yield: 70%) of a white crystalline compound G21 was produced.

(4) Synthesis of Compound G23

A 500-ml recovery flask was charged with the following reagents and solvent.

Compound G21: 3.82 g (4 mmol)
Compound G22: 1.36 g (4 mmol)
Pd(PPh$_3$)$_2$Cl$_2$: 0.3 g
DMSO: 150 ml
Sodium carbonate: 0.86 g Next, the reaction solution was heated to 80° C. in a nitrogen stream and was stirred at this temperature (80° C.) for 6 hours. After completion of the reaction, water was added to the product for separation. The product was dissolved in chloroform, was purified by column chromatography (chloroform), and was recrystallized in chloroform/methanol. Thus, 0.64 g (yield: 15%) of a white crystalline compound G23 was produced.

(5) Synthesis of Exemplary Compound A19

A 20-ml recovery flask was charged with the following reagents and solvent.

Compound G23: 500 mg (5 mmol)
Pd(dba)$_2$: 81 mg
Tricyclohexylphosphine (P(Cy)$_3$): 79 mg
Diazabicycloundecene (DBU): 180 mg
DMF: 20 ml Next, the reaction solution was heated to 145° C. in a nitrogen stream and was stirred at this temperature (145° C.) for 6 hours. After completion of the reaction, ethanol was added to precipitate crystals. The crystals were separated by filtration and were subjected to dispersion washing successively with water, ethanol, and heptane. The resulting yellowish brown crystals were then heated and dissolved in toluene, were subjected to hot filtration, and were recrystallized in toluene/methanol. Thus, 106 mg (yield: 25%) of a yellow exemplary compound A19 was produced.

The compound had a purity of 99% or more as measured by HPLC. The exemplary compound A19 was subjected to mass spectrometry with the MALDI-TOF-MS used in Exemplary Embodiment 1.

[MALDI-TOF-MS]
Actual value: m/z=903.55  Calculated value: C$_{70}$H$_{62}$=903.27

Exemplary Embodiment 5 (Synthesis of Exemplary Compound B17)

An exemplary compound B17 was prepared in the same manner as in Exemplary Embodiment 4 except that the following compound G24 was used instead of the compound G17.

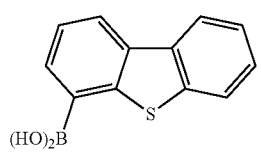
G24

The compound had a purity of 99% or more as measured by HPLC. The exemplary compound B17 was subjected to mass spectrometry with the MALDI-TOF-MS used in Exemplary Embodiment 1.

[MALDI-TOF-MS]
Actual value: m/z=891.26  Calculated value: C$_{66}$H$_{34}$S$_2$=891.12

Exemplary Embodiment 6 (Synthesis of Exemplary Compound A21)

An exemplary compound A21 was prepared in the same manner as in Exemplary Embodiment 4 except that the following compound G25 was used instead of the compound G16, and the following compound G26 was used instead of the compound G17.

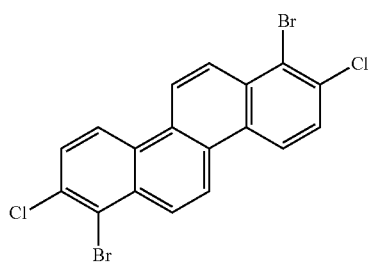
G25

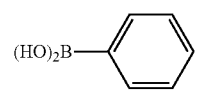
G26

The compound had a purity of 99% or more as measured by HPLC. Mass spectrometry was performed with the MALDI-TOF-MS used in Exemplary Embodiment 1.

[MALDI-TOF-MS]
Actual value: m/z=678.14  Calculated value: C$_{54}$H$_{30}$=678.83

Exemplary Embodiment 7 (Synthesis of Exemplary Compound A22)

An exemplary compound A22 was prepared in the same manner as in Exemplary Embodiment 4 except that the following compound G27 was used instead of the compound G16, and the following compound G28 was used instead of the compound G17.

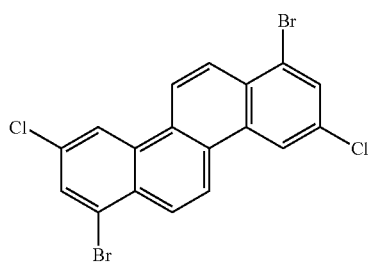
G27

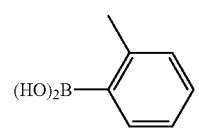
G28

The compound had a purity of 99% or more as measured by HPLC. Mass spectrometry was performed with the MALDI-TOF-MS used in Exemplary Embodiment 1.
[MALDI-TOF-MS]
Actual value: m/z=678.14 Calculated value: $C_{54}H_{30}$=678.83

Comparative Example 2 (Synthesis of Comparative Compound (1))

A comparative compound (1) was prepared in the same manner as in Exemplary Embodiment 4 except that the following compound G29 was used instead of the compound G17, and the following compound G30 was used instead of the compound G22.

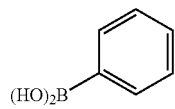

G29

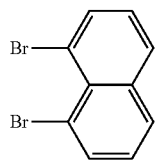

G30

The compound had a purity of 98% or more as measured by HPLC. Mass spectrometry was performed with the MALDI-TOF-MS used in Exemplary Embodiment 1.
[MALDI-TOF-MS]
Actual value: m/z=628.82 Calculated value: $C_{50}H_{28}$=628.77

Exemplary Embodiment 8 (Synthesis of Exemplary Compounds D1 and D2)

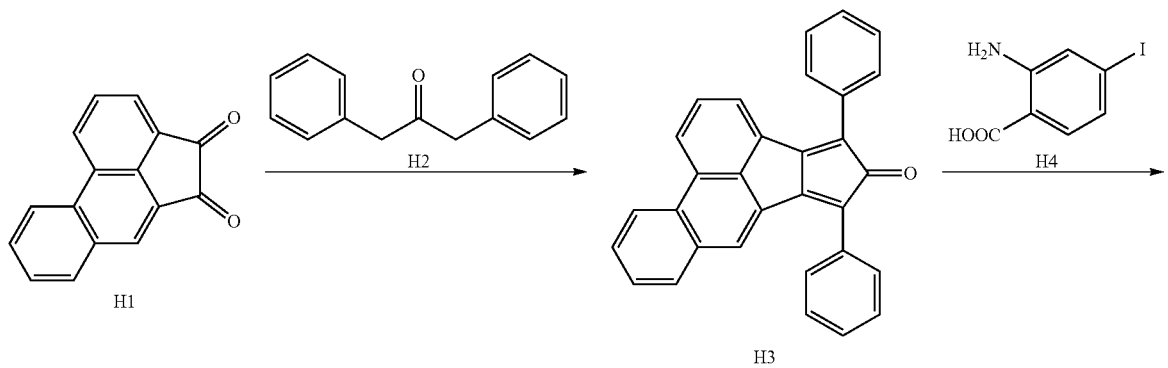

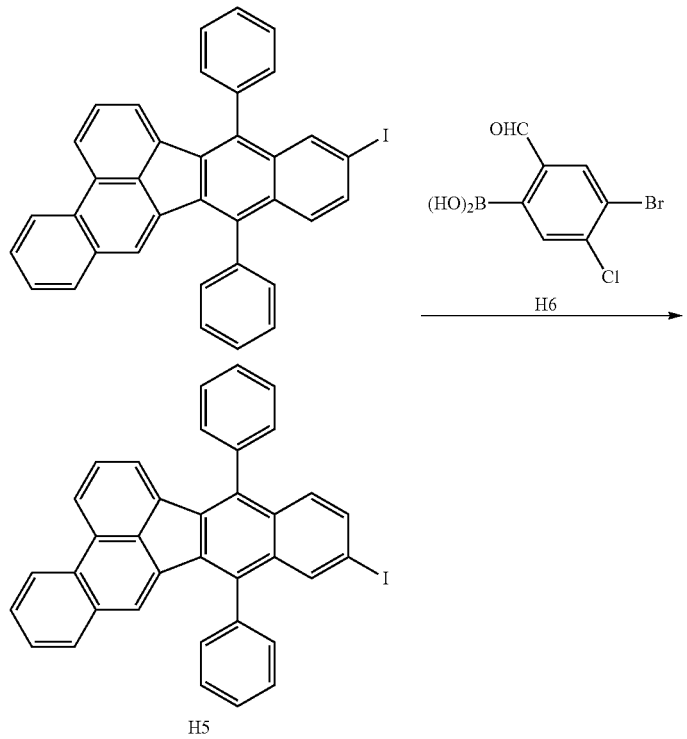

-continued
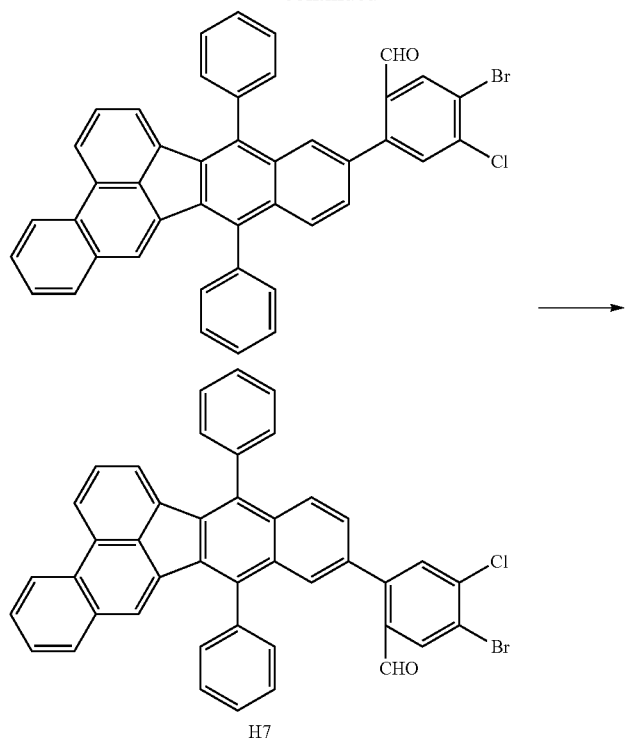
H7
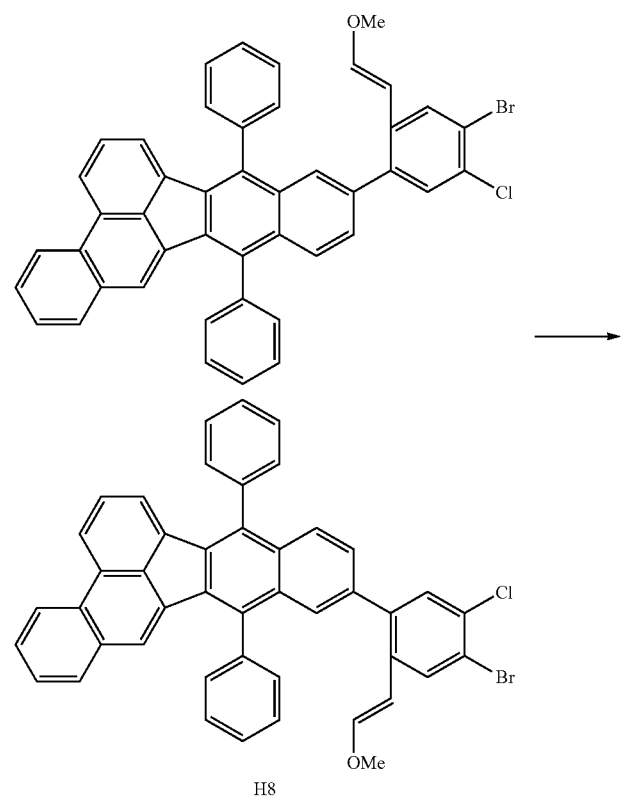
H8

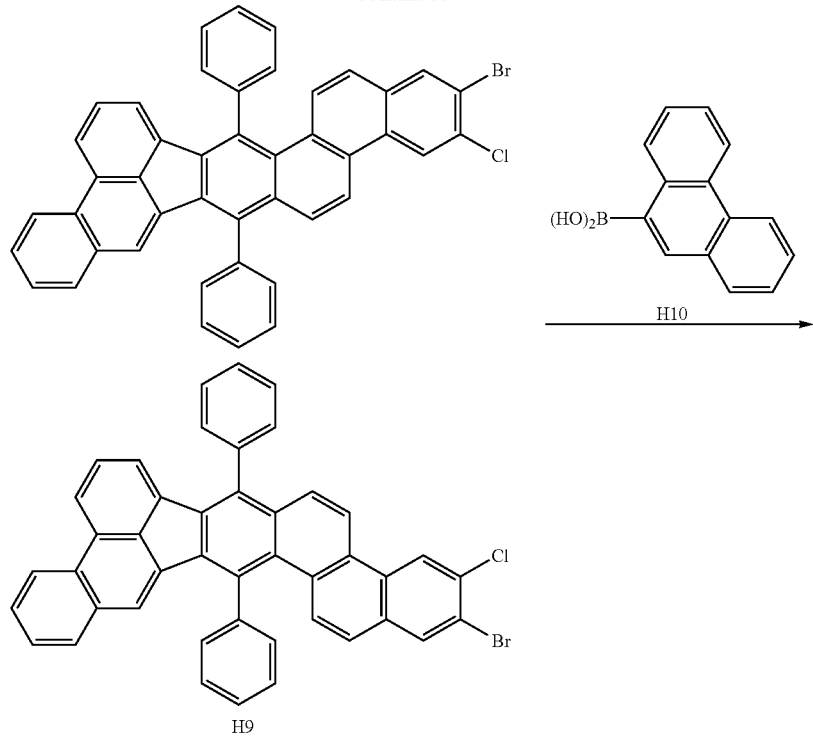
H9
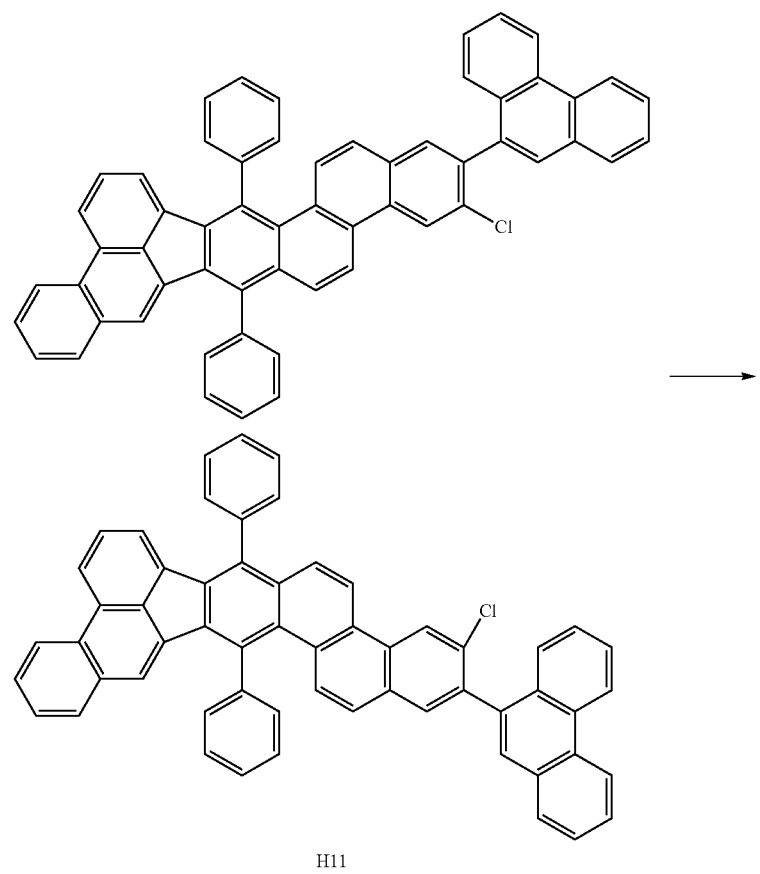
H11

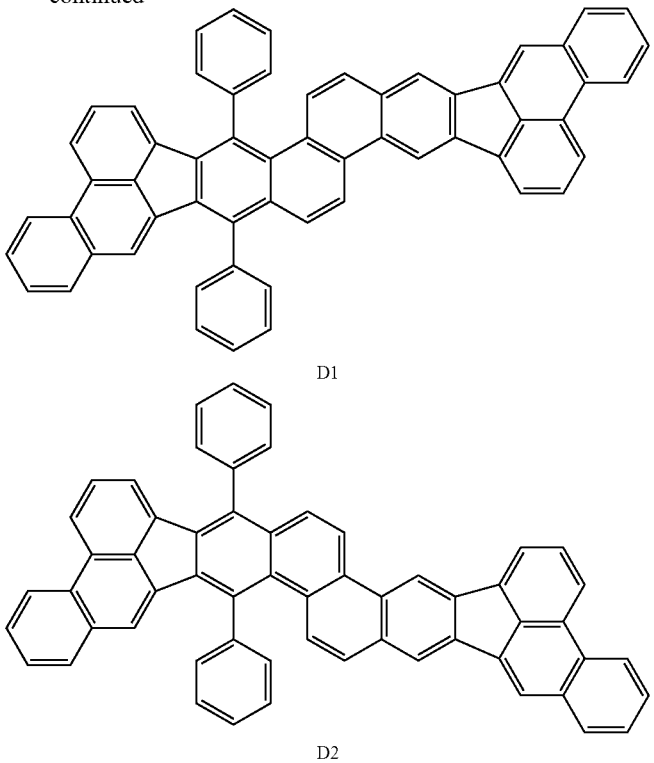

D1

D2

(1) Synthesis of Compound H3

A 200-ml recovery flask was charged with the following reagents and solvent.

Compound H1: 2.32 g (10 mmol)
Compound H2: 2.10 g (10 mmol)
Ethanol: 100 ml

Next, the reaction solution was heated to 70° C. in a nitrogen stream, and a KOH ethanol solution was added dropwise to the reaction solution.

The reaction solution was stirred at this temperature (70° C.) for 6 hours. After completion of the reaction, water was added to the product, and the precipitate was filtered. The filter cake was subjected to dispersion washing with methanol. Thus, 3.04 g (yield: 75%) of a gray compound H3 was produced.

(2) Synthesis of Compound H5

A 100-ml recovery flask was charged with the following reagents and solvent.

Compound H3: 2.84 g (7 mmol)
Compound H4: 2.37 g (9 mmol)
Isoamyl nitrite: 1.05 g (9 mmol)
Toluene: 40 ml Next, the reaction solution was heated to 110° C. in a nitrogen stream and was stirred at this temperature (110° C.) for 3 hours. After completion of the reaction, the product was washed twice with 40 ml of water. The organic layer was washed with saturated saline, was dried over magnesium sulfate, and was filtered. The filtrate was concentrated. A brown liquid was produced. The brown liquid was purified by column chromatography (chloroform/heptane=1:4) and was then recrystallized in chloroform/methanol. Thus, 3.45 g (yield: 85%) of a yellow crystalline compound H5 was produced.

(3) Synthesis of Compound H7

A 200-ml recovery flask was charged with the following reagents and solvents.

Compound H5: 1.74 g (3 mmol)
Compound H6: 0.79 g (3 mmol)
Pd(PPh$_3$)$_4$: 0.03 g
Toluene: 50 ml
Ethanol: 20 ml
2 M aqueous sodium carbonate: 50 ml Next, the reaction solution was heated to 80° C. in a nitrogen stream and was stirred at this temperature (80° C.) for 6 hours. After completion of the reaction, water was added to the product for separation. The product was dissolved in chloroform, was purified by column chromatography (chloroform), and was recrystallized in chloroform/methanol. Thus, 1.51 g (yield: 75%) of a yellow crystalline compound H7 was produced.

(4) Synthesis of Compound H8

The following reagent and solvent in a 100-ml recovery flask were stirred in a nitrogen stream at room temperature for 30 minutes.

(Methoxymethyl)triphenylphosphonium chloride: 1.03 g (3 mmol)
THF: 10 ml

Next, the following reagents were added in this order, and the mixture was stirred in a nitrogen stream at room temperature for 2 hours.

12% tetrahydrofuran solution of potassium tert-butoxide: 3 ml
Compound H7: 1.01 g (1.5 mmol)

After completion of the reaction, water and ethyl acetate were added to the reaction solution. Next, after the organic layer was recovered by a solvent extraction operation, the recovered organic layer was dried over sodium sulfate. Next, the solvent in the organic layer was distilled off under reduced pressure, and the residue was purified by silica gel column chromatography (mobile phase: toluene:heptane=1:1). Thus, 0.94 g (yield: 90%) of a compound H8 was produced as a pale yellow oil.

(5) Synthesis of Compound H9

The following reagent and solvent in a 200-ml recovery flask were stirred in a nitrogen stream at room temperature for 30 minutes.

Compound H8: 0.84 g (1.20 mmol)

Dichloromethane: 25 ml

Next, the following reagent was added, and the mixture was stirred in a nitrogen stream at room temperature for 1 hour.

Methanesulfonic acid: 0.17 g (1.80 mmol)

After completion of the reaction, methanol was added to the reaction solution, and the precipitate was collected. The precipitate was purified by dispersion washing (solvent: methanol). Thus, 0.40 g (yield: 50%) of a compound H9 was produced as a pale yellow solid.

(6) Synthesis of Compound H11

A 200-ml recovery flask was charged with the following reagents and solvents.

Compound H9: 0.30 g (0.45 mmol)

Compound H10: 0.12 g (0.54 mmol)

Pd(PPh$_3$)$_4$: 0.005 g

Toluene: 50 ml

Ethanol: 20 ml

2 M aqueous sodium carbonate: 50 ml

Next, the reaction solution was heated to 80° C. in a nitrogen stream and was stirred at this temperature (80° C.) for 6 hours. After completion of the reaction, water was added to the product for separation. The product was dissolved in chloroform, was purified by column chromatography (chloroform), and was recrystallized in chloroform/methanol. Thus, 0.27 g (yield: 78%) of a yellow crystalline compound H11 was produced.

(7) Synthesis of Exemplary Compounds D1 and D2

A 50-ml recovery flask was charged with the following reagents and solvent.

Compound H11: 200 mg (0.3 mmol)

Pd(dba)$_2$: 45 mg

Tricyclohexylphosphine (P(Cy)$_3$): 44 mg

Diazabicycloundecene (DBU): 99 mg

DMF: 8 ml

Next, the reaction solution was heated to 145° C. in a nitrogen stream and was stirred at this temperature (145° C.) for 6 hours. After completion of the reaction, ethanol was added to precipitate crystals. The crystals were separated by filtration and were subjected to dispersion washing successively with water, ethanol, and heptane. The resulting yellowish brown crystals were then heated and dissolved in toluene, were subjected to hot filtration, and were recrystallized in toluene/methanol. Thus, 95 mg (yield: 50%) of a yellow solid was produced.

The resulting compound was a mixture of exemplary compounds D1 and D2, and the mixture had a purity of 99% or more as measured by HPLC.

The compound was subjected to mass spectrometry with the MALDI-TOF-MS used in Exemplary Embodiment 1.

[MALDI-TOF-MS]

Actual value: m/z=728.84 Calculated value: C$_{58}$H$_{32}$=728.89

Exemplary Embodiment 9 (Synthesis of Exemplary Compounds D3 and D4)

A mixture of exemplary compounds D3 and D4 was prepared in the same manner as in Exemplary Embodiment 8 except that the following compound H12 was used instead of the compound H2.

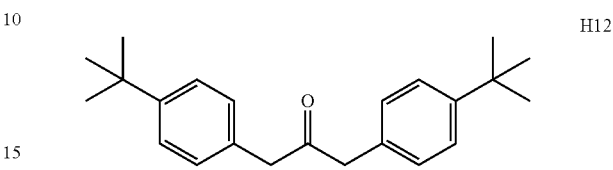

The mixture had a purity of 98% or more as measured by HPLC. Mass spectrometry was performed with the MALDI-TOF-MS used in Exemplary Embodiment 1.

[MALDI-TOF-MS]

Actual value: m/z=841.34 Calculated value: C$_{66}$H$_{48}$=841.11

Exemplary Embodiment 10 (Synthesis of Exemplary Compounds F16 and F17)

A mixture of exemplary compounds F16 and F17 was prepared in the same manner as in Exemplary Embodiment 8 except that the following compound H13 was used instead of the compound H2, and the following compound H14 was used instead of the compound H10.

The mixture had a purity of 98% or more as measured by HPLC. Mass spectrometry was performed with the MALDI-TOF-MS used in Exemplary Embodiment 1.

[MALDI-TOF-MS]

Actual value: m/z=768.82 Calculated value: C$_{58}$H$_{34}$F$_2$=768.91

Exemplary Embodiments 11 to 13

A mixture of exemplary compounds D5 and D6, a mixture of exemplary compounds D9 and D10, and a mixture of exemplary compounds F13 and F14 were synthesized in the same manner as in Exemplary Embodiment 8 except that the compounds shown in Table 10 were used. The compounds were identified by HPLC and with the MALDI-TOF-MS.

TABLE 10

| | H1 | H2 |
|---|---|---|
| Exemplary embodiment 11 | | |
| Exemplary embodiment 12 | | |
| Exemplary embodiment 13 | | |

| | H6 | H10 |
|---|---|---|
| Exemplary embodiment 11 | | |
| Exemplary embodiment 12 | | |
| Exemplary embodiment 13 | | |

TABLE 10-continued
Exemplary compound
Exemplary embodiment 11
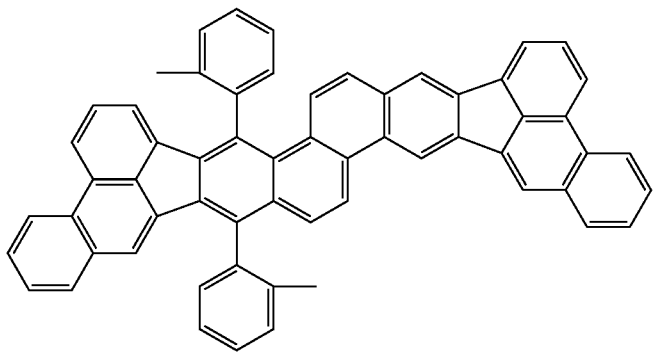
D5
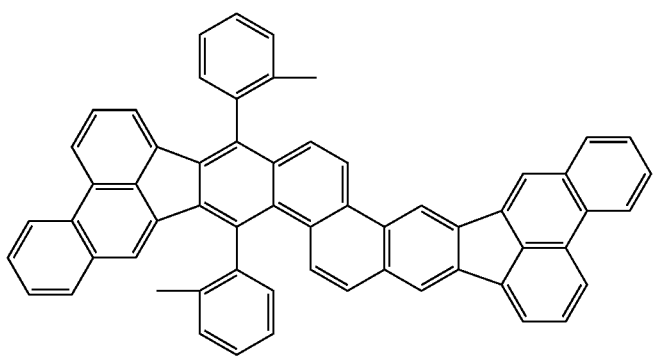
D6
Exemplary embodiment 12
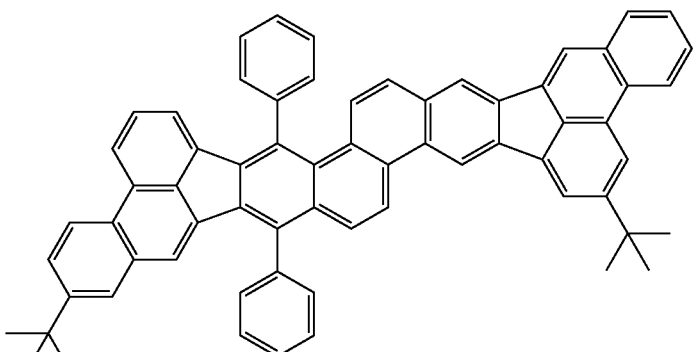
D9
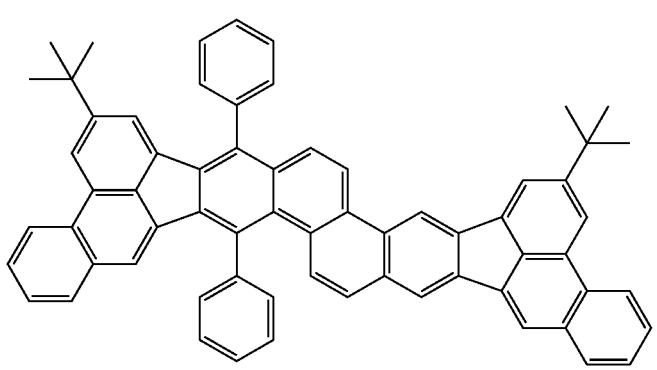
D10

TABLE 10-continued
Exemplary embodiment 13
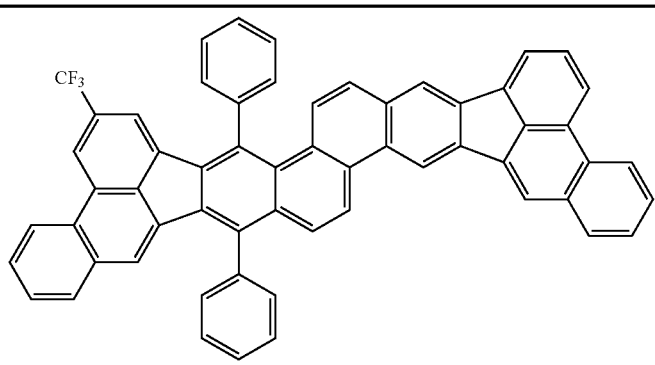
F13
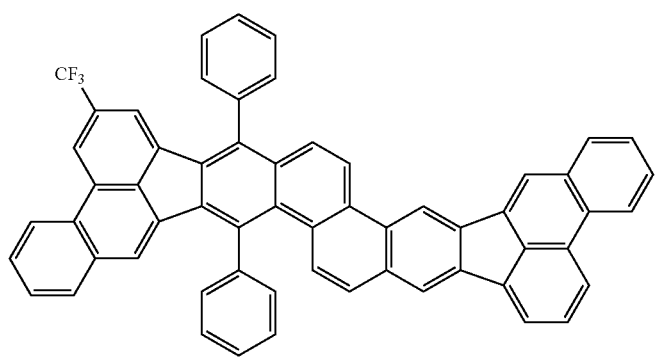
F14
Exemplary Embodiment 14 (Synthesis of Exemplary Compound D19)
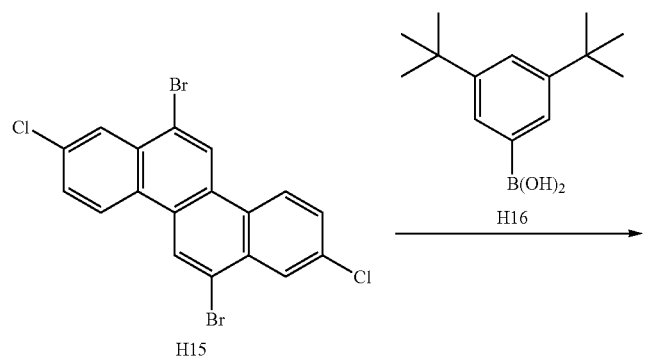

-continued
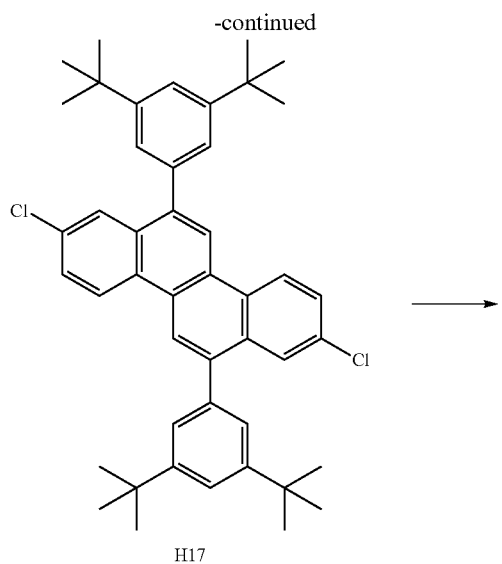
H17
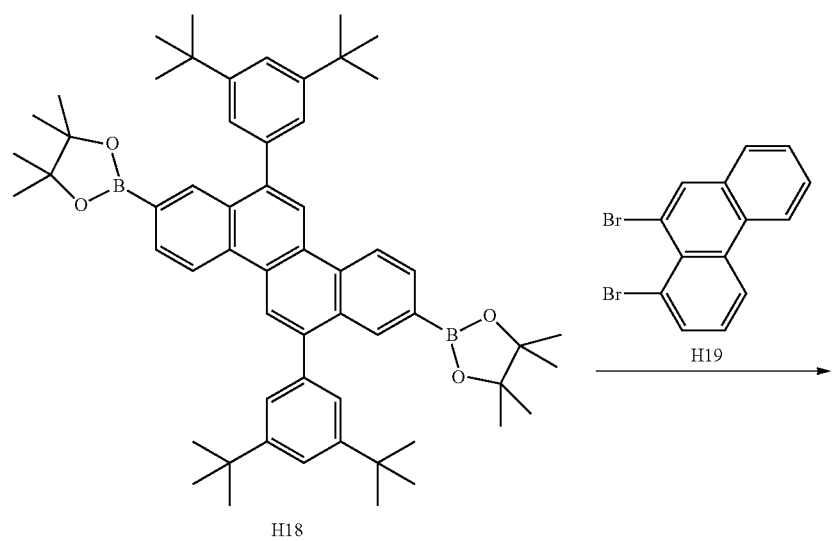
H18
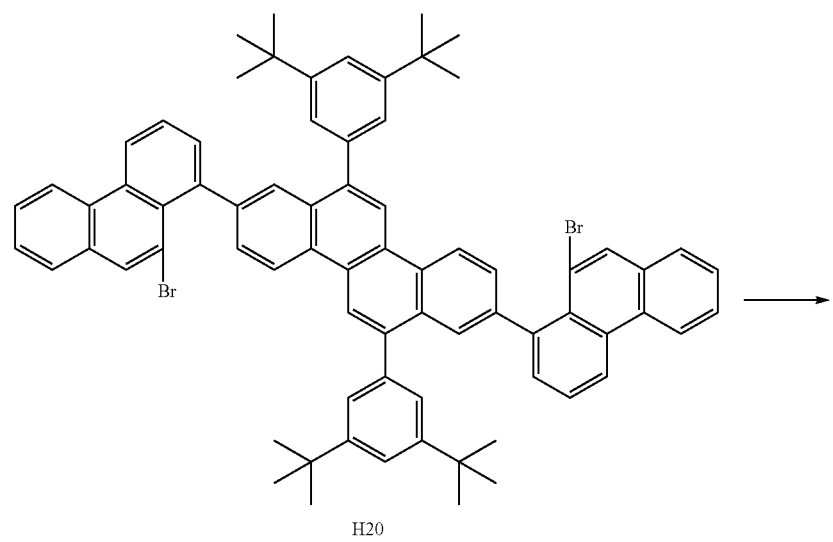
H20

-continued

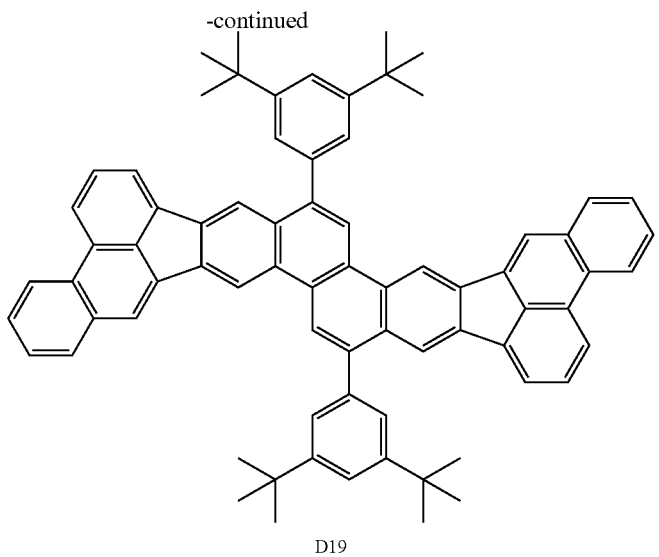

D19

(1) Synthesis of Compound H17

A 500-ml recovery flask was charged with the following reagents and solvents.
Compound H15: 4.54 g (10 mmol)
Compound H16: 5.15 g (22 mmol)
Pd(PPh$_3$)$_4$: 0.2 g
Toluene: 200 ml
Ethanol: 100 ml
2 M aqueous sodium carbonate: 100 ml Next, the reaction solution was heated to 80° C. in a nitrogen stream and was stirred at this temperature (80° C.) for 6 hours. After completion of the reaction, water was added to the product for separation. The product was dissolved in chloroform, was purified by column chromatography (chloroform), and was recrystallized in chloroform/methanol. Thus, 5.26 g (yield: 78%) of a yellow crystalline compound H17 was produced.

(2) Synthesis of Compound H18

A 500-ml recovery flask was charged with the following reagents and solvent.
Compound H17: 5.00 g (7.4 mmol)
Bis(pinacolborane): 11.3 g (44.5 mmol)
Pd(dba)$_2$: 854 mg
Tricyclohexylphosphine (P(Cy)$_3$): 1247 mg
Toluene: 300 ml Next, the reaction solution was heated to 110° C. in a nitrogen stream and was stirred at this temperature (110° C.) for 3 hours. After completion of the reaction, the product was washed twice with 40 ml of water. The organic layer was washed with saturated saline, was dried over magnesium sulfate, and was filtered. The filtrate was concentrated. A brown liquid was produced. The brown liquid was purified by column chromatography (chloroform/heptane=1:4) and was then recrystallized in chloroform/methanol. Thus, 5.41 g (yield: 85%) of a yellow crystalline compound H18 was produced.

(3) Synthesis of Compound H20

A 500-ml recovery flask was charged with the following reagents and solvent.
Compound H18: 1.00 g (1.2 mmol) Compound H19: 0.86 g (2.6 mmol)
Pd(PPh$_3$)$_2$Cl$_2$: 0.08 g
DMSO: 40 ml
Sodium carbonate: 0.49 g Next, the reaction solution was heated to 80° C. in a nitrogen stream and was stirred at this temperature (80° C.) for 6 hours. After completion of the reaction, water was added to the product for separation. The product was dissolved in chloroform, was purified by column chromatography (chloroform), and was recrystallized in chloroform/methanol. Thus, 0.58 g (yield: 45%) of a yellow crystalline compound H20 was produced.

(4) Synthesis of Exemplary Compound D19

A 20-ml recovery flask was charged with the following reagents and solvent.
Compound H20: 500 mg (5 mmol)
Pd(dba)$_2$: 77 mg
Tricyclohexylphosphine (P(Cy)$_3$): 75 mg
Diazabicycloundecene (DBU): 170 mg
DMF: 20 ml Next, the reaction solution was heated to 145° C. in a nitrogen stream and was stirred at this temperature (145° C.) for 6 hours. After completion of the reaction, ethanol was added to precipitate crystals. The crystals were separated by filtration and were subjected to dispersion washing successively with water, ethanol, and heptane. The resulting yellowish brown crystals were then heated and dissolved in toluene, were subjected to hot filtration, and were recrystallized in toluene/methanol. Thus, 171 mg (yield: 40%) of a yellow exemplary compound D19 was produced.

The compound had a purity of 99% or more as measured by HPLC. The exemplary compound D19 was subjected to mass spectrometry with the MALDI-TOF-MS used in Exemplary Embodiment 1.

[MALDI-TOF-MS]

Actual value: m/z=953.42 Calculated value: $C_{74}H_{64}$=953.33

Exemplary Embodiment 15 (Synthesis of Exemplary Compound E17)

An exemplary compound E17 was prepared in the same manner as in Exemplary Embodiment 14 except that the following compound H21 was used instead of the compound H16.

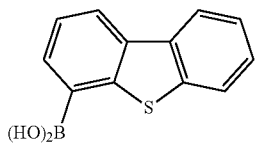

H21

The compound had a purity of 99% or more as measured by HPLC. The exemplary compound E17 was subjected to mass spectrometry with the MALDI-TOF-MS used in Exemplary Embodiment 1.
[MALDI-TOF-MS]
Actual value: m/z=941.66 Calculated value: $C_{70}H_{36}S_2$=941.18

Exemplary Embodiment 16 (Synthesis of Exemplary Compound D21)

An exemplary compound D21 was prepared in the same manner as in Exemplary Embodiment 14 except that the following compound H22 was used instead of the compound H15, and the following compound H23 was used instead of the compound H16.

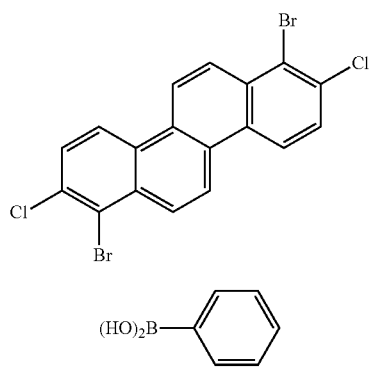

H22

H23

The compound had a purity of 99% or more as measured by HPLC. Mass spectrometry was performed with the MALDI-TOF-MS used in Exemplary Embodiment 1.
[MALDI-TOF-MS]
Actual value: m/z=728.32 Calculated value: $C_{58}H_{32}$=728.89

Exemplary Embodiment 17

An organic EL device of the bottom emission type produced in the present exemplary embodiment included a positive electrode, a hole-injection layer, a hole-transport layer, an electron-blocking layer, a light-emitting layer, a hole-blocking layer, an electron-transport layer, an electron-injection layer, and a negative electrode on a substrate.

First, an ITO film was formed on a glass substrate and was subjected to desired patterning to form an ITO electrode (positive electrode). The ITO electrode had a thickness of 100 nm. The substrate on which the ITO electrode was formed was used as an ITO substrate in the following process. Vacuum evaporation was then performed by resistance heating in a vacuum chamber at $1.33 \times 10^{-4}$ Pa to continuously form an organic EL layer and an electrode layer shown in Table 11 on the ITO substrate. The counter electrode (a metal electrode layer or a negative electrode) had an electrode area of 3 mm². A mixture of the exemplary compounds A1 and A2 was deposited as a guest of the light-emitting layer to form the light-emitting layer.

TABLE 11

| | Material | | Film thickness [nm] |
|---|---|---|---|
| Negative electrode | | Al | 100 |
| Electron-injection layer (EIL) | | LiF | 1 |
| Electron-transport layer (ETL) | | ET2 | 30 |
| Hole-blocking layer (HBL) | | ET13 | 10 |
| Light-emitting layer (EML) | Host | EM4 | 30 |
| | Guest A1, A2 | Mass ratio EM4:A1, A2 = 95:5 | |
| Electron-blocking layer (EBL) | | HT12 | 10 |
| Hole-transport layer (HTL) | | HT3 | 30 |
| Hole-injection layer (HIL) | | HT16 | 10 |

The characteristics of the device were measured and evaluated. The light-emitting device had a maximum emission wavelength of 455 nm and emitted blue light. With respect to measuring apparatuses, the current-voltage characteristics were measured with a microammeter 4140B manufactured by Hewlett-Packard Co., and the emission luminance was measured with a BM7 manufactured by Topcon Corporation. A continuous operation test was performed at a current density of 100 mA/cm², and the time (LT80) when the luminance degradation rate reached 20% was more than 100 hours. Table 12 shows the measurement results.

Exemplary Embodiments 18 to 25 and Comparative Example 3

Organic light-emitting devices were prepared in the same manner as in Exemplary Embodiment 17 except that the compounds shown in Table 12 were used. The characteristics of the devices were measured and evaluated in the same manner as in Exemplary Embodiment 17. Table 12 shows the measurement results.

TABLE 12

| | | | | EML | | | | E.Q.E | LT80 |
|---|---|---|---|---|---|---|---|---|---|
| | HIL | HTL | EBL | Host | Guest | HBL | ETL | [%] | [h] |
| Exemplary embodiment 17 | HT16 | HT3 | HT12 | EM4 | A1, A2 | ET13 | ET2 | 6.0 | 120 |
| Exemplary embodiment 18 | HT2 | HT2 | HT8 | EM1 | C19 | ET12 | ET2 | 5.9 | 115 |
| Exemplary embodiment 19 | HT2 | HT2 | HT8 | EM5 | A18 | ET12 | ET2 | 5.9 | 120 |

TABLE 12-continued

| | HIL | HTL | EBL | EML Host | Guest | HBL | ETL | E.Q.E [%] | LT80 [h] |
|---|---|---|---|---|---|---|---|---|---|
| Exemplary embodiment 20 | HT2 | HT2 | HT11 | EM4 | A22 | ET10 | ET5 | 5.9 | 115 |
| Exemplary embodiment 21 | HT2 | HT2 | HT11 | EM11 | C16, C17 | ET12 | ET3 | 6.2 | 105 |
| Exemplary embodiment 22 | HT16 | HT6 | HT11 | EM5 | B24 | ET13 | ET2 | 5.7 | 100 |
| Exemplary embodiment 23 | HT16 | HT6 | HT8 | EM6 | C18, C19 | ET12 | ET2 | 6.2 | 120 |
| Exemplary embodiment 24 | HT16 | HT6 | HT11 | EM6 | C15 | ET15 | ET5 | 6.0 | 110 |
| Exemplary embodiment 25 | HT16 | HT6 | HT8 | EM32 | A3, A4 | ET13 | ET5 | 5.4 | 100 |
| Comparative example 3 | HT16 | HT3 | HT12 | EM4 | Comparative compound (1) | ET13 | ET2 | 5.2 | 95 |

Table 12 shows that the organic light-emitting device including the comparative compound (1) had an external quantum efficiency (E.Q.E) of 5.2%, and the time (LT80) when the luminance degradation rate reached 20% was 95 hours. By contrast, the devices according to the exemplary embodiments had more efficient emission properties and durability. This is because the guest was a compound with higher quantum yield and better sublimation properties. In Exemplary Embodiment 23, exemplary compounds C18 and C19 were synthesized, and a mixture of the exemplary compounds C18 and C19 at a mass ratio of 1:1 was vapor deposited to form a light-emitting layer.

Exemplary Embodiments 26 to 34 and Comparative Example 4

Organic light-emitting devices were prepared in the same manner as in Exemplary Embodiment 17 except that the compounds shown in Table 13 were used. The characteristics of the devices were measured and evaluated in the same manner as in Exemplary Embodiment 17. Table 13 shows the measurement results. Exemplary Embodiment 26 had a maximum emission wavelength of 456 nm and emitted blue light. The time (LT80) when the luminance degradation rate of Exemplary Embodiment 26 reached 20% was more than 100 hours.

TABLE 13

| | HIL | HTL | EBL | EML Host | Guest | HBL | ETL | E.Q.E [%] |
|---|---|---|---|---|---|---|---|---|
| Exemplary embodiment 26 | HT16 | HT3 | HT11 | EM1 | D1, D2 | ET14 | ET2 | 5.8 |
| Exemplary embodiment 27 | HT2 | HT2 | HT8 | EM1 | D3, D4 | ET12 | ET2 | 5.9 |
| Exemplary embodiment 28 | HT2 | HT2 | HT8 | EM4 | D5, D6 | ET12 | ET2 | 5.9 |
| Exemplary embodiment 29 | HT2 | HT2 | HT11 | EM4 | E24 | ET10 | ET5 | 5.5 |
| Exemplary embodiment 30 | HT2 | HT2 | HT11 | EM5 | D18 | ET12 | ET3 | 5.8 |
| Exemplary embodiment 31 | HT16 | HT6 | HT11 | EM5 | D19 | ET13 | ET2 | 5.8 |
| Exemplary embodiment 32 | HT16 | HT6 | HT8 | EM6 | F15 | ET12 | ET2 | 5.6 |
| Exemplary embodiment 33 | HT16 | HT6 | HT11 | EM6 | F19, F20 | ET15 | ET5 | 6.0 |
| Exemplary embodiment 34 | HT16 | HT6 | HT8 | EM11 | F24 | ET17 | ET5 | 5.7 |
| Comparative example 4 | HT16 | HT3 | HT11 | EM1 | Comparative compound (1) | ET12 | ET2 | 5.2 |

Table 13 shows that the organic light-emitting device including the comparative compound (1) had an E.Q.E as low as 5.2%. This is because the guest was the comparative compound (1) with a low quantum yield. By contrast, the devices according to the exemplary embodiments had efficient emission properties. In Exemplary Embodiment 33, exemplary compounds F19 and F20 were synthesized, and a mixture of the exemplary compounds F19 and F20 at a mass ratio of 1:1 was vapor deposited to form a light-emitting layer.

Exemplary Embodiment 35

An organic EL device of the top emission type produced in the present exemplary embodiment included a positive electrode, a hole-injection layer, a hole-transport layer, an electron-blocking layer, a first light-emitting layer, a second light-emitting layer, a hole-blocking layer, an electron-transport layer, an electron-injection layer, and a negative electrode on a substrate.

A 40-nm Ti film was formed on a glass substrate by sputtering and was patterned by photolithography to form a positive electrode. The counter electrode (a metal electrode layer or a negative electrode) had an electrode area of 3 mm$^2$.

Subsequently, the substrate on which up to a cleaned electrode was formed and a material were mounted in a vacuum evaporator (manufactured by ULVAC, Inc.). After the vacuum evaporator was evacuated to $1.33 \times 10^{-4}$ Pa ($1 \times 10^{-6}$ Torr), UV/ozone cleaning was performed. Subsequently, a film with a layer structure shown in Table 14 was formed and was finally sealed in a nitrogen atmosphere.

TABLE 14

| | Material | | Film thickness [nm] |
|---|---|---|---|
| Negative electrode | Mg Ag | Mass ratio Mg:Ag = 50:50 | 10 |
| Electron-injection layer (EIL) | | LiF | 1 |
| Electron-transport layer (ETL) | | ET2 | 30 |
| Hole-blocking layer (HBL) | | ET12 | 70 |
| Second light-emitting layer (2ndEML) | Second host Second guest (blue dopant) | EM5 A1, A2 | Mass ratio EM5:A1, A2 = 95.0:5.0 | 10 |
| First light-emitting layer (1stEML) | First host First guest (red dopant) Third guest (green dopant) | EM5 RD5 GD10 | Mass ratio EM5:RD5:GD10 = 96.5:0.5:3.0 | 10 |
| Electron-blocking layer (EBL) | | HT7 | 10 |
| Hole-transport layer (HTL) | | HT2 | 20 |
| Hole-injection layer (HIL) | | HT16 | 5 |

The characteristics of the device were measured and evaluated. The device emitted good white light. Furthermore, a continuous operation test was performed at an initial luminance of 2000 cd/m$^2$, and the luminance decay rate after 100 hours was measured. Table 15 shows the results.

Exemplary Embodiments 36 to 43 and Comparative Example 5

Organic light-emitting devices were prepared in the same manner as in Exemplary Embodiment 35 except that the compounds shown in Table 15 were used. The characteristics of the devices were measured and evaluated in the same manner as in Exemplary Embodiment 35. Table 15 shows the measurement results.

TABLE 15

| | 1st EML | | | 2nd EML | | Luminance |
|---|---|---|---|---|---|---|
| | First host | First guest | Third guest | Second host | Second guest | degradation rate [%] |
| Exemplary embodiment 35 | EM5 | RD5 | GD10 | EM5 | A1, A2 | 12 |
| Exemplary embodiment 36 | EM1 | RD5 | GD9 | EM1 | C24 | 15 |
| Exemplary embodiment 37 | EM1 | RD1 | GD4 | EM5 | A18 | 20 |
| Exemplary embodiment 38 | EM4 | RD2 | GD10 | EM6 | A11, A12 | 20 |
| Exemplary embodiment 39 | EM4 | RD7 | GD10 | EM6 | A22 | 15 |
| Exemplary embodiment 40 | EM16 | RD1 | B16 | EM1 | BD9 | 20 |
| Exemplary embodiment 41 | EM17 | RD5 | B16 | EM5 | A1, A2 | 20 |
| Exemplary embodiment 42 | EM1 | RD5 | GD4 | EM5 | A23 | 18 |
| Exemplary embodiment 43 | EM2 | RD6 | GD11 | EM5 | B13, B14 | 20 |
| Comparative example 5 | EM5 | RD5 | GD10 | EM5 | Comparative compound (2) | 25 |

Table 15 shows that the organic light-emitting device including the comparative compound (2) had a luminance degradation rate of 25%. By contrast, the devices according to the exemplary embodiments had improved durability. This is because the guest was a compound that was more easily purified.

Exemplary Embodiment 44 to 52 and Comparative Example 6

Organic light-emitting devices were prepared in the same manner as in Exemplary Embodiment 35 except that the compounds shown in Table 16 were used. The characteristics of the devices were measured and evaluated. Table 16 shows the measurement results. The device according to Exemplary Embodiment 44 emitted good white light.

TABLE 16

| | 1st EML | | | 2nd EML | | Luminescence |
|---|---|---|---|---|---|---|
| | First host | First guest | Third guest | Second host | Second guest | efficiency [Cd/A] |
| Exemplary embodiment 44 | EM5 | RD5 | GD10 | EM5 | D1, D2 | 5 |
| Exemplary embodiment 45 | EM7 | RD5 | GD9 | EM11 | D22 | 5 |
| Exemplary embodiment 46 | EM7 | RD1 | GD3 | EM11 | D18 | 4 |
| Exemplary embodiment 47 | EM4 | RD7 | GD6 | EM6 | D17 | 4 |
| Exemplary embodiment 48 | EM4 | RD7 | GD10 | EM6 | D1, D2 | 5 |
| Exemplary embodiment 49 | EM18 | RD1 | E15 | EM1 | BD9 | 4 |
| Exemplary embodiment 50 | EM18 | RD5 | GD10 | EM5 | F23 | 5 |
| Exemplary embodiment 51 | EM11 | RD1 | GD2 | EM11 | F24 | 4 |
| Exemplary embodiment 52 | EM5 | RD1 | GD2 | EM5 | F19 | 4 |
| Comparative example 6 | EM5 | RD5 | GD10 | EM5 | Comparative compound (2) | 3 |

Table 16 shows that the organic light-emitting device including the comparative compound (2) had a luminescence efficiency as low as 3 cd/A. This is because the guest was the comparative compound (2) with a low quantum yield.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2020-152683 filed Sep. 11, 2020, which is hereby incorporated by reference herein in its entirety.

What is claimed is:

1. An organic compound represented by the following formula [1] or [2]:

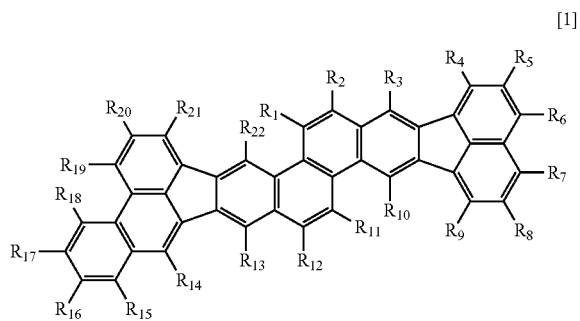

[1]

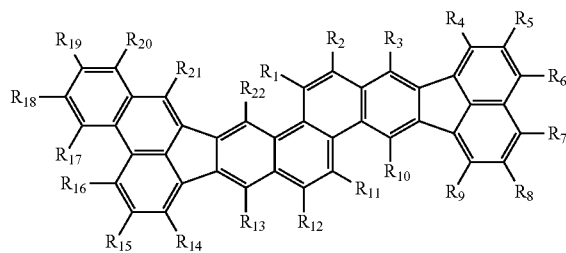

[2]

wherein $R_1$ to $R_{22}$ independently denote a substituent selected from a hydrogen atom, a halogen atom, a substituted or unsubstituted alkyl group, a substituted or unsubstituted alkoxy group, a substituted or unsubstituted amino group, a substituted or unsubstituted aryloxy group, a substituted or unsubstituted silyl group, a cyano group, a trifluoromethyl group, a substituted or unsubstituted aromatic hydrocarbon group, and a substituted or unsubstituted heterocyclic group, and $R_5$ and $R_6$, and/or $R_7$ and $R_8$ may be bonded together to form a ring structure, and when the alkyl group, the alkoxy group, the amino group, the aryloxy group, the silyl group, the aromatic hydrocarbon group, and the heterocyclic group have a substituent, the substituent is independently selected from the group consisting of a halogen atom, an alkyl group, an alkoxy group, an amino group, an aryloxy group, an aromatic hydrocarbon group, a heterocyclic atom, and a cyano group.

2. The organic compound according to claim 1, wherein neither $R_5$ and $R_6$ nor $R_7$ and $R_8$ are bonded together to form a ring structure.

3. The organic compound according to claim 1, represented by one of the following formulae [3] to [5]:

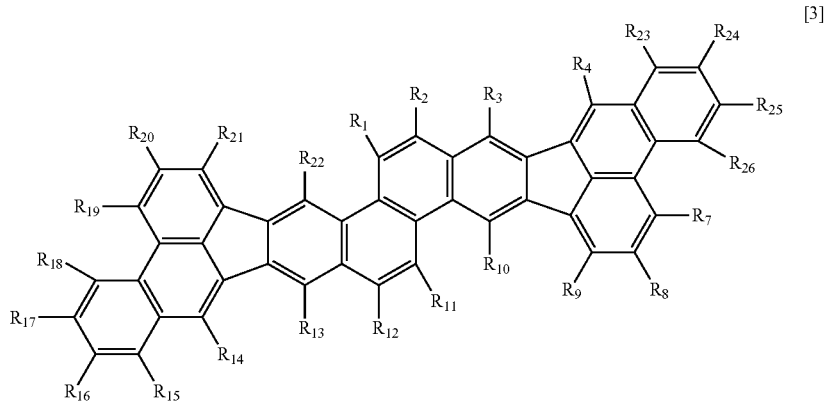

[3]

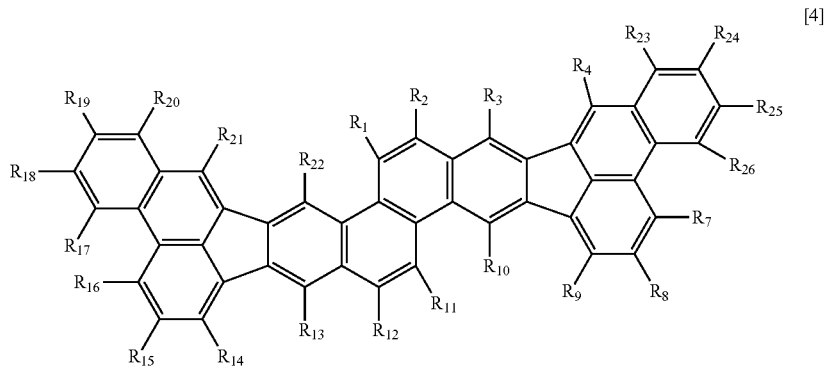

[4]

-continued

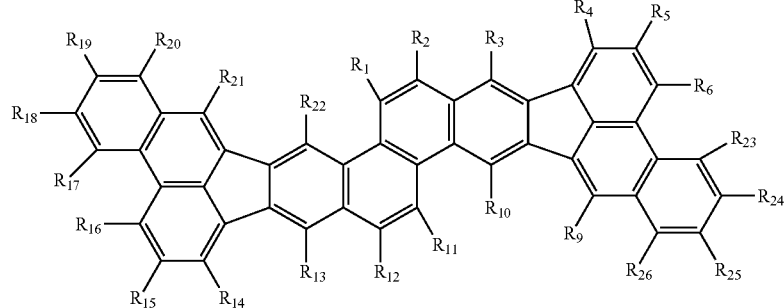

[5]

wherein $R_{23}$ to $R_{26}$ independently denote a substituent selected from a hydrogen atom, a halogen atom, a substituted or unsubstituted alkyl group, a substituted or unsubstituted alkoxy group, a substituted or unsubstituted amino group, a substituted or unsubstituted aryloxy group, a substituted or unsubstituted silyl group, a cyano group, a trifluoromethyl group, a substituted or unsubstituted aromatic hydrocarbon group, and a substituted or unsubstituted heterocyclic group, and when the alkyl group, the alkoxy group, the amino group, the aryloxy group, the silyl group, the aromatic hydrocarbon group, and the heterocyclic group have a substituent, the substituent is independently selected from the group consisting of a halogen atom, an alkyl group, an alkoxy group, an amino group, an aryloxy group, an aromatic hydrocarbon group, a heterocyclic atom, and a cyano group.

4. The organic compound according to claim 1, wherein at least one of $R_1$ to $R_3$, $R_{10}$ to $R_{13}$, and $R_{22}$ is a substituent selected from a substituted or unsubstituted aromatic hydrocarbon group and a substituted or unsubstituted heterocyclic group.

5. The organic compound according to claim 1, wherein at least one of $R_2$ and $R_3$, $R_{10}$, $R_{12}$ and $R_{13}$, and $R_{22}$ is a substituent selected from a substituted or unsubstituted aromatic hydrocarbon group and a substituted or unsubstituted heterocyclic group.

6. The organic compound according to claim 1,
wherein at least one of $R_2$ and $R_3$, $R_{10}$, $R_{12}$ and $R_{13}$, and $R_{22}$ is a substituted or unsubstituted phenyl group or a substituted or unsubstituted naphthyl group.

7. The organic compound according to claim 1, wherein at least one of $R_2$ and $R_3$, $R_{10}$, $R_{12}$ and $R_{13}$, and $R_{22}$ is a phenyl group with a cyano group or a naphthyl group with a cyano group.

8. A mixture of organic compounds comprising:
a first organic compound represented by formula [1]; and
a second organic compound represented by formula [2],

[1]

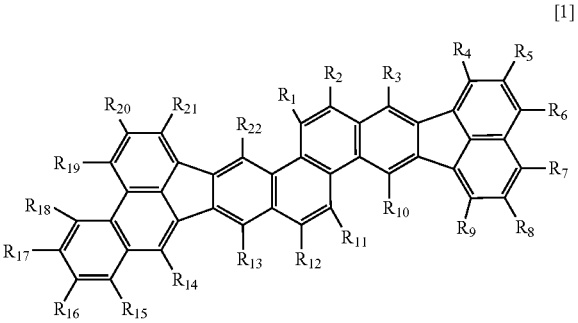

[2]

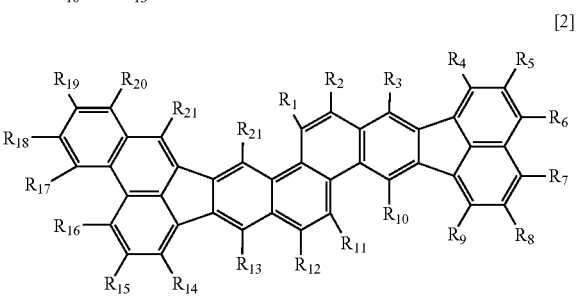

wherein $R_1$ to $R_{22}$ independently denote a substituent selected from a hydrogen atom, a halogen atom, a substituted or unsubstituted alkyl group, a substituted or unsubstituted alkoxy group, a substituted or unsubstituted amino group, a substituted or unsubstituted aryloxy group, a substituted or unsubstituted silyl group, a cyano group, a trifluoromethyl group, a substituted or unsubstituted aromatic hydrocarbon group, and a substituted or unsubstituted heterocyclic group, and $R_5$ and $R_6$, and/or $R_7$ and $R_8$ may be bonded together to form a ring structure, and when the alkyl group, the alkoxy group, the amino group, the aryloxy group, the silyl group, the aromatic hydrocarbon group, and the heterocyclic group have a substituent, the substituent is independently selected from the group consisting of a halogen atom, an alkyl group, an alkoxy group, an amino group, an aryloxy group, an aromatic hydrocarbon group, a heterocyclic atom, and a cyano group.

9. An organic light-emitting device comprising:
a positive electrode;
a negative electrode; and
one or more organic compound layers between the positive electrode and the negative electrode,
wherein at least one of the organic compound layers contains the organic compound according to claim 1.

10. The organic light-emitting device according to claim 9, wherein the at least one of the organic compound layers containing the organic compound is a first light-emitting layer.

11. The organic light-emitting device according to claim 10, wherein the first light-emitting layer has a host and a guest, the host is an aromatic hydrocarbon, and the guest is the organic compound.

12. The organic light-emitting device according to claim 10, further comprising a second light-emitting layer on the first light-emitting layer, wherein the second light-emitting layer emits light of a different emission color from the first light-emitting color.

13. The organic light-emitting device according to claim 12, wherein the organic light-emitting device emits white light.

14. A display apparatus comprising:
a plurality of pixels,
wherein at least one of the pixels includes the organic light-emitting device according to claim 9 and a transistor coupled to the organic light-emitting device.

15. A photoelectric conversion apparatus comprising:
an optical unit with a plurality of lenses;
an imaging device for receiving light passing through the optical unit; and
a display unit for displaying an image taken by the imaging device,
wherein the display unit includes the organic light-emitting device according to claim 9.

16. Electronic equipment comprising:
a display unit including the organic light-emitting device according to claim 9;
a housing to which the display unit is provided; and
a communication unit for communication with an outside provided in the housing.

17. A lighting apparatus comprising:
a light source including the organic light-emitting device according to claim 9; and
a light diffusing unit or an optical filter that transmits light emitted by the light source.

18. A moving body comprising:
a lamp including the organic light-emitting device according to claim 9; and
a body to which the lamp is provided.

19. An exposure light source of an electrophotographic image-forming apparatus, comprising the organic light-emitting device according to claim 9.

20. The mixture of organic compounds according to claim 8, wherein the first organic compound and the second organic compound are isomers.

21. The organic compound according to claim 1, wherein when the alkyl group, the alkoxy group, the amino group, the aryloxy group, the silyl group, the aromatic hydrocarbon group, and the heterocyclic group have a substituent, the substituent is selected from the group consisting of fluorine, chlorine, bromine, iodine, a methyl group, an ethyl group, a n-propyl group, an isopropyl group, a n-butyl group, a tertiary butyl group, an adamantyl group, a cyclopentyl group, a methoxy group, an ethoxy group, a propoxy group, a dimethylamino group, a diethylamino group, a dibenzylamino group, a diphenylamino group, a ditolylamino group, a phenoxy group, a phenyl group, a biphenyl group, a pyridyl group, a pyrrolyl group, and a cyano group.

22. The organic compound according to claim 1, wherein when the alkyl group, the alkoxy group, the amino group, the aryloxy group, the silyl group, the aromatic hydrocarbon group, and the heterocyclic group have a substituent, the substituent is selected from the group consisting of fluorine, chlorine, bromine, iodine, a methyl group, an ethyl group, a n-propyl group, an isopropyl group, a n-butyl group, a tertiary butyl group; a methoxy group, an ethoxy group, a propoxy group, a dimethylamino group, a diethylamino group, a dibenzylamino group, a diphenylamino group, a ditolylamino group, a phenoxy group, a phenyl group, a biphenyl group, a pyridyl group, a pyrrolyl group, and a cyano group.

* * * * *